US011187675B2

(12) United States Patent
Gundlach et al.

(10) Patent No.: US 11,187,675 B2
(45) Date of Patent: Nov. 30, 2021

(54) ANALYTE SEQUENCING WITH NANOPORES

(71) Applicant: University of Washington, Seattle, WA (US)

(72) Inventors: Jens H. Gundlach, Seattle, WA (US); Ian M. Derrington, Seattle, WA (US); Marcus D. Collins, Issaquah, WA (US)

(73) Assignee: University of Washington, Seattle, WA (US)

( * ) Notice: Subject to any disclaimer, the term of this patent is extended or adjusted under 35 U.S.C. 154(b) by 288 days.

(21) Appl. No.: 15/432,897

(22) Filed: Feb. 14, 2017

(65) Prior Publication Data

US 2017/0227494 A1 Aug. 10, 2017

Related U.S. Application Data

(60) Division of application No. 13/592,077, filed on Aug. 22, 2012, now Pat. No. 9,588,079, which is a continuation of application No. PCT/US2011/025963, filed on Feb. 23, 2011.

(60) Provisional application No. 61/375,707, filed on Aug. 20, 2010, provisional application No. 61/307,441, filed on Feb. 23, 2010.

(51) Int. Cl.

| | |
|---|---|
| ***C12Q 1/68*** | (2018.01) |
| ***C12P 19/34*** | (2006.01) |
| ***G01N 27/447*** | (2006.01) |
| ***B82Y 15/00*** | (2011.01) |
| ***C07K 14/35*** | (2006.01) |
| ***B01D 69/06*** | (2006.01) |
| ***C12Q 1/6869*** | (2018.01) |
| *G01N 33/487* | (2006.01) |
| *B82Y 5/00* | (2011.01) |

(52) U.S. Cl.

CPC ....... *G01N 27/44791* (2013.01); *B01D 69/06* (2013.01); *B82Y 15/00* (2013.01); *C07K 14/35* (2013.01); *C12Q 1/6869* (2013.01); *G01N 27/447* (2013.01); *G01N 27/44704* (2013.01); *G01N 27/44726* (2013.01); *G01N 27/44747* (2013.01); *G01N 27/44786* (2013.01); *B01D 2325/02* (2013.01); *B01D 2325/24* (2013.01); *B82Y 5/00* (2013.01); *G01N 33/48721* (2013.01); *Y10S 977/712* (2013.01); *Y10S 977/714* (2013.01); *Y10S 977/781* (2013.01); *Y10S 977/924* (2013.01)

(58) Field of Classification Search

CPC .......... G01N 33/48721; B01D 2325/02; Y10S 977/712; Y10S 977/924; C12Q 1/6869

See application file for complete search history.

(56) References Cited

U.S. PATENT DOCUMENTS

| | | | |
|---|---|---|---|
| 4,307,229 | A | 12/1981 | Liav |
| 4,554,101 | A | 11/1985 | Hopp |
| 4,720,456 | A | 1/1988 | Wagner |
| 5,006,514 | A | 4/1991 | Kato |
| 5,049,664 | A | 9/1991 | Yoshinaga |
| 5,795,782 | A | 8/1998 | Church |
| 6,015,714 | A | 1/2000 | Baldarelli |
| 6,171,830 | B1 | 1/2001 | Verschoor |
| 6,267,872 | B1 | 7/2001 | Akeson |
| 6,362,002 | B1 | 3/2002 | Denison |
| 6,406,880 | B1 | 6/2002 | Thornton |
| 6,428,959 | B1 | 8/2002 | Deamer |
| 6,617,113 | B2 | 9/2003 | Deamer |
| 6,673,615 | B2 | 1/2004 | Denison |
| 6,723,513 | B2 | 4/2004 | Lexow |
| 6,746,594 | B2 | 6/2004 | Akeson |
| 6,936,433 | B2 | 8/2005 | Akeson |
| 7,189,503 | B2 | 3/2007 | Akeson |
| 7,238,485 | B2 | 7/2007 | Akeson |
| 7,444,053 | B2 | 10/2008 | Schmidt |
| 7,514,267 | B1 | 4/2009 | Lopez |
| 7,594,359 | B2 | 9/2009 | Keefe |
| 7,625,764 | B2 | 12/2009 | Stayton |
| 7,713,544 | B2 | 5/2010 | Chaikof |
| 8,673,550 | B2 | 3/2014 | Gundlach |
| 2002/0052412 | A1 | 5/2002 | Verschoor |

(Continued)

FOREIGN PATENT DOCUMENTS

| | | | |
|---|---|---|---|
| CN | 101495656 | A | 7/2009 |
| JP | 07-248329 | A | 9/1995 |

(Continued)

OTHER PUBLICATIONS

Peng H. et al., Nanotechnology 20 (2009), pp. 1-8. (Year: 2009).*

(Continued)

*Primary Examiner* — Stephen T Kapushoc
(74) *Attorney, Agent, or Firm* — Christensen O'Connor Johnson Kindness PLLC

(57) ABSTRACT

Provided herein are methods and systems pertaining to sequencing units of analytes using nanopores. In general, arresting constructs are used to modify an analyte such that the modified analyte pauses in the opening of a nanopore. During such a pause, an ion current level is obtained that corresponds to a unit of the analyte. After altering the modified analyte such that the modified analyte advances through the opening, another arresting construct again pauses the analyte, allowing for a second ion current level to be obtained that represents a second unit of the analyte. This process may be repeated until each unit of the analyte is sequenced. Systems for performing such methods are also disclosed.

21 Claims, 19 Drawing Sheets

Specification includes a Sequence Listing.

(56) References Cited

U.S. PATENT DOCUMENTS

| | | | |
|---|---|---|---|
| 2004/0063200 | A1 | 4/2004 | Chaikof |
| 2006/0008519 | A1 | 1/2006 | Davidsen |
| 2006/0063171 | A1 | 3/2006 | Akeson |
| 2007/0190542 | A1 | 8/2007 | Ling |
| 2007/0269843 | A1 | 11/2007 | Thornton |
| 2009/0298072 | A1 | 12/2009 | Ju |
| 2010/0196203 | A1 | 8/2010 | Sanghera |

FOREIGN PATENT DOCUMENTS

| | | | |
|---|---|---|---|
| WO | 2000/039333 | A1 | 7/2000 |
| WO | 2004/032511 | A1 | 4/2004 |
| WO | 2006/028508 | A2 | 3/2006 |
| WO | 2006/092582 | A1 | 9/2006 |
| WO | 2007/041621 | A2 | 4/2007 |
| WO | 2007/146158 | A1 | 12/2007 |
| WO | 2008/076406 | A2 | 6/2008 |
| WO | 2008/124107 | A1 | 10/2008 |
| WO | 2010/034018 | A1 | 3/2010 |
| WO | 2011/106456 | A2 | 9/2011 |

OTHER PUBLICATIONS

Niederweis, M. “Mycobacterial porins—new channel proteins in unique outer membranes” Molecular Microbiology (2003) 49 (5), 1167-1177. (Year: 2003).*

Purnell, R.F., et al., “Nucleotide Identification and Orientation Discrimination of DNA Homopolymers Immobilized in a Protein Nanopore,” Nano Letters 8(9):3029-3034, Aug. 2008.

Radzicka, A., and R. Wolfenden, “Comparing the Polarities of the Amino Acids: Side-Chain Distribution Coefficients Between the Vapor Phase, Cyclohexane, 1-Octanol, and Neutral Aqueous Solution,” Biochemistry 27(5):1664-1670, Mar. 1988.

Richards, F.N., “Areas, Volumes, Packing and Protein Structure,” Annual Review of Biophysics and Bioengineering 6:151-176, Jun. 1977.

Rose, G.D., et al., “Hydrophobicity of Amino Acid Residues in Globular Proteins,” Science 229(4716):834-838, Aug. 1985.

Sauer-Budge, A.F., et al., “Unzipping Kinetics of Double-Stranded DNA In a Nanopore,” Physical Review Letters 90(23):238101, Jun. 2003, 4 pages.

Schein, C.H., “Solubility as a Function of Protein Structure and Solvent Components,” Nature Biotechnology 8(4):308-317, Apr. 1990.

Second Chinese Office Action, dated Jun. 5, 2014, in corresponding Chinese Application No. 201180018449.5, 8 pages.

Shendure, J.A., et al., “Overview of DNA Sequencing Strategies,” in F.M. Ausubel et al. (eds.), “Current Protocols in Molecular Biology,” Wiley Interscience, New York, Chap. 7, pp. 7.1.1-7.1.11, Jan. 2008.

Singh, A., and J.M. Schnur, “Polymerizable Phospholipids,” in C. Cevc (ed.), “Phospholipids Handbook,” Marcel Dekker Inc., N.Y., pp. 233-287, 1993.

Slonkina, E., and A.B. Kolomeisky, “Polymer Translocation Through a Long Nanopore,” Journal of Chemical Physics 118(15):7112-7118, Apr. 2003.

Smith, D.E., et al., “The Bacteriophage Straight φp29 Portal Motor Can Package DNA Against a Large Internal Force,” Nature 413(6857):748-752, Oct. 2001.

Smith, T.F., and M.S. Waterman, “Comparison of Biosequences,” Advances in Applied Mathematics 2(4):482-489, Dec. 1981.

Song, H., et al., “Construction of Unmarked Deletion Mutants in Mycobacteria,” in T. Parish et al. (eds.), “Mycobacteria Protocols,” Humana Press, Totowa, NJ, pp. 279-295, 2008.

Song, L., et al., “Structure of Staphylococcal α-Hemolysin, a Heptameric Transmembrane Pore,” Science 274(5294):1859-1866, Dec. 1996.

Soni, G.V., and A. Meller, “Progress Toward Ultrafast DNA Sequencing Using Solid-State Nanopores,” Clinical Chemistry 53(11):1996-2001, Nov. 2007.

Stephan, J., et al., “Consecutive Gene Deletions in *Mycobacterium smegmatis* Using the Yeast FLP Recombinase,” Gene 343(1):181-190, Dec. 2004.

Trepagnier, E.H., et al., “Controlling DNA Capture and Propagation Through Artificial Nanopores,” Nano Letters 7(9):2824-2830, Sep. 2007.

Trinquier, G., and Y.H. Sanejouand, “Which Effective Property of Amino Acids Is Best Preserved by the Genetic Code?” Protein Engineering 11(3):153-169, Mar. 1998.

Van Den Hout, M., et al., “Controlling Nanopore Size, Shape and Stability,” Nanotechnology 21(11):115304, Feb. 2010, 6 pages.

Vercoutere, W., et al., “Rapid Discrimination Among Individual DNA Hairpin Molecules at Single-Nucleotide Resolution Using an Ion Channel,” Nature Biotechnology 19(3):248-252, Mar. 2001.

Wang, H., et al., “Identification of CD46 Binding Sites Within the Adenovirus Serotype 35 Fiber Knob,” Journal of Virology 81(23):12785-12792, Dec. 2007.

Williams, G.T., et al., “E1a Transactivation of the Human HSP70 Promoter Is Mediated Through the Basal Franscriptional Complex,” Molecular and Cellular Biology 9(6):2574-2587, Jun. 1989.

Williams, R.M., and M.-N. Im, “Asymmetric Synthesis of Monosubstituted and α,α-Disubstituted α-Amino Acids via Diastereoselective Glycine Enolate Alkylations,” Journal of the American Chemical Society 113(24):9276-9286, Nov. 1991.

Extended European Search Report dated Feb. 6, 2017, in European Application No. 11748022.8, filed Feb. 23, 2011, 15 pages.

Zuker, M., “On Finding All Suboptimal Foldings of an RNA Molecule,” Science 244(4900):48-52, Apr. 1989.

Office Action dated Dec. 12, 2016, in Canadian Application No. 2,790,666, filed Sep. 1, 2011, 5 pages.

Spadola, Q.A., “Novel Approaches to DNA Sequencing,” doctoral dissertation, May 2008, Arizona State University, Tempe, Ariz., <http://cspo.org/legacy/library/090427F1MH_lib_SpadolaQ2008.pdf> [retrieved Jan. 30, 2017], 151 pages.

“University of Washington Receives $1 Million Grant From Amgen Foundation for Undergraduate Science Research Program,” Oct. 16, 2006 press release [retrieved Jan. 29, 2015], Exhibit 3 to the Deposition of Jennifer Harris, *Oxford Nanopore Technologies, Ltd.* v. *The University of Washington and The UAB Research Foundation*, Before the U.S. Patent Trial and Appeal Board, Case No. IPR2014-00513, Feb. 3, 2015, 3 pages.

“About the Amgen Scholars Program: Jun. 18-Aug. 17, 2007,” <https://web.archive.org/web/20070705202640/http:/www.washington.edu/research/urp/stu . . . > [retrieved Jan. 29, 2015], Exhibit 4 to the Deposition of Jennifer Harris, *Oxford Nanopore Technologies, Ltd.* v. *The University of Washington and The UAB Research Foundation*, Before the U.S. Patent Trial and Appeal Board, Case No. IPR2014-00513, Feb. 3, 2015, 1 page.

“2007 Amgen Faculty,” <https://web/archive.org/web/20080907044611//http:/www.washington.edu/research/urp/am . . . > [retrieved Jan. 29, 2015], Exhibit 5 to the Deposition of Jennifer Harris, *Oxford Nanopore Technologies, Ltd.* v. *The University of Washington and The UAB Research Foundation*, Before the U.S. Patent Trial and Appeal Board, Case No. IPR2014-00513, Feb. 3, 2015, 7 pages.

“2007 Amgen Scholars,” <https://web.archive.org/web/20080201130247//http:/www.washington.edu/research/urp/am . . . > [retrieved Jan. 20, 2015], Exhibit 6 to the Deposition of Jennifer Harris, *Oxford Nanopore Technologies, Ltd.* v. *The University of Washington and The UAB Research Foundation*, Before the U.S. Patent Trial and Appeal Board, Case No. IPR2014-00513, Feb. 3, 2015.

Abstract Listing, Exhibit 8 to the Deposition of Jennifer Harris, *Oxford Nanopore Technologies, Ltd.* v. *The University of Washington and The UAB Research Foundation*, Before the U.S. Patent Trial and Appeal Board, Case No. IPR2014-00513, Feb. 3, 2015, 5 pages.

“First Year Amgen Scholars and Leading Scientists Attend Symposium to Explore Drug Discovery & Development,” News Release, Aug. 7, 2007, <http://www.amgen.com/media/media_pr_detail.jsp?releaseID=1037887> [retrieved Jan. 29, 2015], Exhibit 10 to the Deposition of Jennifer Harris, *Oxford Nanopore Technologies, Ltd.* v. *The University of Washington and The UAB Research Foundation*, Before the U.S. Patent Trial and Appeal Board, Case No. IPR2014-00513, Feb. 3, 2015, 2 pages.

(56) References Cited

OTHER PUBLICATIONS

Declaration of Daniel Branton, Exhibit 1044 to *Oxford Nanopore Technologies, Ltd.* v. *The University of Washington and The UAB Research Foundation*, Before the U.S. Patent Trial and Appeal Board, Case No. IPR2014-00513, Mar. 11, 2015, 16 pages.
Jennifer Harris Aug. 14, 2007 Email, Exhibit 1046, submitted Mar. 11, 2015, in support of Petitioner's Reply to Patent Owners' Response for *Oxford Nanopore Technologies, Ltd.* v. *The University of Washington and The UAB Research Foundation*, Before the U.S. Patent Trial and Appeal Board, Case No. IPR2014-00513, 2 pages.
Jennifer Harris Aug. 8, 2007 Email, Exhibit 1047, submitted Mar. 11, 2015, in support of Petitioner's Reply to Patent Owners' Response for *Oxford Nanopore Technologies, Ltd.* v. *The University of Washington and The UAB Research Foundation*, Before the U.S. Patent Trial and Appeal Board, Case No. IPR2014-00513, 2 pages.
Jennifer Harris Aug. 14, 2007 Email, Exhibit 1048, submitted Mar. 11, 2015, in support of Petitioner's Reply to Patent Owners' Response for *Oxford Nanopore Technologies, Ltd.* v. *The University of Washington and The UAB Research Foundation*, Before the U.S. Patent Trial and Appeal Board, Case No. IPR2014-00513, 1 page.
Jennifer Harris Aug. 16, 2007 Email, Exhibit 1049, submitted Mar. 11, 2015, in support of Petitioner's Reply to Patent Owners' Response for *Oxford Nanopore Technologies, Ltd.* v. *The University of Washington and The UAB Research Foundation*, Before the U.S. Patent Trial and Appeal Board, Case No. IPR2014-00513, 1 page.
University of Washington Response to Baker Botts LLP, "Public Records Request PR-2014-00281 (Stage 1)," Nov. 18, 2014, and Jens Gundlach May 5, 2011 Email, Exhibit 1050, submitted Mar. 11, 2015, in support of Petitioner's Reply to Patent Owners' Response for *Oxford Nanopore Technologies, Ltd.* v. *The University of Washington and The UAB Research Foundation*, Before the U.S. Patent Trial and Appeal Board, Case No. IPR2014-00513, 3 pages.
"Purification of Oligonucleotides," Quick Look Version of the Full Technical Report "Chemical Synthesis of Oligonucleotides," © 2009 and 2011 Integrated DNA Technologies, Exhibit 1051, submitted Mar. 11, 2015, in support of Petitioner's Reply to Patent Owners' Response for *Oxford Nanopore Technologies, Ltd.* v. *The University of Washington and The UAB Research Foundation*, Before the U.S. Patent Trial and Appeal Board, Case No. IPR2014-00513, 3 pages.
"ORDER: Conduct of the Proceeding: 37 C.F.R. § 42.5," U.S. Patent Trial and Appeal Board Paper No. 25, issued Feb. 19, 2015, in *Oxford Nanopore Technologies, Ltd.* v. *The University of Washington and The UAB Research Foundation*, Before the U.S. Patent Trial and Appeal Board, Case No. IPR2014-00513, 5 pages.
Maria Vignone Mar. 4, 2015 Email on Behalf of The U.S. Patent Trial and Appeal Board in *Oxford Nanopore Technologies, Ltd.* v. *The University of Washington and The UAB Research Foundation*, Before the U.S. Patent Trial and Appeal Board, Case No. IPR2014-00513, 5 pages.
Supplemental Declaration of Daniel Branton, Exhibit 1052 cited in *Oxford Nanopore Technologies, Ltd.* v. *The University of Washington and The UAB Research Foundation*, Before the U.S. Patent Trial and Appeal Board, Case No. IPR2014-00513, submitted Apr. 1, 2015, 9 pages.
Analytical ESI-MS Report by Integrated DNA Technologies, Exhibit 1053 cited in *Oxford Nanopore Technologies, Ltd.* v. *The University of Washington and The UAB Research Foundation*, Before the U.S. Patent Trial and Appeal Board, Case No. IPR2014-00513, submitted Apr. 1, 2015, 1 page.
Deposition Upon Oral Examination of Daniel Branton in *Oxford Nanopore Technologies, Ltd.* v. *The University of Washington and The UAB Research Foundation*, Before the U.S. Patent Trial and Appeal Board, Case No. IPR2014-00513, Apr. 15, 2015, 165 pages.
Decision Granting Petitioner's Motion for Joinder and Instituting Inter Partes Review, 37 C.F.R. §§ 42.108, 42.122, in U.S. Patent Trial and Appeal Board Case No. IPR2014-00513, *Oxford Nanopore Technologies Ltd.* v. *University of Washington and UAB Research Foundation*, entered Apr. 27, 2015, 31 pages.
Patent Owners' Supplemental Response in U.S. Patent Trial and Appeal Board Case No. IPR2014-00513, *Oxford Nanopore Technologies Ltd.* v. *University of Washington and UAB Research Foundation*, submitted Jun. 29, 2015, 60 pages.
Bayley, H., "Nanopore Sequencing: From Imagination to Reality," Clinical Chemistry 61(1):25-31, 2015, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 11 pages.
Benner, S.A., Ph.D., Declaration, Jun. 26, 2015, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 21 pages.
Branton, D., E-mail dated Jul. 28, 2008, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 30 pages.
Branton, D., E-mail dated Jul. 30, 2008, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 4 pages.
Branton, D., Transcript of Deposition, Apr. 15, 2015, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 165 pages.
Branton, D., Transcript of Deposition, Jun. 19, 2015, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 237 pages.
Chen, P., et al., "Probing Single DNA Molecule Transport Using Fabricated Nanopores," Nano Letters 4(11):2293-2298, Nov. 2004, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 6 pages.
Derrington, I.M., et al., "Nanopore DNA Sequencing With MspA," PNAS 107(37):16060-16065, Sep. 2010, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 6 pages.
"DNA Sequencing—The Hole Story: Nanopores May Lead the Way to a New Generation of Sequencing," The Economist, Oct. 16, 2008, pp. 1-2, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 2 pages.
Griffiths, J., "The Realm of the Nanopore," Analytical Chemistry 80(1):23-27, Jan. 2008, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 5 pages.
Gundlach, J., cover letter to PNAS dated Jul. 31, 2008, including submission of manuscript entitled "Single-molecule DNA detection with an engineered MspA protein nanopore" and supplemental information; and letter from Dr. Daniel Branton to PNAS dated Jul. 30, 2008, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 31 pages.
Heger, M., "Pre-Print Study Demonstrates Nanopore Sequencing of Bacteriophage Genome With MspA Pore," www.genomeweb.com, Jun. 24, 2014, pp. 1-4, exhibit submitted Jun. 29, 2015, in support of Patent Owners' Supplemental Response for U.S. Patent Trial and

(56) References Cited

OTHER PUBLICATIONS

Appeal Board, Case No. IPR2014-00513, *Oxford Nanopore Technologies Ltd.* v. *University of Washington and UAB Research Foundation*, 4 pages.
Heger, M., "Proof-of-Principle Study Shows MspA Is Superior to Alpha-Hemolysin for Protein Nanopore Sequencing," www.genomeweb.com, Aug. 24, 2010, pp. 1-4, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 4 page.
Jain, M., et al., "Improved Data Analysis for the MinION Nanopore Sequencer," Nature Methods 12(4):351-356, Apr. 2015, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 9 pages.
Jetha, N.N., et al., "Forming an α-Hemolysin Nanopore for Single-Molecule Analysis," Chap. 9 of "Micro and Nano Technologies in Bioanalysis, Methods in Molecular Biology," vol. 544, pp. 113-127, 2009, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 15 pages.
Karow, J., "AGBT: Oxford Nanopore to Begin Selling Two Low-Cost DNA Strand Sequencing Instruments This Year," www.genomeweb.com, Feb. 21, 2012, pp. 1-4, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 4 pages.
Gundlach, J., E-mail dated Feb. 19, 2012, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 1 page.
MIT Technology Review, "The Smartest Company in the World. And It's Not Google." Mar./Apr. 2014, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 6 pages.
Myers, T., PNAS Editorial Staff Member, E-mail dated Aug. 22, 2008, exhibit submitted Jun. 29, 2015, in support of Patent Owners' Supplemental Response for U.S. Patent Trial and Appeal Board, Case No. IPR2014-00513, *Oxford Manopore Technologies Ltd.* v. *University of Washington and UAB Research Foundation*, 6 pages.
Nakane, J.J., et al., "Nanopore Sensors for Nucleic Acid Analysis," Journal of Physics: Condensed Matter 15(32):R1365-R1393, Aug. 2003, exhibit submitted Jun. 29, 2015, in support of Patent Owners' Supplemental Response tor U.S. Patent Trial and Appeal Board, Case No. IPR2014-00513, *Oxford Nanopore Technologies Ltd.* v. *University of Washington and UAB Research Foundation*, 29 pages.
Pennisi, E., "Genome Sequencing: Search for Pore-fection," Science 336(6081):534-537, May 2012, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 4 pages.
Rhee, M., and M.A. Burns, "Nanopore Sequencing Technology: Nanopore Preparations," TRENDS in Biotechnology 25(4):174-181, Apr. 2007, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 8 pages.
Sanghera, G., E-mail dated Feb. 4, 2011, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 1 pages.
Timp, W., et al., "Think Small: Nanopores for Sensing and Synthesis," IEEE Access 2:1396-1408, 2014, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 13 pages.
Venkatesan, B.M., and R. Bashir, "Nanopore Sensors for Nucleic Acid Analysis," Nature Nanotechnology 6(0):615-624, Sep. 2011, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 10 pages.
Willcocks, S., E-mail dated Apr. 10, 2009, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 3 pages.
Willcocks, S., E-mail dated Jul. 1, 2009, exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 2 pages.
WO 2012/107778, filed Feb. 11, 2011 (priority date), by ONT entitled "Mutant Pores," exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 110 pages.
WO 2013/014451, filed Jul. 25, 2011 (priority date), by ONT entitled "Hairpin Loop Method for Double Strand Polynucleotide Sequencing Using Transmembrane Pores," exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 92 pages.
WO 2013/057495, filed Oct. 21, 2011 (priority date), by ONT entitled "Method of Characterizing a Target Polynucleotide Using a Pore and a hel308 Helicase," exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 110 pages.
Examination Report dated Dec. 15, 2017, issued in Canadian Application No. 2,790,666, filed Feb. 23, 2011, 3 pages.
European Search Report dated Jul. 20, 2012, issued in European Application No. 09815404.0, filed Sep. 22, 2009, 6 pages.
European Patent Office Communication Pursuant to Rule 114(2) EPC with Third Party Observations, mailed Dec. 3, 2012, issued in European Application No. 09815404.0, filed Sep. 22, 2009, 21 pages.
International Search Report and Written Opinion dated Aug. 18, 2010, issued in International Application No. PCT/US2009/057915, filed Sep. 22, 2009, 12 pages.
Notification of the First Office Action and Search Report dated Jun. 25, 2013, issued in Chinese Application No. 200980142855.5, filed Sep. 22, 2009, 26 pages.
Akeson, M., et al., "Microsecond Time-Scale Discrimination Among Polycytidylic Acid, Polyadenylic Acid, and Polyuridylic Acid as Homopolymers or as Segments Within Single RNA Molecules," Biophysical Journal 77(6):3227-3233, Dec. 1999.
Ball, K.A., "Ion Channel Gating and DNA Translocation in Single MspA Protein Pores," University of Washington Physics REU (Research Experiences for Undergraduates) Summer Research Program, manuscript and presentation slides, drafted and presented Summer 2006, 25 pages.
Bayley, H., and P.S. Cremer, "Stochastic Sensors Inspired by Biology," Nature 413(6852):1226-230, Sep. 2001.
Benner, S., et al., "Sequence-Specific Detection of Individual DNA Polymerase Complexes in Real Time Using a Nanopore," Nature Nanotechnology 2(11):1718-724, Nov. 2007.

(56) References Cited

OTHER PUBLICATIONS

Bossman, S.H., et al., "Nanotechnology on Surfaces Using Mutants of MspA From *Mycobacterium smegmatis*," Abstract 66, The 41st Midwest Regional Meeting, Oct. 25-27, 2006, <http://acs.confex.com/acs/mwrm06/techprogram/P38604.HTM> [retrieved Aug. 21, 2012], 1 page.
Butler, T., "Nanopore Analysis of Nucleic Acids," doctoral dissertation, University of Washington, Seattle, Washington, 2007, 120 pages.
Cockroft, S.L., et al., "A Single-Molecule Nanopore Device Detects DNA Polymerase Activity With Single-Nucleotide Resolution," Journal of the American Chemical Society 130(3):1818-820, Jan. 2008.
Engelhardt, H., et al., "A Tetrameric Porin Limits the Cell Wall Permeability of *Mycobacterium smegmatis*," Journal of Biological Chemistry 277(40):37567-37572, Oct. 2002.
Faller, M., et al., "The Structure of a Mycobacterial Outer-Membrane Channel," Science 303(5661):1189-1192, Feb. 2004.
Gundlach, J., "Engineering MspA for Nanopore Sequencing," Grant Application Abstract, project period Sep. 26, 2006, through Aug. 31, 2008, 1 page.
Gyarfas, B., et al., "Mapping the Position of DNA Polymerase-Bound DNA Templates in a Nanopore at 5 Å Resolution," ACS Nano 3(6):1457-1466, Jun. 2009.
Heinz, C., et al., "The Core of the Tetrameric Mycobacterial Porin MspA Is an Extremely Stable β-Sheet Domain," Journal of Biological Chemistry 278(10):8678-8685, Mar. 2003.
Hoffmann, C., "Construction and Functional Analysis of Constriction Zone Mutants of *Mycobacterium smegmatis* Porin A (MspA)," thesis, University of Erlangen-Nuremberg, Germany, Oct. 2005, 115 pages.
Howorka, S., and H. Bayley, "Probing Distance and Electrical Potential Within a Protein Pore With Tethered DNA," Biophysical Journal 83(6):3202-3210, Dec. 2002.
Huff, J., et al., "Functions of the Periplasmic Loop of the Porin MspA From *Mycobacterium smegmatis*," Journal of Biological Chemistry 284(15):10223-10231, Apr. 2009.
Jayasinghe, L., and H. Bayley, "The Leukocidin Pore: Evidence for an Octamer With Four LukF Subunits and Four LukS Subunits Alternating Around a Central Axis," Protein Science 14(10):2550-2561, Oct. 2005.
Kalita, M., et al., "Enhancing the Water Solubility of Nanoparticles (CdSe, Au, Au/Fe) by Ligand Exchange and Subsequent Binding to a Cysteine Mutant of the Mycobacterial Porin MspA," Abstract 217, The 41st Midwest Regional Meeting, Oct. 25-27, 2006, <http://acs.confex.com/acs/mwrm06/techprogram/P38606.HTM> [retrieved Aug. 21, 2012], 1 page.
Kasianowicz, J.J., et al., "Characterization of Individual Polynucleotide Molecules Using a Membrane Channel," Proceedings of the National Academy of Sciences of the United States of America (PNAS) 93(24):13770-13773, Nov. 1996.
Mahfoud, M., et al., "Topology of the Porin MspA in the Outer Membrane of *Mycobacterium smegmatis*," Journal of Biological Chemistry 281(9):5908-5915, Mar. 2006.
Niederweis, M., et al., "Cloning of the mspA Gene Encoding a Porin From *Mycobacterium smegmatis*," Molecular Microbiology 33(5):933-945, Sep. 1999.
Stahl, C., et al., "MspA Provides the Main Hydrophilic Pathway Through the Cell Wall of *Mycobacterium smegmatis*," Molecular Microbiology 40(2):451-464, Apr. 2001.
Stephan, J., et al., "The Growth Rate of *Mycobacterium smegmatis* Depends on Sufficient Porin-Mediated Influx of Nutrients," Molecular Microbiology 58(3):714-730, Nov. 2005.
Stoddart, D., et al., "Single-Nucleotide Discrimination in Immobilized DNA Oligonucleotides With a Biological Nanopore," Proceedings of the National Academy of Sciences of the United States of America (PNAS) 106(19):7702-7707, May 2009.
Wong, R., "Engineering *Mycobacterium smegmatis* Porin A (MspA) for DNA Analysis," University of Washington Summer Research Poster Session, pamphlet cover, program description, schedule of events, abstract and poster, presentation date Aug. 16, 2007, 5 pages.
Gundlach, J.H., et al., "MSP Nanopores and Related Methods," U.S. Pat. No. 8,673,550, issued Mar. 18, 2014, "Petition for Inter Partes Review of U.S. Pat. No. 8,673,550 Under 35 U.S.C. §§ 311-319 and 37 C.F.R. §§ 42.100 et seq." to the U.S. Patent Trial and Appeal Board, Case No. IPR2014-00512, served Mar. 18, 2014, 67 pages.
Gundlach, J.H., et al., "MSP Nanopores and Related Methods," U.S. Pat. No. 8,673,550, issued Mar. 18, 2014, "Patent Owners' Preliminary Response," *Oxford Nanopore Technologies, Ltd.* v. *The University of Washington and The UAB Research Foundation*, Before the U.S. Patent Trial and Appeal Board, Case No. IPR2014-00512, served Jun. 27, 2014, 20 pages.
Gundlach, J.H., et al., "MSP Nanopores and Related Methods," U.S. Pat. No. 8,673,550, issued Mar. 18, 2014, "Petition for Inter Partes Review of U.S. Pat. No. 8,673,550 Under 35 U.S.C. §§ 311-319 and 37 C.F.R. §§ 42.100 et seq." to the U.S. Patent Trial and Appeal Board, Case No. IPR2014-00513, served Mar. 18, 2014, 69 pages.
Gundlach, J.H., et al., "MSP Nanopores and Related Methods," U.S. Pat. No. 8,673,550, issued Mar. 18, 2014, "Patent Owners' Preliminary Response," *Oxford Nanopore Technologies, Ltd.* v. *The University of Washington and The UAB Research Foundation*, Before the U.S. Patent Trial and Appeal Board, Case No. IPR2014-00513, served Jun. 27, 2014, 35 pages.
"Analyte," online definition at Dictionary.com, Jun. 17, 2014, <http:/dictionary.reference.com/browse/analyse?s=t>, exhibit cited in U.S. Patent Trial and Appeal Board Case No. IPR2014-00513, 2 pages.
Butler, T.Z., et al., "Determination of RNA Orientation During Translocation Through a Biological Nanopore," Biophysical Journal 90(1):190-199, Jan. 2006, exhibit cited in U.S. Patent Trial and Appeal Board Case No. IPR2014-00512 and Case No. IPR2014-00513.
Declaration of Daniel Branton, exhibit cited in U.S. Patent Trial and Appeal Board Case No. IPR2014-00512 and Case No. IPR2014-00513, Mar. 18, 2014, 236 pages.
Declaration of Roland Benz, exhibit cited in U.S. Patent Trial and Appeal Board Case No. IPR2014-00512 and Case No. IPR2014-00513, Mar. 17, 2014, 124 pages.
Deamer, D.W., and M. Akeson, "Nanopores and Nucleic Acids: Prospects for Ultrarapid Sequencing," Trends in Biotechnology (TIBTECH) 18(4):147-151, Apr. 2000, exhibit cited in U.S. Patent Trial and Appeal Board Case No. IPR2014-00512 and Case No. IPR2014-00513.
Dörner, U., et al., "Identification of a Cation-Specific Channel (TipA) in the Cell Wall of the Gram-Positive Mycolata Tsukamurella inchonensis: The Gene of the Channel-Forming Protein Is Identical to mspA of *Mycobacterium smegmatis* and mppA of *Mycobacterium phlei*," Biochimica et Biophysica Acta 1667(1):47-55, Nov. 2004, exhibit cited in U.S. Patent Trial and Appeal Board Case No. IPR2014-00512 and Case No. IPR2014-00513.
Entry into the European Phase Before the European Patent Office, mailed Jan. 28, 2011, issued in corresponding European Patent Application No. 09815404.0, filed Sep. 22, 2009, exhibit cited in U.S. Patent Trial and Appeal Board Case No. IPR2014-00512 and Case No. IPR2014-00513, 3 pages.
Gundlach, J.H., "Engineering MspA for Nanopore Sequencing," National Human Genome Research Institute Grant No. 1R21HG004145-01, awarded Sep. 25, 2006, exhibit cited in U.S. Patent Trial and Appeal Board Case No. IPR2014-00512 and Case No. IPR2014-00513, 38 pages.
Gundlach, J.H., "Engineering MspA for Nanopore Sequencing," National Human Genome Research Institute Grant Supplement No. 5R21HG004145-02, awarded Aug. 20, 2007, exhibit cited in U.S. Patent Trial and Appeal Board Case No. IPR2014-00512 and Case No. IPR2014-00513, 13 pages.
Heinz, C., et al., "Mycobacterial Porins—New Channel Proteins in Unique Membranes," Conference of the German Society of Biochemistry 2005, <http://www.vetmed.uni-giessen.de:80/pharmtox/veranstaltungen/rauisch_05/abstracts.pdf> as of Dec. 17, 2005, exhibit cited in U.S. Patent Trial and Appeal Board Case No. IPR2014-00512 and Case No. IPR2014-00513, 1-page abstract.

(56) References Cited

OTHER PUBLICATIONS

Hornblower, B., et al., "Single-Molecule Analysis of DNA-Protein Complexes Using Nanopores," Nature Methods 4(4):315-317, Apr. 2007, exhibit cited in U.S. Patent Trial and Appeal Board, Case No. IPR2014-00512 and Case No. IPR2014-00513.
Howorka, S., et al., "Sequence-Specific Detection of Individual DNA Strands Using Engineered Nanopores," Nature Biotechnology 19(7):636-639, Jul. 2001, exhibit cited in U.S. Patent Trial and Appeal Board Case No. IPR2014-00512 and Case No. IPR2014-00513.
Letter Accompanying Subsequently Filed Items, submitted Feb. 14, 2013, in corresponding European Patent Application No. 09815404.0, filed Sep. 22, 2009, exhibit cited in U.S. Patent Trial and Appeal Board Case No. IPR2014-00512 and Case No. IPR2014-00513, 15 pages.
Meller, A., et al., "Rapid Nanopore Discrimination Between Single Polynucleotide Molecules," Proceedings of the National Academy of Science USA (PNAS) 97(3):1079-1084, Feb. 2000, exhibit cited in U.S. Patent Trial and Appeal Board Case No. IPR2014-00512 and Case No. IPR2014-00513.
Meller, A., et al., "Voltage-Driven DNA Translocations Through a Nanopore," Physical Review Letters 86(15):3435-3438, Apr. 2001, exhibit cited in U.S. Patent Trial and Appeal Board Case No. IPR2014-00512 and Case No. IPR2014-00513.
National Human Genome Research Institute response to Baker Botts LLP Freedom of Information Act request, Dec. 13, 2013, exhibit cited in U.S. Patent Trial and Appeal Board Case No. IPR2014-00512 and Case No. IPR2014-00513, 1 page.
"Licensing Deal Marks Coming of Age for UAB-UW Nanopore Sequencing Technology," Press Release, UAB News, <http://www.uab.news/innovation/item/3847-licensing-deal-marks-coming-of-age-for-uab-uw-nanopore -sequencing-technology.html> [retrieved Mar. 13, 2014], exhibit cited in U.S. Patent Trial and Appeal Board Case No. IPR2014-00512 and Case No. IPR2014-00513, 4 pages.
ProQuest response to e-mail inquiry re Thomas Butler's dissertation, Nov. 4, 2013, exhibit cited in U.S. Patent Trial and Appeal Board Case No. IPR2014-00512 and Case No. IPR2014-00513, 1 page.
Trias, J., and R. Benz, "Characterization of the Channel Formed by the Mycobacterial Porin in Lipid Bilayer Membranes," Journal of Biological Chemistry 268(9):6234-6240, Mar. 1993, exhibit cited in U.S. Patent Trial and Appeal Board Case No. IPR2014-00512 and Case No. IPR2014-00513.
Trias, J., and R. Benz, "Permeability of the Cell Wall of *Mycobacterium smegmatis*," Molecular Microbiology 14(2):283-290, Oct. 1994, exhibit cited in U.S. Patent Trial and Appeal Board Case No. IPR2014-00512 and Case No. IPR2014-00513.
Vercouture, W.A., et al., "Discrimination Among Individual Watson-Crick Base Pairs at the Termini of Single DNA Hairpin Molecules," Nucleic Acids Research 31(4):1311-1318, Feb. 2003, exhibit cited in U.S. Patent Trial and Appeal Board Case No. IPR2014-00512 and Case No. IPR2014-00513.
Vercouture, W., et al., "Rapid Discrimination Among Individual DNA Hairpin Molecules at Single-Nucleotide Resolution Using an Ion Channel," Nature Biotechnology 19(3):248-252, Mar. 2001, exhibit cited in U.S. Patent Trial and Appeal Board Case No. IPR2014-00512 and Case No. IPR2014-00513.
Wang, H., and D. Branton, "Nanopores With a Spark for Single-Molecule Detection," Nature Biotechnology 19(7):622-623, Jul. 2001, exhibit cited in U.S. Patent Trial and Appeal Board Case No. IPR2014-00512 and Case No. IPR2014-00513.
Wang, H., et al., "DNA Heterogeneity and Phosphorylation Unveiled by Single-Molecule Electrophoresis," Proceedings of the National Academy of Science USA (PNAS) 101(37):13472-13477, Sep. 2004, exhibit cited in U.S. Patent Trial and Appeal Board Case No. IPR2014-00512 and Case No. IPR2014-00513.
Bayley, H., and L. Jayasinghe, "Functional Engineered Channels and Pores (Review)," Molecular Membrane Biology 21(4):209-220, Jul.-Aug. 2004.
Branton, D., et al., "The Potential and Challenges of Nanopore Sequencing," Nature Biotechnology 26(10):1146-1153, Oct. 2008.
Deamer, D.W., and D. Branton, "Characterization of Nucleic Acids by Nanopore Analysis," Accounts of Chemical Research 35(10):817-825, Oct. 2002.
Meller, A., and D. Branton, "Single Molecule Measurements of DNA Transport Through a Nanopore," Electrophoresis 23(16):2583-2591, Aug. 2002.
Movileanu, L., "Interrogating Single Proteins Through Nanopores: Challenges and Opportunities," Trends in Biotechnology 27(6):333-341, Jun. 2009.
Decision in U.S. Patent Trial and Appeal Board Case No. IPR2014-00512, *Oxford Nanopore Technologies Ltd.* v. *University of Washington and UAB Research Foundation*, Sep. 15, 2014, 22 pages.
Decision in U.S. Patent Trial and Appeal Board Case No. IPR2014-00513, *Oxford Nanopore Technologies Ltd.* v. *University of Washington and UAB Research Foundation*, Sep. 15, 2014, 30 pages.
Clarke, J., et al., "Continuous Base Identification for Single-Molecule Nanopore DNA Sequencing," Nature Nanotechnology 4:265-270, 2009.
Maglia, G., et al., "Enhanced Translocation of Single DNA Molecules Through α-Hemolysin Nanopores by Manipulation of Internal Change," Proceedings of the National Academy of Science USA 105(50):19720-19725, 2008.
Declaration of Lindsey Miles, executed May 27, 2014, 3 pages.
Gundlach, J.H., et al., "MSP Nanopores and Related Methods," U.S. Pat. No. 8,673,550, issued Mar. 18, 2014, "Petition for Inter Partes Review of U.S. Pat. No. 8,673,550 Under 35 U.S.C. §§ 311-319 and 37 C.F.R. §§ 42.100 at seq." to the U.S. Patent Trial and Appeal Board, Case No. IPR2015-00057, served Oct. 13, 2014, 64 pages.
Gundlach, J.H., et al., "MSP Nanopores and Related Methods," U.S. Pat. No. 8,673,550, issued Mar. 18, 2014, "Motion for Joinder and/or Consolidation With Related Instituted Inter Partes Review" to the U.S. Patent Trial and Appeal Board, Case No. IPR2015-00057, served Oct. 13, 2014, 11 pages.
Communication Pursuant to Rule 114(2) EPC, European Patent Application No. 09815404.0, Nov. 27, 2012, exhibit cited in U.S. Patent Trial and Appeal Board Case No. IPR2015-00057, 20 pages.
Communication Pursuant to Article 94(3) EPC, European Patent Application No. 09815404.0, Jun. 20, 2014, exhibit cited in U.S. Patent Trial and Appeal Board Case No. IPR2015-00057, 6 pages.
Correspondence With U.S. Patent and Trademark Office, U.S. Appl. No. 13/069,187, filed Mar. 22, 2011, exhibit cited in U.S. Patent Trial and Appeal Board Case No. IPR2015-00057, 119 pages.
Declaration of Daniel Branton, exhibit cited in U.S. Patent Trial and Appeal Board Case No. IPR2015-00057, Oct. 11, 2014, 91 pages.
Declaration of James Willcocks, exhibit cited in U.S. Patent Trial and Appeal Board Case No. IPR2015-00057, Oct. 13, 2014, 4 pages.
Declaration of Roland Benz, exhibit cited in U.S. Patent Trial and Appeal Board Case No. IPR2015-00057, Oct. 13, 2014, 71 pages.
International Patent Application No. PCT/US2009/057915, filed Sep. 22, 2009, exhibit cited in U.S. Patent Trial and Appeal Board Case No. IPR2015-00057, 143 pages.
National Institutes of Health Public Health Service Grant Instructions, exhibit cited in U.S. Patent Trial and Appeal Board Case No. IPR2015-00057, 66 pages.
U.S. Appl. No. 61/098,938, filed Sep. 22, 2008, exhibit cited in U.S. Patent Trial and Appeal Board Case No. IPR2015-00057, 33 pages.
Patent Owners' Motion to Amend in U.S. Patent Trial and Appeal Board Case No. IPR2014-00513, *Oxford Nanopore Technologies Ltd.* v. *University of Washington and UAB Research Foundation*, filed on Dec. 11, 2014, 7 pages.
Patent Owners' Response in U.S. Patent Trial and Appeal Board Case No. IPR2014-00513, *Oxford Nanopore Technologies Ltd.* v. *University of Washington and UAB Research Foundation*, filed on Dec. 11, 2014, 33 pages.
Declaration of Steven A. Benner, Ph.D., exhibit in U.S. Patent Trial and Appeal Board Case No. IPR2014-00513, *Oxford Nanopore Technologies Ltd.* v. *University of Washington and UAB Research Foundation*, filed on Dec. 11, 2014, 33 pages.
Declaration of Jennifer Harris, exhibit in U.S. Patent Trial and Appeal Board Case No. IPR2014-00513, *Oxford Nanopore Tech-*

(56) References Cited

OTHER PUBLICATIONS

*nologies Ltd.* v. *University of Washington and UAB Research Foundation*, filed on Dec. 11, 2014, 3 pages.
Pamphlet of University of Washington Summer Research Poster Session, Seattle, Washington, Aug. 16, 2007, exhibit in U.S. Patent Trial and Appeal Board Case No. IPR2014-00513, *Oxford Nanopore Technologies Ltd.* v. *University of Washington and UAB Research Foundation*, filed on Dec. 11, 2014, 56 pages.
Patent Owners' Preliminary Response in U.S. Patent Trial and Appeal Board Case No. IPR2015-00057, *Oxford Nanopore Technologies Ltd.* v. *University of Washington and UAB Research Foundation*, filed on Jan. 29, 2015, 34 pages.
Project Information Page for Project No. 1R21HG004145 01: http://projectreporter.nih.gov/project_info_details.cfm?aid=7192749&icde=22969799 [retrieved Jan. 20, 2015], exhibit cited in Patent Owners' Preliminary Response in U.S. Patent Trial and Appeal Board Case No. IPR2015-00057, 1 page.
Funding Opportunity Announcement for RFA-HG-05-004: http://grants.nih.gov/grants/guide/rfa-files/RFA-HG-05-004.html [retrieved Jan. 20, 2015], exhibit cited in Patent Owners' Preliminary Response in U.S. Patent Trial and Appeal Board Case No. IPR2015-00057, 23 pages.
Butler, T.Z., et al., "Single-Molecule DNA Detection With an Engineered MspA Protein Nanopore," Proceedings of the National Academy of Sciences of the United States of America (PNAS) 105(52):20647-20652, Dec. 2008.
Rhee, M., and M.A. Burns, "Nanopore Sequencing Technology: Research Trends and Applications," Trends in Biotechnology 24(12):580-586, Dec. 2006.
Notification of the First Office Action and Search Report dated Apr. 23, 2014, issued in Chinese Application No. 201180018451.2, filed Feb. 23, 2011, 7 pages.
International Search Report and Written Opinion dated Nov. 28, 2011, issued in corresponding International Application No. PCT/US2011/025963, filed Feb. 23, 2011, 9 pages.
Notification of the Third Office Action dated Oct. 29, 2014, issued in corresponding Chinese Patent Application No. 201180018449.5, filed Feb. 23, 2011, 3 pages.
Notification of the Second Office Action dated Dec. 3, 2014, issued in Chinese Patent Application No. 201180018451.2, filed Feb. 23, 2011, 10 pages.
International Preliminary Report on Patentability dated Aug. 28, 2012, issued in corresponding International Application No. PCT/US2011/025963, filed Feb. 23, 2011, 6 pages.
International Search Report and Written Opinion dated Dec. 7, 2011, issued in related International Application No. PCT/US2011/025960, filed Feb. 23, 2011, 6 pages.
Notification of the First Office Action dated Oct. 8, 2013, issued in corresponding Chinese Patent Application No. 201180018449.5, filed Feb. 23, 2011, 12 pages.
Peng, H., et al., "Reverse DNA Translocation Through a Solid-State Nanopore by Magnetic Tweezers," Nanotechnology 20(18):185101, May 2009, pp. 1-8.
"Petitioner's Reply to Patent Owners' Response," *Oxford Nanopore Technologies, Ltd.* v. *The University of Washington and The UAB Research Foundation*, Before the U.S. Patent Trial and Appeal Board, Case No. IPR2014-00513, served Mar. 11, 2015, 20 pages.
Deposition of Steven A. Benner, Exhibit 1042 to *Oxford Nanopore Technologies, Ltd.* v. *The University of Washington and The UAB Research Foundation*, Before the U.S. Patent Trial and Appeal Board, Case No. IPR2014-00513, Feb. 12, 2015, 141 pages.
"PAGE and HPLC Purification," <http://www.idtdna.com/pages/products/dna-rna/hplc-page> [retrieved Feb. 9, 2015], Exhibit 5 to the Deposition of Steven A. Benner, *Oxford Nanopore Technologies, Ltd.* v. *The University of Washington and The UAB Research Foundation*, Before the U.S. Patent Trial and Appeal Board, Case No. IPR2014-00513, Feb. 12, 2015, 2 pages.
Deposition Upon Oral Examination of Jennifer Harris, Exhibit 1045 to *Oxford Nanopore Technologies, Ltd.* v. *The University of Washington and The UAB Research Foundation*, Before the U.S. Patent Trial and Appeal Board, Case No. IPR2014-00513, Feb. 3, 2015, 75 pages.
Notice of Deposition of Jennifer Harris, Exhibit 1 to the Deposition of Jennifer Harris, *Oxford Nanopore Technologies, Ltd.* v. *The University of Washington and The UAB Research Foundation*, Before the U.S. Patent Trial and Appeal Board, Case No. IPR2014-00513, Jan. 26, 2015, 3 pages.
WO 2013/098562, filed Dec. 29, 2011 (priority date), by ONT entitled "Enzyme Method," exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 39 pages.
WO 2014/135838, filed Mar. 8, 2013 (priority date), by ONT entitled "Enzyme Stalling Method," exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 109 pages.
WO 2015/055981, filed Oct. 18, 2013 (priority date), by ONT entitled "Modified Enzymes," exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 146 pages.
WO 2015/056028, filed Oct. 18, 2013 (priority date), by ONT entitled "Method of Characterizing a Target Ribonucleic Acid (RNA) Comprising Forming a Complementary Polynucleolide Which Moves Through a Transmembrane Pore," exhibit submitted Jun. 29, 2015, in support of Patent Owners' Supplemental Response for U.S. Patent Trial and Appeal Board, Case No. IPR2014-00513, *Oxford Nanopore Technologies Ltd.* v. *University of Washington and UAB Research Foundation*, 67 pages.
Ashkenasy, N., et al., "Recognizing a Single Base in an Individual DNA Strand: A Step Toward DNA Sequencing in Nanopores," Angewandte Chemie International Edition 44(9):1401-1404, Feb. 2005.
Barry, III, C.E., et al., "Mycolic Acids: Structure, Biosynthesis and Physiological Functions," Progress in Lipid Research 37(2-3):143-179, Jul.-Aug. 1998.
Baumann, G., et al., "Polarity as a Criterion in Protein Design," Protein Engineering 2(5):329-334, Jan. 1989.
Benner, S., et al., "Sequence-Specific Detection of Individual DNA Polymerase Complexes in Real Time Using a Nanopore," Nature Nanotechnology 2(11):718-724, Nov. 2007.
Bentley, D.R., "Whole-Genome Re-Sequencing," Current Opinion in Genetics & Development 16(6):545-552, Dec. 2006.
Bentley, D.R., et al., "Accurate Whole Human Genome Sequencing Using Reversible Terminator Chemistry," Nature 456(7218):53-59, Nov. 2008.
Bi, W., and P.J. Stambrook, "CCR: A Rapid and Simple Approach for Mutation Detection," Nucleic Acids Research 25(14):2949-2951, Jul. 1997.
Butler, T.Z., et al., "Ionic Current Blockades From DNA and RNA Molecules in the α-Hemolysin Nanopore," Biophysical Journal 93(9):3229-3240, Nov. 2007.
Chen, P., and C.M. Li, "Nanopore Unstacking of Single-Stranded DNA Helices," Small 3(7):1204-1208, Jul. 2007.
Churbanov, A., et al., "Duration Learning for Analysis of Nanopore Ionic Current Blockades," BMC Bioinformatics 8(Suppl 7):S14, Nov. 2007, 15 pages.
Derrington, I.M., et al., "Nanopore DNA Sequencing With MspA," Proceedings of the National Academy of Sciences USA (PNAS) 107(37):16060-16065, Sep. 2010.
Drmanac, R., et al., "Human Genome Sequencing Using Unchained Base Reads on Self-Assembling DNA Nanoarrays," Science 327(5961):78-81, Jan. 2010.
Evans, D.A., et al., "The Asymmetric Synthesis of α-Amino Acids. Electrophilic Azidation of Chiral Imide Enolates, a Practical Approach to the Synthesis of (R)- and (S)-α-Azido Carboxylic Acids," Journal of the American Chemical Society 112(10):4011-4030, May 1990.

(56) References Cited

OTHER PUBLICATIONS

Fuller, C.W., et al., "The Challenges of Sequencing by Synthesis," Nature Biotechnology 27(11):1013-1023, Nov. 2009.
Ghosn, B., et al., "Control of DNA Hybridization With Photocleavable Adducts," Photochemistry and Photobiology 81(4):953-959, Jul.-Aug. 2005.
Goldstein, D.B., "Common Genetic Variation and Human Traits," New England Journal of Medicine 360(17):1696-1698, Apr. 2009.
Gosse, C., and V. Croquette, "Magnetic Tweezers: Micromanipulation and Force Measurement at the Molecular Level," Biophysical Journal 82(6):3314-3329, Jun. 2002.
Gundlach, J.H., et al., "Artificial Mycolic Acid (MyA) Membranes and Nanopore DNA Sequencing With MyA," U.S. Appl. No. 61/307,441, filed Feb. 23, 2010, 47 pages.
Gundlach, J.H., et al., "Single-Molecule DNA Detection With an Engineered MspA Protein Nanopore," U.S. Appl. No. 61/098,938, filed Sep. 22, 2008.
Heinz, C., and M. Niederweis, "Selective Extraction and Purification of a Mycobacterial Outer Membrane Protein," Analytical Biochemistry 285(1):113-120, Oct. 2000.
Heinz, C., et al., "Purification of Porins From *Mycobacterium smegmatis*," Methods in Molecular Biology 228:139-150, 2003.
Heron, A.J., et al., "Simultaneous Measurement of Ionic Current and Fluorescence From Single Protein Pores," Journal of the American Chemical Society 131(5):1652-1653, Jan. 2009.
Hirschhorn, J.N., "Genomewide Association Studies—Illuminating Biologic Pathways," New England Journal of Medicine 360(17):1699-1701, Apr. 2009.
Hoffmann, C., et al., "Disclosure of the Mycobacterial Outer Membrane: Cryo-Electron Tomography and Vitreous Sections Reveal the Lipid Bilayer Structure," Proceedings of the National Academy of Sciences USA (PNAS) 105(10):3963-3967, Mar. 2008.
Huston, J.S., et al., "Protein Engineering of Antibody Binding Sites: Recovery of Specific Activity in an Anti-Digoxin Single-Chain Fv Analogue Produced in *Escherichia coli*," Proceedings of the National Academy of Sciences USA (PNAS) 85(16):5879-5883, Aug. 1988.
International Preliminary Report on Patentability, dated Mar. 22, 2011, issued in corresponding International Patent Application No. PCT/US2009/057915, filed Sep. 22, 2009, 7 pages.
Jaeger, J.A., et al., "Improved Predictions of Secondary Structures for RNA," Proceedings of the National Academy of Sciences USA (PNAS) 86(20):7706-7710, Oct. 1989.
Jaeger, J.A., et al., "Predicting Optimal and Suboptimal Secondary Structure for RNA," Methods in Enzymology 183:281-306, 1990.
Janin, J., "Surface and Inside Volumes in Globular Proteins," Nature 277(5696):491-492, Feb. 1979.
Kim, Y.-R., et al., "Detecting Translocation of Individual Single Stranded DNA Homopolymers Through a Fabricated Nanopore Chip," Frontiers in Bioscience 12:2978-2983, May 2007.
Läuger, P., "Ion Transport Through Pores: A Rate-Theory Analysis," Biochimica et Biophysica Acta—Biomembranes 311(3):423-441, Jul. 1973.
Lee, J.W., and A. Meller, "Rapid DNA Sequencing by Direct Nanoscale Reading of Nucleotide Bases on Individual DNA Chains," in K. Mitchelson (ed.), "Perspectives in Bioanalysis: New High Throughput Technologies for DNA Sequencing and Genomics," Elsevier, Oxford, U.K., vol. 2, Chap. 8, pp. 245-263, 2007.
Li, J., et al., "DNA Molecules and Configurations in a Solid-State Nanopore Microscope," Nature Materials 2(9):611-615, Aug. 2003.
Long, K.N., et al., "Photomechanics of Light-Activated Polymers," Journal of the Mechanics and Physics of Solids 57(7):1103-1121, Jul. 2009.
Mathé, J., et al., "Nanopore Unzipping of Individual DNA Hairpin Molecules," Biophysical Journal 87(5):3205-3212, Nov. 2004.
McNally, B., et al., "Optical Recognition of Converted DNA Nucleotides for Single-Molecule DNA Sequencing Using Nanopore Arrays," Nano Letters 10(6):2237-2244, May 2010.
Meller, A., et al., "Rapid Nanopore Discrimination Between Single Polynucleotide Molecules," Proceedings of the National Academy of Sciences USA (PNAS) 97(3):1079-1084, Feb. 2000.
Miller, S., et al., "Interior and Surface of Monomeric Proteins," Journal of Molecular Biology 196(3):641-656, Aug. 1987.
Morris, J.R., et al., "The SUMO Modification Pathway Is Involved in the BRCA1 Response to Genotoxic Stress," Nature 462(7275):886-890, Dec. 2009.
Nakane, J., et al., "A Nanosensor for Transmembrane Capture and Identification of Single Nucleic Acid Molecules," Biophysical Journal 87(1):615-621, Jul. 2004.
Needleman, S.B., and C.D. Wunsch, "A General Method Applicable to the Search for Similarities in the Amino Acid Sequence of Two Proteins," Journal of Molecular Biology 48(3):443-453, Mar. 1970.
Osaki, T., et al., "Multichannel Simultaneous Measurements of Single-Molecule Translocation in α-Hemolysin Nanopore Array," Analytical Chemistry 81(24):9866-9870, Dec. 2009.
Pagel, M., et al., "Phenotypic Characterization of Pore Mutants of the Vibrio cholera Porin OmpU," Journal of Bacteriology 189(23):8593-8600, Dec. 2007.
Pearson, W.R., and D.J. Lipman, "Improved Tools for Biological Sequence Comparison," Proceedings of the National Academy of Sciences USA (PNAS) 85(8):2444-2448, Apr. 1988.
Pu, Y., et al., "Synthesis and Acylation of Salts of L-Threonine β-Lactone: A Route to β-Lactone Antibiotics," Journal of Organic Chemistry 56(3):1280-1283, Feb. 1991.
Purnell, R.F., and J.J. Schmidt, "Discrimination of Single Base Substitutions in a DNA Strand Immobilized in a Biological Nanopore," ACS Nano 3(9):2533-2538, Aug. 2009.
Faller, B., "Artifical Membrane Assays to Assess Permeability," Current Drug Metabolism 9(9):886-892, 2008.
Kansy, M., et al., "High-Throughput Artificial Membrane Permeability Studies in Early Lead Discovery and Development," Pharmacokinetic Optimization in Drug Research 447-464, 2001.
Niederweis, M., et al., "Mycobacterial Outer Membranes: In Search of Proteins," Trends Microbiology 18(3):109-116, Mar. 2010.
Office Action dated Apr. 30, 2020, in corresponding Canadian Application No. 3,005,841, filed Feb. 23, 2011, 4 pages.
Schiffler, B., et al., "Corynebacterium diphtheriae: Identification and Characterization of a Channel-Forming Protein in the Cell Wall," Journal of Bacteriology 189(21):7709-7719, Nov. 2007.

* cited by examiner

SEQ ID NO: 1

SEQ ID NO: 2

*SEQ ID NO: 3*

DNA 3' ATGC 5' *SEQ ID NO: 1*

Vapp=180mV, #exp = 5

| Associated base | N | Level Residual Currents (pA) Level order First | Second | Third | Fourth |
|---|---|---|---|---|---|
| ATGC | 175 | 65.4±2.1 | 45.7±1.9 | 62.1±2.5 | 47.7±2.6 |
| ATG | 268 | 65.9±2.1 | 45.8±2.3 | 60.9±3.4 | |
| TGC | 76 | 44.7±2.4 | 61.7±2.7 | 48.1±2.7 | |
| AT | 563 | 65.9±3.0 | 47.1±3.0 | | |
| TG | 109 | 44.6±2.1 | 62.4±3.6 | | |

Vapp=160mV, #exp = 3

| | | | | | |
|---|---|---|---|---|---|
| ATGC | 66 | 54.4±1.6 | 36.0±2.0 | 50.2±2.2 | 37.4±1.8 |
| ATG | 65 | 54.1±1.2 | 35.6±2.5 | 49.3±2.9 | |
| TGC | 8 | 31.3±12.9 | 42.1±17.1 | 32.6±13.5 | |
| AT | 189 | 53.7±2.0 | 36.3±2.8 | | |
| TG | 36 | 36.4±3.5 | 51.0±2.8 | | |

Vapp=140mV, #exp = 3

| | | | | | |
|---|---|---|---|---|---|
| ATGC | 44 | 41.3±1.8 | 23.9±1.1 | 37.4±1.7 | 27.4±1.7 |
| ATG | 47 | 41.3±1.3 | 23.5±0.9 | 36.6±2.1 | |
| TGC | 26 | 24.7±3.4 | 37.7±3.7 | 27.5±5.2 | |
| AT | 132 | 40.8±1.9 | 23.9±2.0 | | |
| TG | 30 | 25.9±2.4 | 39.2±3.3 | | |

*Fig.10.*

DNA 3' TACG 5' *SEQ ID NO: 2*

Vapp=180mV, #exp = 5

| Associated base | N | First | Second | Third | Fourth |
|---|---|---|---|---|---|
| | | Level Residual Currents (pA) Level order | | | |
| TACG | 101 | 43.4±0.7 | 61.4±2.4 | 47.9±1.7 | 59.8±2.6 |
| TAC | 181 | 43.4±1.3 | 62.0±2.3 | 48.3±2.8 | |
| ACG | 20 | 58.0±13.9 | 44.5±10.7 | 56.8±13.7 | |
| TA | 235 | 44.0±2.3 | 60.1±3.5 | | |
| CG | 24 | 61.3±3.1 | 46.8±3.0 | | |

Vapp=160mV, #exp = 3

| | | | | | |
|---|---|---|---|---|---|
| TACG | 61 | 33.3±0.8 | 51.5±1.8 | 38.9±1.4 | 49.3±2.6 |
| TAC | 110 | 33.2±1.7 | 51.7±1.6 | 39.3±2.1 | |
| ACG | 17 | 53.9±2.7 | 38.8±1.6 | 49.8±2.2 | |
| TA | 90 | 33.8±2.9 | 50.0±1.9 | | |
| CG | 19 | 52.5±2.7 | 38.6±3.5 | | |

Vapp=140mV, #exp = 3

| | | | | | |
|---|---|---|---|---|---|
| TACG | 29 | 22.3±7.6 | 38.6±13.2 | 27.6±9.4 | 34.7±12.0 |
| TAC | 54 | 20.5±8.3 | 34.6±14.2 | 25.7±10.5 | |
| ACG | 5 | 21.4±30.1 | 14.6±20.5 | 17.6±24.7 | |
| TA | 30 | 23.2±9.1 | 36.3±13.9 | | |
| CG | 11 | 30.2±20.6 | 20.9±14.3 | | |

*Fig.11.*

DNA 3' CACTG 5' *SEQ ID NO: 3*

Vapp=180mV, #exp = 3

| Associated base | N | Level Residual Currents (pA) Level order: First | Second | Third | Fourth | Fifth |
|---|---|---|---|---|---|---|
| GTCAC | 160 | 61.1±5.1 | 41.7±4.4 | 49.6±4.7 | 62.5±5.6 | 48.8±4.7 |
| GTCA | 140 | 61.4±1.6 | 42.4±3.0 | 49.9±2.6 | 62.0±2.9 | |
| TCAC | 32 | 40.1±10.8 | 47.0±12.6 | 59.2±15.7 | 46.6±12.5 | |
| GCAC | 1227 | 61.4±1.7 | 46.4±1.8 | 62.5±2.1 | 48.6±1.9 | |
| GTAC | 1206 | 61.5±1.6 | 45.9±2.1 | 62.6±2.1 | 49.0±2.1 | |

Vapp=160mV, #exp = 3

| Associated base | N | First | Second | Third | Fourth | Fifth |
|---|---|---|---|---|---|---|
| GTCAC | 127 | 48.7±4.5 | 31.9±3.5 | 38.2±3.8 | 50.1±4.9 | 38.3±3.9 |
| GTCA | 50 | 48.5±7.0 | 31.8±5.0 | 38.3±5.8 | 49.7±7.5 | |
| TCAC | 15 | 27.2±14.2 | 31.8±16.6 | 41.1±21.3 | 31.6±16.4 | |
| GCAC | 694 | 49.3±1.3 | 35.7±1.7 | 50.6±1.7 | 38.2±1.8 | |
| GTAC | 153 | 49.3±1.2 | 35.2±1.6 | 50.6±1.9 | 38.2±1.8 | |

Vapp=140mV, #exp = 3

| Associated base | N | First | Second | Third | Fourth | Fifth |
|---|---|---|---|---|---|---|
| GTCAC | 112 | 38.2±0.6 | 23.4±0.8 | 28.9±0.7 | 39.8±1.9 | 29.2±1.5 |
| GTCA | 27 | 36.0±7.6 | 22.7±4.7 | 28.3±5.8 | 37.8±7.9 | |
| TCAC | 30 | 22.1±6.1 | 27.2±7.5 | 37.1±10.2 | 27.5±7.6 | |
| GCAC | 142 | 38.0±3.4 | 26.1±2.5 | 39.6±3.9 | 28.9±2.9 | |
| GTAC | 145 | 37.9±3.4 | 25.7±2.5 | 39.5±3.9 | 28.9±2.9 | |

*Fig. 12.*

SEQUENCE LISTING

```
<160> NUMBER OF SEQ ID NOS: 55

<210> SEQ ID NO 1
<211> LENGTH: 4
<212> TYPE: DNA
<213> ORGANISM: Artificial Sequence
<220> FEATURE:
<223> OTHER INFORMATION: Synthetic

<400> SEQUENCE: 1

atgc                                                                    4


<210> SEQ ID NO 2
<211> LENGTH: 4
<212> TYPE: DNA
<213> ORGANISM: Artificial Sequence
<220> FEATURE:
<223> OTHER INFORMATION: Synthetic

<400> SEQUENCE: 2

tacg                                                                    4


<210> SEQ ID NO 3
<211> LENGTH: 5
```

<212> TYPE: DNA
<213> ORGANISM: Artificial Sequence
<220> FEATURE:
<223> OTHER INFORMATION: Synthetic

<400> SEQUENCE: 3 gtcac 5

<210> SEQ ID NO 4
<211> LENGTH: 84
<212> TYPE: DNA
<213> ORGANISM: Artificial Sequence
<220> FEATURE:
<223> OTHER INFORMATION: Synthetic

<400> SEQUENCE: 4
gctggctctg ttgctctctc gcaacagagc cagcaaaaaa aaaaaaaaaa aaaaaaaaaa 60
aaaaaaaaaa aaaaaaaaaa aaaa 84

<210> SEQ ID NO 5
<211> LENGTH: 100
<212> TYPE: DNA
<213> ORGANISM: Artificial Sequence
<220> FEATURE:
<223> OTHER INFORMATION: Synthetic

<400> SEQUENCE: 5
gcaacagagc cagccccgca acagagccag cggagcaaca gagccagctt tgcaacagag 60
ccagcaaaaa aaaaaaaaaa aaaaaaaaaa aaaaaaaaaa 100

<210> SEQ ID NO 6
<211> LENGTH: 100
<212> TYPE: DNA
<213> ORGANISM: Artificial Sequence
<220> FEATURE:
<223> OTHER INFORMATION: Synthetic

<400> SEQUENCE: 6
gcaacagagc cagcggagca acagagccag ccccgcaaca gagccagcaa agcaacagag 60
ccagctttaa aaaaaaaaaa aaaaaaaaaa aaaaaaaaaa 100

<210> SEQ ID NO 7
<211> LENGTH: 100
<212> TYPE: DNA
<213> ORGANISM: Artificial Sequence
<220> FEATURE:
<223> OTHER INFORMATION: Synthetic

<400> SEQUENCE: 7
gcaacagagc cagccccgca acagagccag caaagcaaca gagccagccc cgcaacagag 60
ccagctttgc aacagagcca gcggaaaaaa aaaaaaaaaa 100

<210> SEQ ID NO 8
<211> LENGTH: 14
<212> TYPE: DNA
<213> ORGANISM: Artificial Sequence
<220> FEATURE:
<223> OTHER INFORMATION: Synthetic

<400> SEQUENCE: 8
gctggctctg ttgc 14

<210> SEQ ID NO 9

<211> LENGTH: 180
<212> TYPE: DNA
<213> ORGANISM: Artificial Sequence
<220> FEATURE:
<223> OTHER INFORMATION: Synthetic

<400> SEQUENCE: 9
gctggctctg ttgctctctc gcaacagagc cagccccgct ggctctgttg ctctctcgca 60
acagagccag cggagctggc tctgttgctc tctcgcaaca gagccagctt tgctggctct 120
gttgctctct cgcaacagag ccagcaaaaa aaaaaaaaaa aaaaaaaaaa aaaaaaaaaa 180

<210> SEQ ID NO 10
<211> LENGTH: 50
<212> TYPE: DNA
<213> ORGANISM: Artificial Sequence
<220> FEATURE:
<223> OTHER INFORMATION: Synthetic

<400> SEQUENCE: 10
aaaaaaaaaa aaaaaaaaaa aaaaaaaaaa aaaaaaaaaa aaaaaaaaaa 50

<210> SEQ ID NO 11
<211> LENGTH: 50
<212> TYPE: DNA
<213> ORGANISM: Artificial Sequence
<220> FEATURE:
<223> OTHER INFORMATION: Synthetic

<400> SEQUENCE: 11
cccccccccc cccccccccc cccccccccc cccccccccc cccccccccc 50

<210> SEQ ID NO 12
<211> LENGTH: 50
<212> TYPE: DNA
<213> ORGANISM: Artificial Sequence
<220> FEATURE:
<223> OTHER INFORMATION: Synthetic

<400> SEQUENCE: 12
tttttttttt tttttttttt tttttttttt tttttttttt tttttttttt 50

<210> SEQ ID NO 13
<211> LENGTH: 47
<212> TYPE: DNA
<213> ORGANISM: Artificial Sequence
<220> FEATURE:
<223> OTHER INFORMATION: Synthetic

<400> SEQUENCE: 13
aaaaaaaaaa aaaaaaaaaa aaaaaaaaaa aaaaaaaaaa aaaaaaa 47

<210> SEQ ID NO 14
<211> LENGTH: 50
<212> TYPE: DNA
<213> ORGANISM: Artificial Sequence
<220> FEATURE:
<223> OTHER INFORMATION: Synthetic

<400> SEQUENCE: 14
gggggggggg gggggggggg gggggggggg gggggggggg gggggggggg 50

<210> SEQ ID NO 15
<211> LENGTH: 50
<212> TYPE: DNA
<213> ORGANISM: Artificial Sequence
<220> FEATURE:
<223> OTHER INFORMATION: Synthetic

<400> SEQUENCE: 15
caaaaaaaaa aaaaaaaaaa aaaaaaaaaa aaaaaaaaaa aaaaaaaaaa 50

<210> SEQ ID NO 16
<211> LENGTH: 50
<212> TYPE: DNA
<213> ORGANISM: Artificial Sequence
<220> FEATURE:
<223> OTHER INFORMATION: Synthetic

<400> SEQUENCE: 16
acaaaaaaaa aaaaaaaaaa aaaaaaaaaa aaaaaaaaaa aaaaaaaaaa 50

<210> SEQ ID NO 17
<211> LENGTH: 50
<212> TYPE: DNA
<213> ORGANISM: Artificial Sequence
<220> FEATURE:
<223> OTHER INFORMATION: Synthetic

<400> SEQUENCE: 17
aacaaaaaaa aaaaaaaaaa aaaaaaaaaa aaaaaaaaaa aaaaaaaaaa 50

<210> SEQ ID NO 18
<211> LENGTH: 50
<212> TYPE: DNA
<213> ORGANISM: Artificial Sequence
<220> FEATURE:
<223> OTHER INFORMATION: Synthetic

<400> SEQUENCE: 18
accaaaaaaa aaaaaaaaaa aaaaaaaaaa aaaaaaaaaa aaaaaaaaaa 50

<210> SEQ ID NO 19
<211> LENGTH: 50
<212> TYPE: DNA
<213> ORGANISM: Artificial Sequence
<220> FEATURE:
<223> OTHER INFORMATION: Synthetic

<400> SEQUENCE: 19
cacaaaaaaa aaaaaaaaaa aaaaaaaaaa aaaaaaaaaa aaaaaaaaaa 50

<210> SEQ ID NO 20
<211> LENGTH: 50
<212> TYPE: DNA
<213> ORGANISM: Artificial Sequence
<220> FEATURE:
<223> OTHER INFORMATION: Synthetic

<400> SEQUENCE: 20
ccaaaaaaaa aaaaaaaaaa aaaaaaaaaa aaaaaaaaaa aaaaaaaaaa 50

<210> SEQ ID NO 21
<211> LENGTH: 50
<212> TYPE: DNA
<213> ORGANISM: Artificial Sequence
<220> FEATURE:
<223> OTHER INFORMATION: Synthetic

<400> SEQUENCE: 21
taaaaaaaaa aaaaaaaaaa aaaaaaaaaa aaaaaaaaaa aaaaaaaaaa 50

<210> SEQ ID NO 22
<211> LENGTH: 50
<212> TYPE: DNA
<213> ORGANISM: Artificial Sequence
<220> FEATURE:
<223> OTHER INFORMATION: Synthetic

<400> SEQUENCE: 22
ataaaaaaaa aaaaaaaaaa aaaaaaaaaa aaaaaaaaaa aaaaaaaaaa 50

<210> SEQ ID NO 23
<211> LENGTH: 50
<212> TYPE: DNA
<213> ORGANISM: Artificial Sequence
<220> FEATURE:
<223> OTHER INFORMATION: Synthetic

<400> SEQUENCE: 23
aataaaaaaa aaaaaaaaaa aaaaaaaaaa aaaaaaaaaa aaaaaaaaaa 50

<210> SEQ ID NO 24
<211> LENGTH: 50
<212> TYPE: DNA
<213> ORGANISM: Artificial Sequence
<220> FEATURE:
<223> OTHER INFORMATION: Synthetic

<400> SEQUENCE: 24
attttttttt tttttttttt tttttttttt tttttttttt tttttttttt 50

<210> SEQ ID NO 25
<211> LENGTH: 50
<212> TYPE: DNA
<213> ORGANISM: Artificial Sequence
<220> FEATURE:
<223> OTHER INFORMATION: Synthetic

<400> SEQUENCE: 25
tatttttttt tttttttttt tttttttttt tttttttttt tttttttttt 50

<210> SEQ ID NO 26
<211> LENGTH: 50
<212> TYPE: DNA
<213> ORGANISM: Artificial Sequence
<220> FEATURE:
<223> OTHER INFORMATION: Synthetic

<400> SEQUENCE: 26
ttattttttt tttttttttt tttttttttt tttttttttt tttttttttt 50

<210> SEQ ID NO 27
<211> LENGTH: 50
<212> TYPE: DNA
<213> ORGANISM: Artificial Sequence
<220> FEATURE:
<223> OTHER INFORMATION: Synthetic

<400> SEQUENCE: 27
gggaaaaaaa aaaaaaaaaa aaaaaaaaaa aaaaaaaaaa aaaaaaaaaa 50

<210> SEQ ID NO 28
<211> LENGTH: 50
<212> TYPE: DNA
<213> ORGANISM: Artificial Sequence
<220> FEATURE:
<223> OTHER INFORMATION: Synthetic

<400> SEQUENCE: 28
ccccaaaaaa aaaaaaaaaa aaaaaaaaaa aaaaaaaaaa aaaaaaaaaa 50

<210> SEQ ID NO 29
<211> LENGTH: 50
<212> TYPE: DNA
<213> ORGANISM: Artificial Sequence
<220> FEATURE:
<223> OTHER INFORMATION: Synthetic

<400> SEQUENCE: 29
aaaccccaaa aaaaaaaaaa aaaaaaaaaa aaaaaaaaaa aaaaaaaaaa 50

<210> SEQ ID NO 30
<211> LENGTH: 50
<212> TYPE: DNA
<213> ORGANISM: Artificial Sequence
<220> FEATURE:
<223> OTHER INFORMATION: Synthetic

<400> SEQUENCE: 30
aaaaaacccc aaaaaaaaaa aaaaaaaaaa aaaaaaaaaa aaaaaaaaaa 50

<210> SEQ ID NO 31
<211> LENGTH: 50
<212> TYPE: DNA
<213> ORGANISM: Artificial Sequence
<220> FEATURE:
<223> OTHER INFORMATION: Synthetic

<400> SEQUENCE: 31
aaatacgcat acatcctaag aactcagact acctcccaat aaatccacac 50

<210> SEQ ID NO 32
<211> LENGTH: 50
<212> TYPE: DNA
<213> ORGANISM: Artificial Sequence
<220> FEATURE:
<223> OTHER INFORMATION: Synthetic

<400> SEQUENCE: 32
aaatcagact acctcccaat aaatccgcag caatcctcac acctaataat 50

<210> SEQ ID NO 33
<211> LENGTH: 50
<212> TYPE: DNA
<213> ORGANISM: Artificial Sequence
<220> FEATURE:
<223> OTHER INFORMATION: Synthetic

<400> SEQUENCE: 33
ccctacgcat acatcctaag aactcagact acctcccaat aaatccacac 50

<210> SEQ ID NO 34
<211> LENGTH: 50
<212> TYPE: DNA
<213> ORGANISM: Artificial Sequence
<220> FEATURE:
<223> OTHER INFORMATION: Synthetic

<400> SEQUENCE: 34
ccctcagact acctcccaat aaatccgcag caatcctcac acctaataat 50

<210> SEQ ID NO 35

<211> LENGTH: 50
<212> TYPE: DNA
<213> ORGANISM: Artificial Sequence
<220> FEATURE:
<223> OTHER INFORMATION: Synthetic

<400> SEQUENCE: 35
caaaaaaaaa aaaaaaaaaa aaaaaaaaaa aaaaaaaaaa aaaaaaaaaa 50

<210> SEQ ID NO 36
<211> LENGTH: 50
<212> TYPE: DNA
<213> ORGANISM: Artificial Sequence
<220> FEATURE:
<223> OTHER INFORMATION: Synthetic

<400> SEQUENCE: 36
acaaaaaaaa aaaaaaaaaa aaaaaaaaaa aaaaaaaaaa aaaaaaaaaa 50

<210> SEQ ID NO 37
<211> LENGTH: 50
<212> TYPE: DNA
<213> ORGANISM: Artificial Sequence
<220> FEATURE:
<223> OTHER INFORMATION: Synthetic

<400> SEQUENCE: 37
accccccccc cccccccccc cccccccccc cccccccccc cccccccccc 50

<210> SEQ ID NO 38
<211> LENGTH: 50
<212> TYPE: DNA
<213> ORGANISM: Artificial Sequence
<220> FEATURE:
<223> OTHER INFORMATION: Synthetic

<400> SEQUENCE: 38
cacccccccc cccccccccc cccccccccc cccccccccc cccccccccc 50

<210> SEQ ID NO 39
<211> LENGTH: 50
<212> TYPE: DNA
<213> ORGANISM: Artificial Sequence
<220> FEATURE:
<223> OTHER INFORMATION: Synthetic

<400> SEQUENCE: 39
taaaaaaaaa aaaaaaaaaa aaaaaaaaaa aaaaaaaaaa aaaaaaaaaa 50

<210> SEQ ID NO 40
<211> LENGTH: 50
<212> TYPE: DNA
<213> ORGANISM: Artificial Sequence
<220> FEATURE:
<223> OTHER INFORMATION: Synthetic

<400> SEQUENCE: 40
ataaaaaaaa aaaaaaaaaa aaaaaaaaaa aaaaaaaaaa aaaaaaaaaa 50

<210> SEQ ID NO 41
<211> LENGTH: 50
<212> TYPE: DNA
<213> ORGANISM: Artificial Sequence
<220> FEATURE:
<223> OTHER INFORMATION: Synthetic

<400> SEQUENCE: 41
attttttttt tttttttttt tttttttttt tttttttttt tttttttttt 50

<210> SEQ ID NO 42
<211> LENGTH: 50
<212> TYPE: DNA
<213> ORGANISM: Artificial Sequence
<220> FEATURE:
<223> OTHER INFORMATION: Synthetic

<400> SEQUENCE: 42 tattttttttt tttttttttt tttttttttt tttttttttt tttttttttt 50

<210> SEQ ID NO 43
<211> LENGTH: 50
<212> TYPE: DNA
<213> ORGANISM: Artificial Sequence
<220> FEATURE:
<223> OTHER INFORMATION: Synthetic

<400> SEQUENCE: 43
gaaaaaaaaa aaaaaaaaaa aaaaaaaaaa aaaaaaaaaa aaaaaaaaaa 50

<210> SEQ ID NO 44
<211> LENGTH: 50
<212> TYPE: DNA
<213> ORGANISM: Artificial Sequence
<220> FEATURE:
<223> OTHER INFORMATION: Synthetic

<400> SEQUENCE: 44
agaaaaaaaa aaaaaaaaaa aaaaaaaaaa aaaaaaaaaa aaaaaaaaaa 50

<210> SEQ ID NO 45
<211> LENGTH: 50
<212> TYPE: DNA
<213> ORGANISM: Artificial Sequence
<220> FEATURE:
<223> OTHER INFORMATION: Synthetic

<400> SEQUENCE: 45
aagaaaaaaa aaaaaaaaaa aaaaaaaaaa aaaaaaaaaa aaaaaaaaaa 50

<210> SEQ ID NO 46
<211> LENGTH: 84
<212> TYPE: DNA
<213> ORGANISM: Artificial Sequence
<220> FEATURE:
<223> OTHER INFORMATION: Synthetic

<400> SEQUENCE: 46
tctggctctg ttgctctctc gcaacagagc cagaaaaaaa aaaaaaaaaa aaaaaaaaaa 60
aaaaaaaaaa aaaaaaaaaa aaaa 84

<210> SEQ ID NO 47
<211> LENGTH: 84
<212> TYPE: DNA
<213> ORGANISM: Artificial Sequence
<220> FEATURE:
<223> OTHER INFORMATION: Synthetic

<400> SEQUENCE: 47
cctggctctg ttgctctctc gcaacagagc caggaaaaaa aaaaaaaaaa aaaaaaaaaa 60
aaaaaaaaaa aaaaaaaaaa aaaa 84

<210> SEQ ID NO 48
<211> LENGTH: 84
<212> TYPE: DNA
<213> ORGANISM: Artificial Sequence
<220> FEATURE:
<223> OTHER INFORMATION: Synthetic

<400> SEQUENCE: 48
actggctctg ttgctctctc gcaacagagc cagtaaaaaa aaaaaaaaaa aaaaaaaaaa 60
aaaaaaaaaa aaaaaaaaaa aaaa 84

<210> SEQ ID NO 49
<211> LENGTH: 84
<212> TYPE: DNA
<213> ORGANISM: Artificial Sequence
<220> FEATURE:
<223> OTHER INFORMATION: Synthetic

<400> SEQUENCE: 49
gccggctctg gtgctctctc gcaccagagc cggcaaaaaa aaaaaaaaaa aaaaaaaaaa 60
aaaaaaaaaa aaaaaaaaaa aaaa 84

<210> SEQ ID NO 50
<211> LENGTH: 80
<212> TYPE: DNA
<213> ORGANISM: Artificial Sequence
<220> FEATURE:
<223> OTHER INFORMATION: Synthetic

<400> SEQUENCE: 50
gctgtctgtt gctctctcgc aacagacagc aaaaaaaaaa aaaaaaaaaa aaaaaaaaaa 60
aaaaaaaaaa aaaaaaaaaa 80

<210> SEQ ID NO 51
<211> LENGTH: 76
<212> TYPE: DNA
<213> ORGANISM: Artificial Sequence
<220> FEATURE:
<223> OTHER INFORMATION: Synthetic

<400> SEQUENCE: 51
gctctgttgc tctctcgcaa cagagcaaaa aaaaaaaaaa aaaaaaaaaa aaaaaaaaaa 60
aaaaaaaaaa aaaaaa 76

<210> SEQ ID NO 52
<211> LENGTH: 72
<212> TYPE: DNA
<213> ORGANISM: Artificial Sequence
<220> FEATURE:
<223> OTHER INFORMATION: Synthetic

<400> SEQUENCE: 52
gctgttgctc tctcgcaaca gcaaaaaaaa aaaaaaaaaa aaaaaaaaaa aaaaaaaaaa 60
aaaaaaaaaa aa 72

<210> SEQ ID NO 53
<211> LENGTH: 100
<212> TYPE: DNA
<213> ORGANISM: Artificial Sequence
<220> FEATURE:
<223> OTHER INFORMATION: Synthetic

<400> SEQUENCE: 53

-continued

```
aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa                          100


<210> SEQ ID NO 54
<211> LENGTH: 50
<212> TYPE: DNA
<213> ORGANISM: Artificial Sequence
<220> FEATURE:
<223> OTHER INFORMATION: Synthetic

<400> SEQUENCE: 54

gggaaaaaaa aaaaaaaaaa aaaaaaaaaa aaaaaaaaaa aaaaaaaaaa               50


<210> SEQ ID NO 55
<211> LENGTH: 4
<212> TYPE: DNA
<213> ORGANISM: Artificial Sequence
<220> FEATURE:
<223> OTHER INFORMATION: Synthetic

<400> SEQUENCE: 55

cccc                                                                   4
```

ANALYTE SEQUENCING WITH NANOPORES

CROSS-REFERENCES TO RELATED APPLICATIONS

This is a division of U.S. application Ser. No. 13/592,077, filed Aug. 22, 2012, which is a continuation of International Application No. PCT/US2011/025963, filed Feb. 23, 2011, which claims the benefit of U.S. Provisional Application No. 61/307,441, filed Feb. 23, 2010, and U.S. Provisional Application No. 61/375,707, filed Aug. 20, 2010, each of which is incorporated herein by reference in its entirety.

STATEMENT OF GOVERNMENT LICENSE RIGHTS

This invention was made with Government support under Grant Numbers 5R21HG004145 and R01H6005115, each awarded by the National Institutes of Health. The Government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is 57849_SEQ Final.txt. The text file is 12 KB; was created on Feb. 14, 2017, and is being submitted via EFS-Web with the filing of the specification.

BACKGROUND

The information encoded in DNA is of paramount importance to medicine and to the life sciences. The mapping of the human genome is revolutionizing the understanding of genetic disorders and the prediction of disease, and will aid in developing therapies. The ability to sequence DNA quickly and inexpensively is essential to both individualized medicine and to scientific research. The development of new sequencing techniques beyond the original Sanger sequencing is needed to reach these goals. Even more preferred are new sequencing techniques that can be applied to polymers in addition to nucleic acids.

SUMMARY

Accordingly, some embodiments provide a method of sequencing two or more units of an analyte modified with at least a first arresting construct and a second arresting construct, comprising: (a) providing a nanopore positioned between a cis side comprising a first conductive liquid medium and the modified analyte and a trans side comprising a second conductive liquid medium, wherein the nanopore comprises an opening that provides liquid communication between the cis side and the trans side; (b) causing the first arresting construct of the modified analyte to pause the modified analyte upon entering the opening, thereby producing a first ion current level, wherein the first ion current level represents a first unit; (c) altering the first arresting construct of the modified analyte, the alteration allowing the modified analyte to advance toward the trans side; (d) causing the second arresting construct of the modified analyte to pause the modified analyte upon entering the opening, thereby producing a second ion current level representing a second unit; and (e) comparing the first ion current levels and the second ion current level with a known ion current level of a known unit, thereby sequencing two or more units of the analyte.

Also provided is a method of sequencing two or more nucleotides of a nucleic acid, comprising: (a) providing a nucleic acid comprising at least two unknown nucleotides or set of unknown repeat nucleotides each defined as $X_n$, wherein n=1-1,000,000 and wherein each X and each n may be the same or different; placing a first insert arresting construct and a second insert arresting construct in the nucleic acid, each comprising a duplex nucleic acid and each adjacent to an $X_n$, to provide a modified nucleic acid; (c) providing a mutant MspA porin positioned between a cis side comprising a first conductive liquid medium and the modified nucleic acid and a trans side comprising a second conductive liquid medium; (d) causing a first insert arresting construct to pause the modified nucleic acid upon entering a tunnel of the mutant MspA porin, thereby producing a first ion current level, wherein the first ion current level represents a first $X_n$; (e) altering the first insert arresting construct, the alteration allowing the modified nucleic acid to advance toward the trans side; (f) causing the second insert arresting construct of the modified nucleic acid to pause upon entering the opening, thereby producing a second ion current level representing a second $X_n$; and (g) comparing the first ion current level and the second ion current level with an ion current level of a known $X_n$, thereby sequencing two or more nucleotides of the nucleic acid.

Also provided is a method of correlating an ion current level with a known unit of an analyte, comprising: (a) providing a nanopore positioned between a cis side comprising a first conductive liquid medium and an analyte modified with two or more arresting constructs and containing all known units of interest, and a trans side comprising a second conductive liquid medium, wherein the nanopore comprises an opening that provides liquid communication between the cis side and the trans side; (b) causing a first arresting construct of the modified analyte to pause the modified analyte upon entering the opening, thereby producing an ion current level, wherein the ion current level represents a first known unit of the analyte; (c) altering the first arresting construct of the modified analyte, the alteration allowing the modified analyte to advance toward the trans side; (d) causing the second arresting construct of the modified analyte to pause the modified analyte upon entering the opening, thereby producing a second ion current level representing a second unit; and (e) calibrating the nanopore with a known modified analyte containing all units and corresponding ion current levels of interest and optionally obtaining a separator level, thereby correlating each ion current level with a known unit of an analyte.

Further provided is a method of slowing or stepping the rate that a modified analyte translocates through an opening of a nanopore, comprising: (a) providing a nanopore positioned between a cis side comprising a first conductive liquid medium and a modified analyte and a trans side comprising a second conductive liquid medium; (b) causing an arresting construct of the modified analyte to pause the modified analyte upon entering the opening, thereby producing one or more ion current levels, wherein each ion current level is distinguishable; and (c) altering at least a first arresting construct of the modified analyte, the alteration allowing the modified analyte to advance toward the trans side; wherein the modified analyte has an average translocation velocity through the opening that is less than the average translocation velocity at which the analyte translocates through the tunnel in the absence of modification and alteration.

Systems are also provided herein, such as a system comprising a nanopore having an opening, wherein the nanopore is positioned between a first conductive liquid medium and a second conductive liquid medium, wherein at least one liquid medium comprises a modified analyte defined as a modified nucleic acid.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 2A: The positive voltage attracts the negatively charged hairpin DNA into the pore. FIG. 2B: The DNA threads through the pore until the wider hairpin duplex prevents further translocation. FIG. 2C: After a few milliseconds the hairpin dissociates allowing for complete translocation. FIG. 2D: The resulting current trace associated with the above cartoon shows that the hairpin DNA present in the pore allows a residual current, $I_{res}$, until the hairpin duplex dissociates.

FIG. 4A: For comparison purposes, FIG. 4A summarizes the averaged Gaussian mean and width of $I_{res}$ of the homopolymer hairpin tails at 180 mV (with fit values described below in the examples). The separate effects on $I_{res}$ due to dA, dG, dC, and dT, are indicated respectively. The residual current markedly changes with the position, x, of a single nucleotide dNx, within an otherwise poly-dA homopolymer hairpin (hp) tail. FIG. 4B: When the nucleotide substitution is adjacent to the double stranded terminus, x=1, the residual current deviates to resemble the hompolymer values associated with the substituted nucleotide. The $dT_1$ substitution most closely resembles kr. FIG. 4C: At x=2, the nucleotide substitution also causes residual current is closer to the homopolymer associated with the substituted nucleotide. The $dC_2$ substitution is closest to Idc. FIG. 4D: With any substitution at x=3, $I_{res}$ is only slightly different from $I_{dA}$, suggesting that MspA is primarily sensitive to the two nt after the hairpin duplex. A $dG_x$ substitution at x=1,2, or 3, does not significantly influence the current, as may be expected given the relative closeness of $I_{dG}$ and $I_{dA}$.

FIGS. 10-12 are described above in the legend for FIGS. 5A, 5B, and 5C and in the examples below.

DETAILED DESCRIPTION

Figure 1:
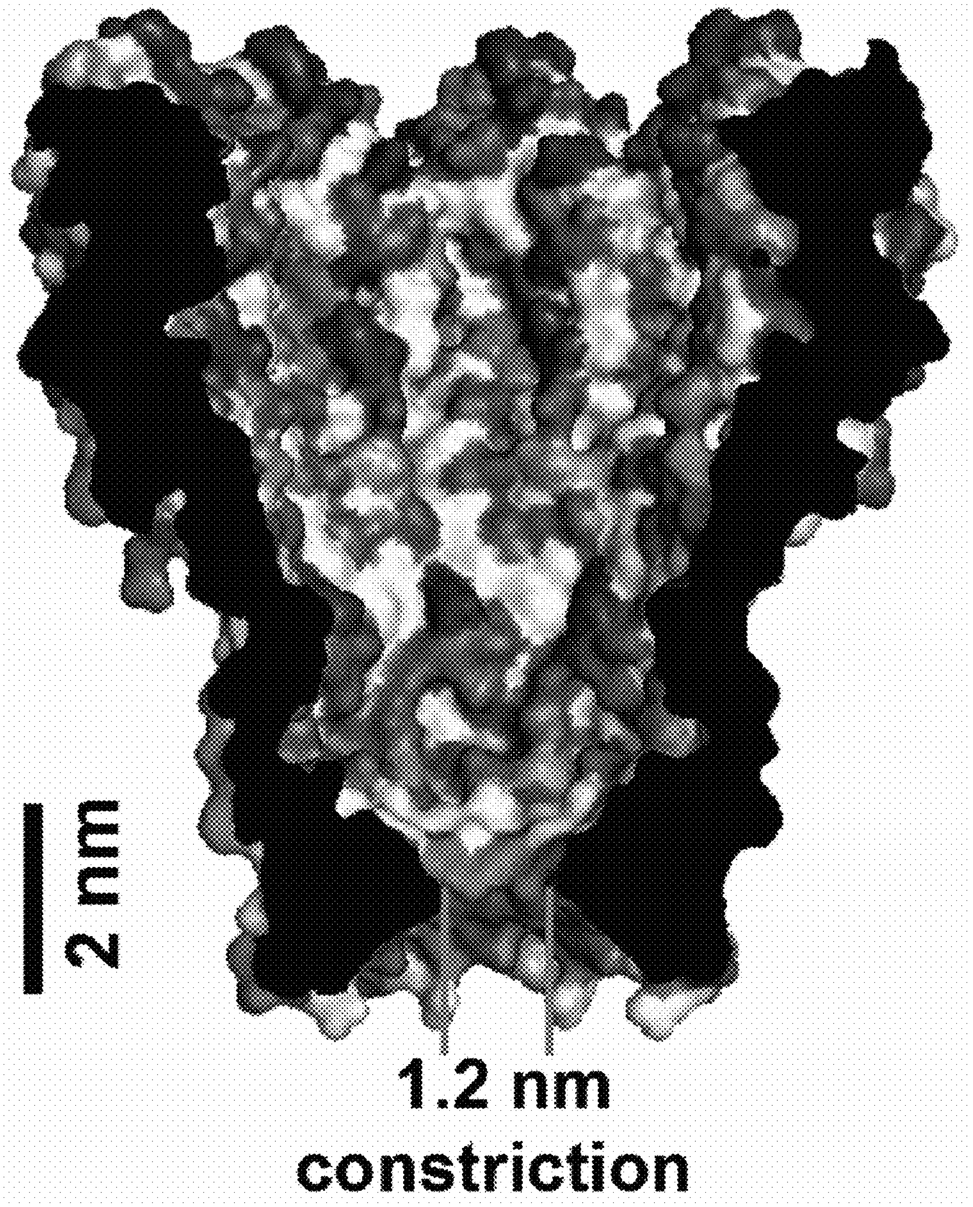
FIG. 1 depicts the crystal structure of an MspA. The cross-sectional view through M1-NNN-MspA's structure using a space-filling model displays the classes of amino acids: positively charged; negatively charged; polar; hydrophobic-aliphatic; hydrophobic-aromatic. See Science 303: 1189 (2004).
Figures 2A, 2B, 2C, 2D:
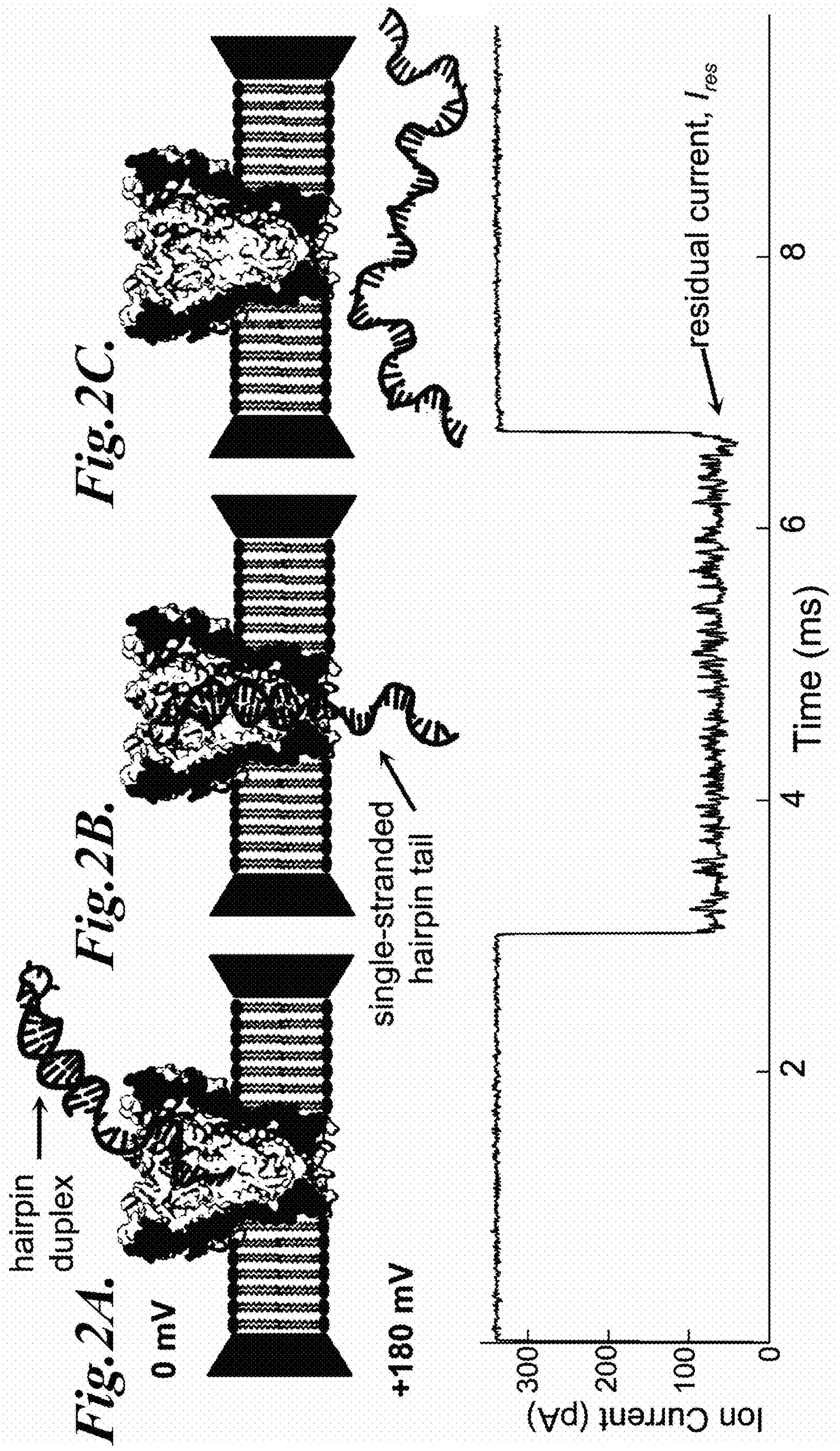
FIGS. 2A, 2B, 2C, and 2D depict DNA translocation through the nanopore MspA. The cartoon depicts DNA translocation through MspA and the resulting residual current.

Provided herein are methods and systems for sequencing units of an analyte. In general, sequencing may take places as follows. In the native state, units of the analyte are able to translocate through an opening of a nanopore. The translocation of the analyte through the pore may be too fast to resolve the composition of the units of the analyte. Arresting constructs are used to modify the analyte such that the modified analyte is no longer able to fit through the opening. Each arresting construct allows the modified analyte to pause in the opening such that an ion current level may be detected and associated with a particular unit. The arresting construct may then be altered to provide a modified analyte that is now able to advance through the opening. The modified analyte comprises at least a second arresting construct that causes a second pause of the modified analyte in the opening such that a next ion current level may be detected that is associated with a next unit. Alteration of the second arresting construct allows the modified analyte to again advance through the opening. The process may be repeated for as many arresting constructs as there are in the modified analyte such that each unit of the analyte is sequenced.

Accordingly, some embodiments provide a method of sequencing two or more units of an analyte modified with at least a first arresting construct and a second arresting construct, comprising: (a) providing a nanopore positioned between a cis side comprising a first conductive liquid medium and the modified analyte and a trans side comprising a second conductive liquid medium, wherein the nanopore comprises an opening that provides liquid communication between the cis side and the trans side; (b) causing the first arresting construct of the modified analyte to pause the modified analyte upon entering the opening, thereby producing a first ion current level, wherein the first ion current level represents a first unit, which may be the first unit in the modified analyte; (c) altering the first arresting construct of the modified analyte, the alteration allowing the modified analyte to advance toward the trans side; (d) causing the second arresting construct of the modified analyte to pause the modified analyte upon entering the opening, thereby producing a second ion current level representing a second unit; and (e) comparing the first ion current levels and the second ion current level with a known ion current level of a known unit, thereby sequencing two or more units of the analyte. This or any other method herein may be repeated as needed to sequence a third, fourth, fifth, etc., unit in the modified analyte through use of a third, fourth, fifth, etc, arresting construct in the modified analyte.

In some embodiments, the modified analyte comprises a modified nucleic acid, a modified peptide, or a modified protein. In some embodiments, the modified analyte comprises a modified nucleic acid. In some embodiments, the modified nucleic acid comprises a modified DNA, a modified RNA, a modified PNA, or a combination thereof. In some embodiments, the modified analyte comprises a linker joining the analyte to an arresting construct. The modified analyte may be further defined as a modified nucleic acid comprising a linker joining the nucleic acid to an arresting construct. In some embodiments, the modified analyte comprises an inorganic moiety having a molecular weight of 1 MDa or less. In other embodiments, the modified analyte comprises an organic moiety having a molecular weight of 1 MDa or less.

Optionally, at least one arresting construct is an insert arresting construct. In some embodiments, the insert arresting construct is a duplex nucleic acid. In other embodiments, at least one arresting construct is a pendant arresting construct. Each arresting construct may be identical or different. In some embodiments, two or more of the arresting constructs are different. In some embodiments, the modified analyte comprises a translocation initiation tail. Optionally, the modified analyte is a ssDNA modified with at least two insert arresting constructs each further defined as a duplex DNA, where each duplex may be the same or different, and wherein each unit is a single nucleotide (e.g., C) or a repeat nucleotide (e.g., CCC).

Methods disclosed herein may be used to identify repeat units in an analyte, such as repeat nucleotides. In some embodiments, one arresting construct pauses the modified analyte to allow the ion current level to determine the identity of a unit and another arresting construct pauses the modified analyte to produce an ion current level that differs from any unit-specific ion current level and is defined as a separator level. In some embodiments, the separator level distinguishes sequential units of the analyte. In some embodiments, the separator level distinguishes sequential and repeated units of the analyte. In some embodiments, periodically the separator level is designed to produce a different ion current level to provide a checksum. Optionally, at least two separator levels are used to provide a binary code to represent units of the analyte. Optionally, at least one separator level provides a parity bit.

Sequencing fidelity may be improved when one or more modified analytes are sequenced multiple times to produce multiple current patterns allowing averaging and consensus reads.

Application of an electric field may cause the modified analyte to enter the opening or otherwise cause movement of a modified analyte, such as moving a modified analyte through an opening of a nanopore after alteration. In some embodiments, physical pressure causes the modified analyte to enter the opening or otherwise causes movement of a modified analyte. In some embodiments, a magnetic bead is attached to the modified analyte on the trans side, and alteration is caused by a magnetic force causing the modified analyte to enter or proceed through the opening or otherwise causes movement of the modified analyte. For example, the magnetic bead does not fit through the pore, but it can be used once a translocation initiation tail has made it through the pore.

In some embodiments, alteration is caused by a voltage pulse, a voltage ramp, a light pulse, or a mechanical force pulse. Alteration may be further defined as dissociation of the arresting construct. Alteration may be further defined as a conformational change of the arresting construct.

Some methods may further comprise changing the modified analyte velocity as it enters the opening or changing the sequencing sensitivity by adjusting the pH of the first or second conductive liquid medium. Some methods may further comprise changing the modified analyte velocity as it enters the opening or changing the sequencing sensitivity by adjusting the ionic strength of the first or second conductive liquid medium. Some methods may further comprise changing the modified analyte velocity as it enters the opening or changing the sequencing sensitivity by adjusting the ion type of the first or second conductive liquid medium. Some methods may further comprise changing the modified analyte velocity as it enters the opening or changing the sequencing sensitivity by adjusting the temperature of the first or second conductive liquid medium. Some methods may further comprise changing the modified analyte velocity as it enters the opening or changing the sequencing sensitivity by adjusting the viscosity of the first or second conductive liquid medium. Some methods may further comprise changing the modified analyte velocity as it enters the opening or changing the sequencing sensitivity by employing duplex-binding reagents.

Some embodiments further comprise obtaining the modified analyte.

A nanopore may comprise a solid-state material, such as silicon nitride, modified silicon nitride, silicon, silicon oxide, or graphene, or a combination thereof. In some embodiments, a nanopore is protein that forms a tunnel upon insertion into a bilayer, membrane, thin film, or solid-state aperture. In some embodiments, the nanopore is comprised in a lipid bilayer. In some embodiments, the nanopore is comprised in an artificial membrane comprising a mycolic acid. The nanopore may be a *Mycobacterium smegmatis* porin (Msp) porin having a vestibule and a constriction zone that define the tunnel. The Msp porin may be a mutant MspA porin. In some embodiments, amino acids at positions 90, 91, and 93 of the mutant MspA porin are each substituted with asparagine. Some embodiments may comprise altering the modified analyte velocity or sequencing sensitivity by removing, adding, or replacing at least one amino acid of an Msp porin. The nanopore may be α-hemolysin or a variant thereof. Some embodiments may comprise altering the modified analyte velocity or sequencing sensitivity by removing, adding, or replacing at least one amino acid of α-hemolysin or a variant thereof.

Also provided is a method of sequencing two or more nucleotides of a nucleic acid, comprising: (a) providing a nucleic acid comprising at least two unknown nucleotides or set of unknown repeat nucleotides each defined as $X_n$, wherein n=1-1,000,000 and wherein each X and each n may be the same or different; placing a first insert arresting construct and a second insert arresting construct in the nucleic acid, each comprising a duplex nucleic acid and each adjacent to an $X_n$, to provide a modified nucleic acid; (c) providing a mutant MspA porin positioned between a cis side comprising a first conductive liquid medium and the modified nucleic acid and a trans side comprising a second conductive liquid medium; (d) causing a first insert arresting construct to pause the modified nucleic acid upon entering a tunnel of the mutant MspA porin, thereby producing a first ion current level, wherein the first ion current level represents a first $X_n$; (e) altering the first insert arresting construct, the alteration allowing the modified nucleic acid to advance toward the trans side; (f) causing the second insert arresting construct of the modified nucleic acid to pause upon entering the opening, thereby producing a second ion current level representing a second $X_n$; and (g) comparing the first ion current level and the second ion current level with an ion current level of a known $X_n$, thereby sequencing two or more nucleotides of the nucleic acid. In some embodiments, one insert arresting construct pauses the modified nucleic acid to allow the ion current level to determine the identity of a nucleotide and another insert arresting construct pauses the modified nucleic acid to produce an ion current level that differs from any nucleotide-specific ion current level and is defined as a separator level. In some embodiments, the separator level distinguishes sequential nucleotides of the nucleic acid. In some embodiments, the separator level distinguishes sequential and repeated nucleotides of the nucleic acid. In some embodiments, periodically the separator level is designed to produce a different ion current level to provide a checksum. Optionally, at least two separator levels are used to provide a binary code to represent units of the analyte. Optionally, at least one separator level provides a parity bit.

Further provided is a method of correlating an ion current level with a known unit of an analyte, comprising: (a) providing a nanopore positioned between a cis side comprising a first conductive liquid medium and an analyte modified with two or more arresting constructs and containing all known units of interest, and a trans side comprising a second conductive liquid medium, wherein the nanopore comprises an opening that provides liquid communication between the cis side and the trans side; (b) causing a first arresting construct of the modified analyte to pause the modified analyte upon entering the opening, thereby producing an ion current level, wherein the ion current level represents a first known unit of the analyte; (c) altering the first arresting construct of the modified analyte, the alteration allowing the modified analyte to advance toward the trans side; (d) causing the second arresting construct of the modified analyte to pause the modified analyte upon entering the opening, thereby producing a second ion current level representing a second unit; and (e) calibrating the nanopore with a known modified analyte containing all units and corresponding ion current levels of interest and optionally obtaining a separator level, thereby correlating each ion current level with a known unit of an analyte. This or any other method may be repeated to sequence a third, fourth, fifth, etc., known unit in the modified analyte through the use of a third, fourth, fifth, etc., arresting construct. In some embodiments, each arresting construct is the same and in some embodiments, each arresting construct is different.

Further provided is a method of slowing or stepping the rate that a modified analyte translocates through an opening of a nanopore, comprising: (a) providing a nanopore positioned between a cis side comprising a first conductive liquid medium and a modified analyte and a trans side comprising a second conductive liquid medium; (b) causing an arresting construct of the modified analyte to pause the modified analyte upon entering the opening, thereby producing one or more ion current levels, wherein each ion current level is distinguishable; and (c) altering at least a first arresting construct of the modified analyte, the alteration allowing the modified analyte to advance toward the trans side; wherein the modified analyte has an average translocation velocity through the opening that is less than the average translocation velocity at which the analyte translocates through the tunnel in the absence of modification and alteration.

Systems are also provided herein, such as a system comprising a nanopore having an opening, wherein the nanopore is positioned between a first conductive liquid medium and a second conductive liquid medium, wherein at least one liquid medium comprises a modified analyte, such as a modified nucleic acid. In some embodiments, the modified nucleic acid is further defined as a modified DNA and each arresting construct of the modified DNA is a duplex DNA that contains the same number of nucleotides and each duplex DNA is identical. In some embodiments, the system is operative to cause an arresting complex of the modified nucleic acid to dissociate upon entering the opening. A system may be operative to sequence the modified nucleic acid. A nanopore comprised in a system may be comprised in a bilayer, membrane, thin film, or solid-state aperture. In some embodiments, the nanopore is further defined as a *Mycobacterium smegmatis* porin (Msp) porin or α-hemolysin or a variant thereof. Systems may further comprise a patch-clamp amplifier, optical patch clamps, a data acquisition device, or one or more temperature regulating devices in communication with the first liquid medium, the second liquid medium, or any combination thereof. With respect to optical patch claims, the current may be translated to fluorescence that can be read and correlated in a similar fashion as the current.

Systems may be prepared to allow parallel reads in multiple nanopores, such as thousands or millions of nanopores. Accordingly, components of any system may be functionally duplicated to multiply sequencing throughput. Any system may also be adapted with microfluidics or automation.

In some embodiments, ions current levels for units of an analyte, while having to be distinct from each other, do not have to be known a priori. Since current levels may vary from experiment to experiment, one may run a calibration construct first. For example for DNA sequencing, one would run a construct modified analyte which contains all four nucleotides and optionally non standard (modified) nucleotides, such as methylated C (mC). Using methods disclosed herein, each unit of the modified analyte generates a unique and identifying current level (e.g., the amplitude or characteristics of each ion current level is unique to each analyte unit type). Each such current level is maintained until the modified analyte advances one unit. The sequence of the analyte is directly mapped into the record of the ion current.

In some embodiments, a double stranded nucleic acid may be exposed to a first enzyme that selectively nicks at a position of every nth nucleotide of one strand of the nucleic acid to expose every nth nucleotide of the other strand to affect the ion current. The resulting nucleic acid may be considered a modified nucleic acid having a plurality of duplexes, where each duplex is considered an arresting construct. A duplex may be caused to pause upon entering an opening of a nanopore to produce an ion current level, wherein each ion current level represents an exposed nucleotide. A duplex may then be dissociated to provide an altered nucleic acid, which then may advance through the opening until a next duplex pauses movement to allow another ion current level to be detected that is associated with a next unit. Each ion current level may then be compared with a known ion current level of a known nucleotide and a known double stranded termination, thereby sequencing the every nth nucleotide. A second double stranded nucleic acid that is identical to the first may then be exposed to a second (or same) enzyme that selectively nicks a position of every nth nucleotide to expose every nth nucleotide but with a different starting position (nth+i, where i is a constant offset). The same procedure as above may be executed for the second nucleic acid. This procedure may be repeated with at least n nicked nucleic acids (and possibly n/2 nicked nucleic acids since the terminating base pair may also be identified) as needed such that each nucleotide is sequenced.

An "analyte" refers to a molecule having a sequence of two or more units, where each unit may be the same or different. A unit of an analyte is of a size that may be translocated through a nanopore's opening, such that the unit enters one side of the opening and moves through and out of the other side. Typically, an analyte is soluble or partially soluble in at least one conductive liquid medium that is in contact with a nanopore. Non-limiting examples include nucleic acids, peptides, and proteins, as well as a variety of hydrocarbon polymers (e.g., polyethylene, polystyrene) and functionalized hydrocarbon polymers, wherein the backbone of the polymer comprises a carbon chain (e.g., polyvinyl chloride, polymethacrylates). A unit may be a unitary moiety (e.g., a single nucleotide, T) or it may be multiple moieties that are repeats or are varied (e.g., a TTT trinucleotide or a TGC trinucleotide). In some embodiments, an analyte is a nucleic acid having units ranging from 1-1,000,000 nucleotides in length. Analytes also include polymers such as copolymers, block copolymers, and branched polymers such as star polymers and dendrimers. Analytes may comprise nanoparticles. A mixture of analytes may be employed in embodiments herein. An analyte may be modified by an arresting construct to produce a "modified analyte," described below. A modified analyte may be altered, as described herein.

An "arresting construct" is an entity used to modify an analyte such that the modified analyte no longer fits through the opening of a nanopore. Due to one or more properties of the arresting construct (e.g., orientation, size, or charge), the arresting construct causes the modified analyte to pause in the opening of a nanopore during translocation. Arresting constructs may be inserted in between one or more units of an analyte ("insert arresting construct") or may be used to modify the units themselves ("pendant arresting construct"). As such, the arresting construct may be located adjacent to the unit to be sequenced, or it may cover (that is, mask) the unit, as described below. An arresting construct may also replace a unit, where the arresting construct correlates to the unit. Arresting constructs may be single molecules or combinations of molecules (e.g., duplex DNA). An arresting construct may be a protein. An arresting construct may comprise a nanoparticle. As used herein, a "nanoparticle" refers to a particle having one or more dimensions of the order of 100 nm or less. Additional arresting constructs are described below.

The arresting construct is also able to be altered, or alter the opening of a nanopore, or both, such that translocation continues to advance the modified analyte one unit. Alteration may take place by a variety of means. In some embodiments, alteration is induced through the application of a stimulus such as voltage (e.g., voltage pulses or voltage ramps), irradiation (e.g., light pulses), changes in temperature (e.g., temperature pulses), or physical motion (e.g., ultrasound, use of magnetic beads to generate a force pulse). In some embodiments, alteration entails dissociation of part or all of the arresting construct, such as the dissociation of one strand of a double stranded nucleic acid. Alteration may entail a conformational change, such as a change in shape or orientation. A conformational change may entail a chiral inversion. As an example of a conformational change, an arresting construct may be a protein that changes shape upon application of a stimulus. Alteration may entail a change in orientation, such as an orientation change caused by irradiation of the arresting construct. An arresting construct may cause the shape or charge of the opening of a nanopore to change. Conversely, the force provided by an opening of a nanopore may cause alteration of an arresting construct, such as a change in size. An arresting construct may involve any combination of these aspects as well (e.g., the arresting construct may change shape as it also changes the shape of the opening; the force provided by an opening of a nanopore may cause a change in shape and orientation of an arresting construct).

Insert arresting constructs are located adjacent to a unit and consist of paired moieties that may be dissociated from each other or otherwise altered. The insert arresting construct causes the modified analyte to pause in the opening, thereby allowing an ion current level to be detected that is associated with the adjacent unit. After the ion current level has been detected, alteration of the insert arresting construct causes a change (e.g., one of the pairs dissociates) such that the remainder of the modified analyte may advance toward the trans side. Alteration of a next arresting construct allows for generation of a next ion current level that may be detected, and so forth.

Insert arresting constructs may consist of binding pairs that may be dissociated. Binding pairs have an affinity for one another. Non-limiting examples of insert arresting constructs that are binding pairs include nucleic acids, such as duplex nucleic acids (e.g., duplex DNA) that may be inserted in between units of an analyte, such as nucleotide units, to produce a modified analyte. The duplex nucleic acid may cause the modified analyte to pause in an opening of a nanopore due to the size of the duplex, whereupon dissociation causes one strand of the duplex to dissociate such that the remainder of the modified analyte may advance toward the trans side. The duplex nucleic acid may, in some embodiments, contain 1-100 base pairs. An insert arresting construct may be about the same length as a 1-100 base pair duplex nucleic acid. Other known binding pairs that may be employed include single-stranded DNA binding proteins, RNA, PNA, and combinations of RNA, PNA, and DNA. In some embodiments, one or more nucleotides form an insert arresting construct. For example, one or more nucleotides may be inserted in between units of an analyte to provide a modified analyte, and free nucleotides comprised in a liquid medium in contact with the modified analyte may bind to the nucleotides in situ, then later dissociate.

In some embodiments, dielectric elastomers, photomechanical materials, or temperature-responsive polymers may be employed as insert arresting constructs. These classes are well-known in the art. See, e.g., U.S. Pat. Nos. 7,594,359 and 7,625,764, each incorporated herein by reference in its entirety, and J Mech Physics Solids 57:1103 (2009).

In addition to binding pairs, molecules joined by photolytic bonds may also be employed such that irradiation photocleaves one molecule from the other. Such photolytic bonds are well known in the art. Non-limiting examples include psoralens and derivatives, photocleavable dyes used in DNA-sequencing strategies, the chemical compound 1-(4,5-dimethoxy-2-nitro-phenyl)ethyl ester (Photochem Photobio 81:953 (2005)), and photoreactive amino acids, such as L-photo-leucine.

Other insert arresting constructs include peptides, proteins, nanoparticles, and polyelectrolytes (e.g., dextran sulfate and poly(acrylic acid)).

Pendant arresting constructs cover units and consist of pendant moieties that may be altered as described above. Pendant arresting constructs typically modify consecutive units. A pendant arresting construct causes the modified analyte to pause in a nanopore's opening. After alteration of the pendant arresting construct, the unit previously covered by the pendant arresting construct becomes exposed. Because another pendant arresting construct is located adjacent to the now-exposed unit, the now-exposed unit pauses in the opening such that an ion current level may be detected. Alteration of a next pendant arresting construct allows for generation of a next ion current level that may be detected, and so forth.

Non-limiting examples of pendant arresting constructs include the same examples and classes of constructs as insert arresting constructs described above. For example, a pendant arresting construct may, together with a unit of an analyte, form a binding pair. A pendant arresting construct may, together with a unit of an analyte, constitute dielectric elastomers, photomechanical materials, or temperature-responsive polymers. A pendant arresting construct may be joined to the unit by a photolytic bond. A pendant arresting construct may comprise a peptide, protein, nanoparticle, or polyelectrolyte. In some embodiments, a nucleotide is a pendant arresting construct. For example, free nucleotides comprised in a liquid medium in contact with the analyte may bind to a nucleotide unit in situ, then later dissociate.

An analyte modified with an arresting construct provides a "modified analyte." A modified analyte does not proceed with translocation through an opening of a nanopore due to a property of the arresting construct (e.g., orientation, size, or charge) unless the modified analyte is altered. While a modified analyte will typically comprise either insert arresting constructs or pendant arresting constructs, a modified analyte may also comprise both types. Each insert arresting construct may be the same or different within the same modified analyte. Each pendant arresting construct may be the same or different within the same modified analyte.

Modified analytes may be obtained in a variety of ways, including obtaining an analyte and requesting a commercial entity to prepare the modified analyte. DNA modification schemes were initially developed in hopes of sequencing freely translocating DNA that is expanded into many nucleotides of the same type to produce sufficiently long current signatures. This modification is typically accomplished using cyclic application of DNA restriction and ligation enzymes. Meller et al. postulated an optical-nanopore sequencing strategy with each nucleotide converted into a specific binary code made of two 12-mer oligos using such a DNA modification scheme ("New High Throughput Technologies for DNA Sequencing and Genomics," ed K. Mitchelson (Elsevier, Oxford, UK), pp 245-264; Clin Chem 53:1996 (2007); Nano Lett. 10:2237 (2010)). An automated, massively-parallel process (see U.S. Pat. No. 6,723,513 and WO 2006/092582, each incorporated herein by reference in its entirety) requires ~24 h for the conversion of a complete human genome into a DNA mixture consisting of fragments, each corresponding to a 24 bp segment of the original genome (Nat Biotechnol 26:1146 (2008)). For example, LingVitae Corp. (Oslo, Norway) may prepare modified nucleic acids having insert arresting constructs that are duplex nucleic acids of one's choosing. The DNA conversion required for DI sequencing is less demanding because each inserted DNA could be identical and independent of the analyte nucleotides. In comparison to previously proposed sequencing methods involving converted DNA, DI sequencing does not require additional hardware such as fluorescence detection or conversion to binary codes. Work is currently underway to develop inexpensive, low-error conversion of long segments of the original genome with reduced conversion time (Nano Lett 10:2237 (2010)). Further reduction in conversion cost and speed may be attained through massive parallelization, comparable to sequencing-by-ligation technologies that rely on ligation reactions.

A linker may join an arresting construct to an analyte to provide a modified analyte. Generally, a linker is a divalent molecule having no specific activity other than to join an arresting construct to an analyte or to preserve some minimum distance or other spatial relationship between such species. However, a linker may be selected to influence some property of the linked species, such as three-dimensional conformation, net charge, or hydrophobicity. Suitable linkers are known in the art, and include linkers that form bonds between an arresting construct and the analyte selected from covalent bonds (e.g., disulfide or carbon-carbon bonds), hydrogen bonds (e.g., Watson-Crick or Hoogstein base pairing), ionic bonds, or other electrostatically induced bonds.

A "nanopore" refers to a pore having an opening with a diameter at its most narrow point of about 0.3 nm to about 2 nm. For example, a nanopore may be a solid-state nanopore, a graphene nanopore, an elastomer nanopore, or may be a naturally-occurring or recombinant protein that forms a tunnel upon insertion into a bilayer, thin film, membrane (e.g., a membrane disclosed herein), or solid-state aperture, also referred to as a protein pore or protein nanopore herein (e.g., a transmembrane pore). If the protein inserts into the membrane, then the protein is a tunnel-forming protein. Methods of determining whether a protein is a tunnel-forming protein are well-known in the art. For example, one may determine if an Msp porin forms a tunnel by determining whether the protein inserts into a bilayer, such as described in U.S. Provisional Application Ser. No. 61/098,938 and its related PCT application, WO 2010/034018, each of which is incorporated herein by reference in its entirety, and Proc Natl Acad Sci 105:20647 (2008). Typically, tunnel formation is detected by observing a discrete change in conductivity. See, e.g., Mol Microbiol 33:933 (1999). An opening is typically in liquid or gas communication with the cis and trans sides of the membrane or nanopore. A nanopore may comprise a solid state material, such as silicon nitride, modified silicon nitride, silicon, silicon oxide, or graphene, or a combination there of (e.g., a nanopore may be prepared by making first a SiN aperture, putting a sheet of graphene over it, and then making a nanopore in the graphene). Non-limiting examples of protein nanopores include α-hemolysin and variants thereof (defined below), a *Mycobacterium smegmatis* porin (Msp) porin (defined below) or OmpATb.

"the alteration allowing the modified analyte to advance toward the trans side"—This phrase refers to the act of alteration of an arresting construct of a modified analyte that allows the modified analyte to advance towards the trans side such that (a) the entire remainder of the modified analyte may translocate through the opening if no further arresting construct pauses translocation, or (b) another arresting construct encounters the opening and is caused to be altered, thereby allowing another unit of the modified analyte to generate an ion current level.

As a modified analyte interacts with an opening of a nanopore, the current through the opening changes. When an arresting construct temporarily prevents a unit of the modified analyte from translocating through the opening, an ion current level results. That is, ion current levels are correlated to, or represent, units of an analyte. For a DNA analyte with duplex DNA arresting constructs, analyzed with M1-NNN-MspA, simple analysis as described herein revealed average current levels separated by 2 pA and lasting greater than 1.5 ms could identify units of an analyte DNA sequence. Persons of skill in the art are able to establish ion current levels of other analyte units. Ion current levels are typically an average ion current. In some embodiments, the ion current amplitude through the pore may be converted to a fluorescent optical system as is well known in the art. See, e.g., J Amer Chem Soc 13:1652 (2009).

When one arresting construct pauses a modified analyte to allow the ion current level to determine the identity of a unit and another arresting construct pauses the modified analyte to produce an ion current level that differs from any unit-specific ion current level, the latter ion current level is defined as a separator level. A separator level may distinguish sequential units of the analyte. A separator level distinguishes sequential and repeated units of the analyte. A separator level may be designed to produce a different ion current level to provide a checksum. Optionally, at least two separator levels are used to provide a binary code to represent units of the analyte. Optionally, at least one separator level is used to provide constitutes essentially a parity bit.

A translocation initiation tail is any linear charged polymer that may be appended to a modified analyte to initiate translocation through the opening of a nanopore. Thus, the tail must be smaller in diameter than the opening. The tail may be located at either end of a modified analyte or at both ends. Non-limiting examples of tails include polynucleotides such as single stranded DNA. Other tails include nucleic acids (e.g., DNA or RNA) of heteropolymeric, homopolymeric, a-basic, and/or basic residues. In some embodiments, the tail is polyadenine, such as poly-$dA_m$, wherein m ranges from 1-100 [SEQ ID NO:53]. A tail may comprise poly(acrylic acid). Other poly(acids) may include acid groups —COOH, —$SO_3H$, or —$PO_3H_2$. Tails may also include charged poly-L lysine or other charged amino acids.

Duplex binding reagents serve to enhance the formation of a duplex nucleic acid. Such reagents increase the frequency of generating successful duplexes, which, when duplexes are used as arresting constructs, may improve sequencing sensitivity. Non limiting examples include divalent cations such as $Mg^{2+}$, major and minor DNA groove binding proteins and chemicals, interstrand DNA crosslinking reagents, and DNA intercalators.

A "liquid medium" includes aqueous, organic-aqueous, and organic-only liquid media. Organic media include, e.g., methanol, ethanol, dimethylsulfoxide, and mixtures thereof. Liquids employable in methods described herein are well known in the art. Descriptions and examples of such media, including conductive liquid media, are provided in U.S. Pat. No. 7,189,503, for example, which is incorporated herein by reference in its entirety. Salts, detergents, or buffers may be added to such media. Such agents may be employed to alter pH or ionic strength of the liquid medium. Viscosity-altering substances, such as glycerol or various polymers (e.g., polyvinylpyrrolidone, polyethylene glycol, polyvinyl alcohol, cellulose polymers), and mixtures thereof, may be included in liquid media. Methods of measuring viscosity are well known in the art. Any agent that may be added to a liquid medium may also change the velocity of modified analyte being studied. As such, a velocity-altering agent may be a salt, a detergent, a buffer, a viscosity-altering substance, or any other agent added to a liquid medium that increases or decreases the velocity of an analyte or modified analyte.

The first and second liquid media employed in any embodiment may be the same or different, and either one or both may comprise one or more of a salt, a detergent, or a buffer. Indeed, any liquid media described herein may comprise one or more of a salt, a detergent, or a buffer. Optionally, at least one liquid medium is conductive. Optionally, at least one liquid medium is not conductive. The liquid media may comprise any analyte described herein.

As used herein, an "amino acid" refers to any of the 20 naturally occurring amino acids found in proteins, D-stereoisomers of the naturally occurring amino acids (e.g., D-threonine), unnatural amino acids, and chemically modified amino acids. Each of these types of amino acids is not mutually exclusive. α-Amino acids comprise a carbon atom to which is bonded an amino group, a carboxyl group, a hydrogen atom, and a distinctive group referred to as a "side chain." The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine).

The following abbreviations are used for the 20 naturally occurring amino acids: alanine (Ala; A), asparagine (Asn; N), aspartic acid (Asp; D), arginine (Arg; R), cysteine (Cys;

C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Unnatural amino acids (that is, those that are not naturally found in proteins) are also known in the art, as set forth in, for example, Mol Cell Biot 9:2574 (1989); J Amer Chem Soc 112:4011-4030 (1990); J Amer Chem Soc 56:1280-1283 (1991); J Amer Chem Soc 113:9276-9286 (1991); and all references cited therein. β- and γ-Amino acids are known in the art and are also contemplated herein as unnatural amino acids. The following table shows non-limiting examples of unnatural amino acids that are contemplated herein.

TABLE 1

Exemplary Unnatural Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

As used herein, a "chemically modified amino acid" refers to an amino acid whose side chain has been chemically modified. For example, a side chain may be modified to comprise a signaling moiety, such as a fluorophore or a radiolabel. A side chain may be modified to comprise a new functional group, such as a thiol, carboxylic acid, or amino group. Post-translationally modified amino acids are also included in the definition of chemically modified amino acids.

Amino acids, and, more specifically, their side chains, may be characterized by their chemical characteristic(s). For example, amino acid side chains may be positively charged, negatively charged, or neutral. The pH of a solution affects the charged nature of certain side chains, as is known by those of skill in the art. Non-limiting examples of side chains that may be positively charged include histidine, arginine, and lysine. Non-limiting examples of side chains that may be negatively charged include aspartic acid and glutamic acid. Non-limiting examples of side chains that may be characterized as neutral include glycine, alanine, phenylalanine, valine, leucine, isoleucine, cysteine, asparagine, glutamine, serine, threonine, tyrosine, methionine, proline, and tryptophan.

Sterics of side chains may also be used to characterize an amino acid. Tables of atom diameters may assist one in determining whether one side chain is larger than another. Computer models may also help with this determination.

Amino acids may be characterized by the polarity of their side chains. Polar side chains, which are typically more hydrophilic than non-polar side chains, include, for example, those of serine, threonine, tyrosine, cysteine, asparagine, and glutamine. Non-polar side chains, which are typically more hydrophobic than polar side chains, include, for example, those of glycine, alanine, valine, leucine, isoleucine, proline, methionine, phenylalanine, and tryptophan. One may determine polarity of a side chain using conventional techniques known in the art involving atom electronegativity determinations and three-dimensional structural assessments of side chains. One may also compare hydrophobicities/hydrophilicities of side chains using conventional techniques known in the art, such as comparing the octanol/water partition coefficient of each amino acid. See Sangster, In: "Octanol-Water Partition Coefficients: Fundamentals and Physical Chemistry," Wiley Series in Solution Chemistry, Chichester: John Wiley & Sons Ltd., 2:178 (1997).

As used herein, a "peptide" refers to two or more amino acids joined together by an amide bond (that is, a "peptide bond"). Peptides comprise up to or include 50 amino acids. Peptides may be linear or cyclic. Peptides may be α, β, γ, δ, or higher, or mixed. Peptides may comprise any mixture of amino acids as defined herein, such as comprising any combination of D, L, α, β, γ, δ, or higher amino acids.

As used herein, a "protein" refers to an amino acid sequence having 51 or more amino acids.

The term "nucleic acid" refers to a deoxyribonucleotide or ribonucleotide polymer in either single- or double-stranded form, and unless otherwise limited, encompasses known analogs of natural nucleotides that hybridize to nucleic acids in manner similar to naturally occurring nucleotides, such as peptide nucleic acids (PNAs) and phosphorothioate DNA. Unless otherwise indicated, a particular nucleic acid sequence includes the complementary sequence thereof. Nucleotides include, but are not limited to, ATP, dATP, CTP, dCTP, GTP, dGTP, UTP, TTP, dUTP, 5-methyl-CTP, 5-methyl-dCTP, ITP, dITP, 2-amino-adenosine-TP, 2-amino-deoxyadenosine-TP, 2-thiothymidine triphosphate, pyrrolo-pyrimidine triphosphate, and 2-thiocytidine, as well as the alphathiotriphosphates for all of the above, and 2'-O-methyl-ribonucleotide triphosphates for all the above bases. Modified bases include, but are not limited to, 5-Br-UTP, 5-Br-dUTP, 5-F-UTP, 5-F-dUTP, 5-propynyl dCTP, and 5-propynyl-dUTP.

"Molecular motors" are well-known in the art and refer to a molecule (e.g., an enzyme) that physically interacts with an analyte, such as a polymer (e.g., a polynucleotide), and is capable of physically moving the analyte with respect to a fixed location, such as the opening of a nanopore (e.g., a tunnel of an Msp porin). Although not intending to be bound by theory, molecular motors utilize chemical energy to generate mechanical force. In some embodiments, a molecular motor may interact with each unit (or "mer") of a polymer in a sequential manner. Non-limiting examples of molecular motors include DNA polymerases, RNA polymerases, helicases, ribosomes, and exonucleases. Non-enzymatic motors are also known, such as virus motors that pack DNA. See Nature 413:748 (2001). A variety of molecular motors and desirable properties of such motors are described in U.S. Pat. No. 7,238,485, which is incorporated herein by reference in its entirety. A molecular motor may be disposed on the cis side or the trans side of a membrane and may optionally be immobilized, such as described by the '485 patent. Methods of incorporating a molecular motor into a nanopore may be performed using, e.g., methods described in the '485 patent. Systems and apparatuses described in the '485 patent may be employed with respect to a membrane comprising a nanopore described herein as well. Molecular motors are also discussed in, e.g., J Amer Chem Soc 130:818 (2008); Nature Nanotech 2:718 (2007); and ACS Nano 3:1457 (2009). Molecular motors as described in WO 2010/034018, incorporated herein by reference in its entirety, may also be employed in the context of nanopores and membranes described herein.

Beads that may be employed include magnetic beads. For example, one may use streptavidin-coated magnetic beads to apply an opposing force to the electrostatic forces that pull a modified analyte through the opening of a nanopore. For example, a magnetic bead is attached to biotinylated DNA, and a force comparable to the electrostatic driving force (~10 pN) is applied using a strong magnetic field gradient. See Biophys J 82:3314 (2002). In this way, the blockade-current readout would be unaffected, but the forces on the DNA could be independently controlled. Tens or hundreds of complete, independent reads of each DNA could then be correlated and assembled to reconstruct an accurate DNA sequence. In some embodiments, the magnetic bead does not fit through the pore, but it can be used once a translocation initiation tail has made it through the pore.

As used herein, "cis" refers to the side of a nanopore opening through which an analyte or modified analyte enters the opening or across the face of which the analyte or modified analyte moves.

As used herein, "trans" refers to the side of a nanopore opening through which an analyte or modified analyte (or fragments thereof) exits the opening or across the face of which the analyte or modified analyte does not move.

As used herein, "translocation" and grammatical variants means to enter one side of an opening of a nanopore and move to and out of the other side of the opening. It is specifically contemplated that any embodiment herein comprising translocation may refer to electrophoretic translocation or non-electrophoretic translocation, unless specifically noted. An electric field may move an analyte or modified analyte. By "interacts," it is meant that the analyte or modified analyte moves into and, optionally, through the opening, where "through the opening" (or "translocates") means to enter one side of the opening and move to and out of the other side of the opening. Optionally, methods that do not employ electrophoretic translocation are contemplated. In some embodiments, physical pressure causes a modified analyte to interact with, enter, or translocate (after alteration) through the opening. In some embodiments, a magnetic bead is attached to an analyte or modified analyte on the trans side, and magnetic force causes the modified analyte to interact with, enter, or translocate (after alteration) through the opening.

A "*Mycobacterium smegmatis* porin (Msp)" or "Msp porin" refers to a multimer complex comprised of two or more Msp monomers. An Msp monomer is encoded by a gene in *Mycobacterium smegmatis. Mycobacterium smegmatis* has four identified Msp genes, denoted MspA, MspB, MspC, and MspD. An Msp porin can, for example, be comprised of wild-type MspA monomers, mutant MspA monomers, wild-type MspA paralog or homolog monomers, or mutant MspA paralog or homolog monomers. Optionally, an Msp porin is a single-chain Msp porin or is a multimer of several single-chain Msp porins. A single-chain Msp porin can, for example comprise a multimer formed by two or more Msp monomers (e.g., eight monomers) connected by one or more amino acid linker peptides. A partial single chain Msp porin refers to a single-chain multimer complex that must dimerize, trimerize, or the like to form a porin. A full single-chain Msp porin refers to a single-chain multimer complex that forms a porin without the need to dimerize, trimerize or the like to form a porin. Msp porins are known in the art as are methods of making mutant Msp porins. International application WO 2010/034018, incorporated herein by reference in its entirety, describes many of these porins and methods of making these porins.

A "vestibule" refers to the cone-shaped portion of the interior of an Msp porin whose diameter generally decreases from one end to the other along a central axis, where the narrowest portion of the vestibule is connected to the constriction zone. A vestibule may also be referred to as a "goblet." See FIG. 1 of WO 2010/034018 for an example of the vestibule of a wild-type MspA porin. The vestibule and the constriction zone together define the tunnel of an Msp porin.

When referring to a diameter of the vestibule of an Msp porin, it is understood that because the vestibule is cone-like in shape, the diameter changes along the path of a central axis, where the diameter is larger at one end than the opposite end. The diameter may range from about 2 nm to about 6 nm. Optionally, the diameter is about, at least about, or at most about 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 nm, or any range derivable therein. The length of the central axis may range from about 2 nm to about 6 nm. Optionally, the length is about, at least about, or at most about 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 nm, or any range derivable therein. When referring to "diameter" herein, one may determine a diameter by measuring center-to-center distances or atomic surface-to-surface distances.

A "constriction zone" refers to the narrowest portion of the tunnel of an Msp porin, in terms of diameter, that is connected to the vestibule. The constriction zone of a wild-type MspA porin is shown in FIG. 1 of WO 2010/034018 (labeled "inner constriction"). The length of the constriction zone may range from about 0.3 nm to about 2 nm. Optionally, the length is about, at most about, or at least about 0.3, 0.4, 0.5, 0.6, 0.7, 0.8, 0.9, 1.0, 1.1, 1.2, 1.3, 1.4, 1.5, 1.6, 1.7, 1.8, 1.9, 2, or 3 nm, or any range derivable therein. The diameter of the constriction zone may range from about 0.3 nm to about 2 nm. Optionally, the diameter is about, at most about, or at least about 0.3, 0.4, 0.5, 0.6, 0.7, 0.8, 0.9, 1.0, 1.1, 1.2, 1.3, 1.4, 1.5, 1.6, 1.7, 1.8, 1.9, 2, or 3 nm, or any range derivable therein.

A "neutral constriction zone" refers to a constriction zone comprising amino acid side chains that cumulatively exhibit no net electrical charge when immersed in an aqueous solution. The pH of the liquid medium (e.g., a buffered aqueous solution) in contact with the constriction zone may affect whether the constriction zone is characterized as neutral or not.

A "tunnel" refers to the central, empty portion of an Msp porin that is defined by the vestibule and the constriction zone, through which a gas, liquid, ion, or analyte may pass. A tunnel is an example of an opening of a nanopore.

A "mutant MspA porin" is a multimer complex that has at least or at most 70, 75, 80, 85, 90, 95, 98, or 99 percent or more identity, or any range derivable therein, but less than 100%, to its corresponding wild-type MspA porin and retains tunnel-forming capability. A mutant MspA porin may be recombinant protein. Optionally, a mutant MspA porin is one having a mutation in the constriction zone or the vestibule of a wild-type MspA porin. Optionally, a mutation may occur in the rim or the outside of the periplasmic loops of a wild-type MspA porin. A mutant MspA porin may be employed in any embodiment described herein.

Regarding the MspA porin in particular, optionally, the MspA porin is an octamer that consists of eight 184-amino acid MspA monomers. One or more mutations may take place in one or more of the amino acid MspA monomers of a wild-type MspA porin to yield a mutant MspA porin. In addition, an MspA porin may have fewer or more than eight monomers, any one or more of which may comprise a mutation.

Wild-type MspA porin comprises a periplasmic loop that consists of thirteen amino acids and is directly adjacent to the constriction zone. See J. Biol. Chem. 284:10223 (2009). Wild-type MspB, C, and D porins also contain a periplasmic loop. One or more mutations may occur in the periplasmic loop of a wild-type Msp porin to generate a mutant Msp porin. For example, deletions of up to all thirteen amino acids may occur in the periplasmic loop of wild-type MspA porin. Typically, deletions in the periplasmic loop do not affect the tunnel-forming ability of an Msp porin.

An Msp porin or Msp monomer may also be chemically or biologically modified. For example, one may modify an Msp porin or Msp monomer with chemicals to produce disulfide bridges, as is known by those of skill in the art.

An Msp porin may comprise a nucleotide binding site. As used herein, a "nucleotide binding site" refers to a site in an Msp porin where a nucleotide stays in contact with, or resides at, an amino acid for a period of time that is longer than attributable to diffusion movement, such as greater than one picosecond or one nanosecond. Molecular dynamics calculations may be employed to assess these temporary resting times.

One or more mutations in an Msp porin may occur in the vestibule or the constriction zone of the protein. Optionally, a mutant Msp porin has at least one difference in its periplasmic loop, vestibule, or constriction zone amino acid sequence (e.g., deletion, substitution, addition) compared with the wild-type Msp porin. Optional mutations are described herein.

The Msp porin of any embodiment herein may be any Msp porin described herein, such as a wild-type MspA porin, a mutant MspA porin, a wild-type MspA paralog or homolog porin, or a mutant MspA paralog or homolog porin. The Msp porin may be encoded by a nucleic acid sequence encoding a single-chain Msp porin. Any Msp porin here may comprise any Msp monomer described herein, such as a mutant Msp monomer.

Nutrients pass through wild-type porins in mycobacteria. Wild-type MspA porins, wild-type MspB porins, wild-type MspC porins, and wild-type MspD porins are examples of wild-type tunnel-forming porins. An Msp porin may be further defined as any Msp porin described herein, including paralogs, homologs, mutants and single-chain porins.

Exemplary wild-type MspA paralogs and homologs are provided in Table 2. Provided are wild-type MspA paralogs, which include wild-type MspB, wild-type MspC, and wild-type MspD. A "paralog," as defined herein, is a gene from the same bacterial species that has similar structure and function. A "homolog," as defined herein, is a gene from another bacterial species that has a similar structure and evolutionary origin. By way of an example, provided are wild-type MspA homologs, which include MppA, PorM1, PorM2, PorM1, and Mmcs4296.

TABLE 2

Exemplary Wild-Type MspA and Wild-Type MspA Paralogs and Homolog Monomers

| Protein# | Organism | Identity/ Similarity to MspA (%) | Length (aa) | Reference |
|---|---|---|---|---|
| MspA/Msmeg0965 | *M. smegmatis* | 100/100 | 211 | gb\|ABK74363.1\|, (Stahl et al., 2001)* |
| MspB/Msmeg0520 | *M. smegmatis* | 94/95 | 215 | gb\|ABK73437.1\|, (Stahl et al., 2001)* |
| MspC/Msmeg5483 | *M. smegmatis* | 93/95 | 215 | gb\|ABK74976.1\|, (Stahl et al., 2001)* |
| MspD/Msmeg6057 | *M. smegmatis* | 82/89 | 207 | gb\|ABK72453.1\|, (Stahl et al., 2001)* |
| MppA | *M. phlei* | 100/100 | 211 | AJ812030, (Domer et al., 2004)** |
| PorM1 | *M. fortuitum* | 95/96 | 211 | emb\|CAI54228.1\| |
| PorM2 | *M. fortuitum* | 91/93 | 215 | emb\|CAL29811.1\| |
| PorM1 | *M. peregrinum* | 94/96 | 211 | emb\|CAI54230.1\| |
| Mmcs4296 | *Mycobacterium* sp. MCS | 85/91 | 216 | gb\|ABG10401.1\| |
| Mmcs4297 | *Mycobacterium* sp. MCS | 85/91 | 216 | gb\|ABG10402.1\| |
| Mmcs3857 | *Mycobacterium* sp. MCS | 30/44 | 235 | gb\|ABG09962.1\| |
| Mmcs4382 | *Mycobacterium* sp. MCS | 85/91 | 216 | gb\|ABL93573.1\| |
| Mmcs4383 | *Mycobacterium* sp. MCS | 85/91 | 216 | gb\|ABL93574.1\| |
| Mjls3843 | *Mycobacterium* sp. JLS | 26/40 | 235 | gb\|ABN99619.1\| |
| Mjls3857 | *Mycobacterium* sp. JLS | 26/40 | 235 | gb\|ABG09962.1\| |
| Mjls3931 | *Mycobacterium* sp. JLS | 26/40 | 235 | gb\|ABL93123.1\| |
| Mjls4674 | *Mycobacterium* sp. JLS | 85/89 | 216 | gb\|ABO00440.1\| |

TABLE 2-continued

| Exemplary Wild-Type MspA and Wild-Type MspA Paralogs and Homolog Monomers | | | | |
|---|---|---|---|---|
| Protein# | Organism | Identity/ Similarity to MspA (%) | Length (aa) | Reference |
| Mjls4675 | *Mycobacterium* sp. JLS | 83/89 | 216 | gb\|ABO00441.1\| |
| Mjls4677 | *Mycobacterium* sp. JLS | 84/89 | 216 | gb\|ABO00443.1\| |
| Map3123c | *M. avium* paratuberculosis | 24/39 | 220 | gb\|AAS05671.1\| |
| Mav3943 | *M. avium* | 24/39 | 227 | gb\|ABK66660.1\| |
| Mvan1836 | *M. vanbaalenii* PYR-1 | 82/88 | 209 | gb\|ABM12657.1\| |
| Mvan4117 | *M. vanbaalenii* PYR-1 | 32/43 | 239 | gb\|ABM14894.1\| |
| Mvan4839 | *M. vanbaalenii* PYR-1 | 83/88 | 209 | gb\|ABM15612.1\| |
| Mvan4840 | *M. vanbaalenii* PYR-1 | 83/89 | 209 | gb\|ABM15613.1\| |
| Mvan5016 | *M. vanbaalenii* PYR-1 | 30/41 | 238 | gb\|ABM15788.1\| |
| Mvan5017 | *M. vanbaalenii* PYR-1 | 25/35 | 227 | gb\|ABM15789.1\| |
| Mvan5768 | *M. vanbaalenii* PYR-1 | 21/32 | 216 | gb\|ABM16533.1\| |
| MUL_2391 | *M. ulcerans* Agy99 | 21/34 | 233 | gb\|ABL04749.1\| |
| Mflv1734 | *M. gilvum* PYR-GCK | 21/32 | 225 | gb\|ABP44214.1\| |
| Mflv1735 | *M. gilvum* PYR-GCK | 32/41 | 226 | gb\|ABP44215.1\| |
| Mflv2295 | *M. gilvum* PYR-GCK | 25/40 | 250 | gb\|ABP44773.1\| |
| Mflv1891 | *M. gilvum* PYR-GCK | 84/90 | 217 | gb\|ABP44371.1\| |
| MCH4691c | *M. chelonae* | 70/80 | 223 | gb\|ACV04474.1\| |
| MCH4689c | *M. chelonae* | 66/78 | 223 | gb\|ACV04472.1\| |
| MCH4690c | *M. chelonae* | 72/81 | 217 | gb\|ACV04473.1\| |
| MAB1080 | *M. abscessus* | 69/79 | 223 | emb\|CAM61170.1\| |
| MAB1081 | *M. abscessus* | 68/78 | 222 | emb\|CAM61171.1\| |
| MAB2800 | *M. abscessus* | 27/44 | 246 | emb\|CAM62879.1\| |
| RHA1 ro08561 | *Rhodococcus jostii* RHA1 | 34/51 | 233 | gb\|ABG99605.1\| |
| n.d. | *Rhodococcus opacus* B4 | 34/51 | 233 | gbj\|BAH52196.1\| |
| RHA1 ro04074 | *Rhodococcus* sp. RHA1 | 34/50 | 233 | gb\|ABG95871.1\| |
| RHA1 ro03127 | *Rhodococcus* sp. RHA1 | 34/50 | 233 | gb\|ABG94930.1\| |
| n.d. | *Rhodococcus erythropolis* PR4 | 35/50 | 229 | gbj\|BAH30938.1\| |

n.d.: "not determined"
*Mol. Microbiol. 40:451 (2001)
**Biochim. Biophys. Acta 1667: 47-55 (2004)

Only proteins with significant amino acid similarities over the full length of the protein were included. Data were obtained by PSI-Blast algorithm (BLOSUM62 matrix) using the NIH GenBank database on the world wide web at ncbi.nlm.nih.gov/blast/Blast.cgi.

A "mutant MspA paralog or homolog porin" is a multimer complex that has at least or at most 70, 75, 80, 85, 90, 95, 98, or 99 percent or more identity, or any range derivable therein, but less than 100%, to its corresponding wild-type MspA paralog or homolog porin and retains tunnel-forming capability. A mutant MspA paralog or homolog porin may be recombinant protein. Optionally, a mutant MspA paralog or homolog porin is one having a mutation in the constriction zone or the vestibule of the wild-type MspA paralog or homolog porin. Optionally, a mutation may occur in the rim or the outside of the periplasmic loops of a wild-type MspA paralog or homolog porin. Any mutant MspA paralog or homolog porin may be employed in any embodiment described herein, and may comprise any mutation described herein.

An Msp porin may comprise two or more Msp monomers. An "Msp monomer" is a protein monomer that is either a wild-type MspA monomer, a mutant MspA monomer, a wild-type MspA paralog or homolog monomer, or a mutant MspA paralog or homolog monomer, and retains tunnel-forming capability when associated with one or more other Msp monomers. Any Msp porin described herein may comprise one or more of any Msp monomer as described herein. Any Msp porin may comprise, for example, 2-15 Msp monomers, wherein each monomer may be the same or different.

A "mutant MspA monomer" refers to an Msp monomer that has at least or at most 70, 75, 80, 85, 90, 95, 98, or 99 percent or more identity, or any range derivable therein, but less than 100%, to a wild-type MspA monomer, and retains tunnel-forming capability when associated with one or more other Msp monomers. Optionally, a mutant MspA monomer is further defined as comprising a mutation in that portion of the sequence that contributes to the formation of the vestibule or the constriction zone of a fully-formed, tunnel-forming porin. The mutant Msp monomer may be a recombinant protein, for example. A mutant MspA monomer may comprise any mutation described herein.

In any embodiment herein, an Msp monomer may be a wild-type MspA paralog or homolog, such as MspA/Msmeg0965, MspB/Msmeg0520, MspC/Msmeg5483, MspD/Msmeg6057, MppA, PorM1, PorM2, PorM1, Mmcs4296, Mmcs4297, Mmcs3857, Mmcs4382, Mmcs4383, Mjls3843, Mjls3857, Mjls3931 Mjls4674, Mjls4675, Mjls4677, Map3123c, Mav3943, Mvan1836, Mvan4117, Mvan4839, Mvan4840, Mvan5016, Mvan5017, Mvan5768, MUL_2391, Mflv1734, Mflv1735, Mflv2295, Mflv1891, MCH4691c, MCH4689c, MCH4690c, MAB1080, MAB1081, MAB2800, RHA1 ro08561, RHA1 ro04074, and RHA1 ro03127.

A "mutant MspA paralog or homolog monomer" refers to an MspA paralog or homolog monomer that has at least or at most 70, 75, 80, 85, 90, 95, 98, or 99 percent or more identity, or any range derivable therein, but less than 100%, to a wild-type MspA paralog or homolog monomer, and retains tunnel-forming capability. Optionally, a mutant MspA paralog or homolog monomer is further defined as comprising a mutation in that portion of the sequence that contributes to the formation of the vestibule and/or the constriction zone of a fully-formed, tunnel-forming porin. The mutant MspA paralog or homolog monomer may be a recombinant protein, for example. Any mutant MspA paralog or homolog monomer may be optionally employed in any embodiment herein.

An Msp porin may be expressed as a combination of two or more wild-type MspA monomers, mutant MspA monomers, wild-type MspA paralog or homolog monomers, or mutant MspA paralog or homolog monomers. As such, an Msp porin may be or comprise a dimer, a trimer, a tetramer, a pentamer, a hexamer, a septamer, an octamer, a nonamer, etc. For example, an Msp porin may comprise a combination of wild-type MspA monomers and wild-type MspB monomers. An Msp porin may comprise 1-15 monomers, where each monomer is the same or different. Indeed, any Msp porin described herein may comprise at least or at most 1, 2, 3, 4, 5, 6, 7, 8, 9, 10, 11, 12, 13, 14, or 15 monomers, or any range derivable therein, where each monomer is the same or different. For example, an Msp porin may comprise one or more mutant MspA monomers that are the same or different. As another example, an Msp porin may comprise at least one mutant MspA monomer and at least one MspA paralog or homolog monomer.

As defined above, a single-chain Msp porin comprises two or more Msp monomers connected by one or more amino acid linker peptides. A single-chain Msp porin that comprises two Msp monomers, wherein the Msp monomers are linked by an amino acid linker sequence, may be referred to as a single-chain Msp porin dimer. A single-chain Msp porin that comprises eight Msp monomers, wherein the Msp monomers are linked by an amino acid linker sequence, may be referred to as a single-chain Msp porin octamer. A single-chain Msp porin may comprise 2, 3, 4, 5, 6, 7, 8, 9, 10, 11, 12, 13, 14, 15, or more Msp monomers, or any range derivable therein, linked by amino acid linker sequences. Optionally, a single-chain Msp porin can, for example, comprise two or more single-chain Msp porin dimers, two or more single-chain Msp porin trimers, two or more single-chain Msp porin quadrimers, two or more single-chain Msp porin pentimers, one or more single-chain Msp porin heximers, one or more single-chain Msp porin septimers, one or more single-chain Msp porin octamers, or combinations thereof. For example, a single-chain Msp porin can comprise a single-chain Msp porin dimer and two single-chain Msp porin trimers. By way of another example, a single-chain Msp porin can comprise a single-chain Msp porin quadrimer and two single-chain Msp porin dimers.

A wild-type single-chain Msp porin is comprised of wild-type Msp monomers. Optionally, one or more mutations in a single-chain Msp porin is present in the vestibule or the constriction zone of the single-chain Msp porin. The mutant single-chain Msp porin, for example, has at least one mutation in the amino acid sequence for the periplasmic loop, vestibule, or constriction zone (e.g., deletion, substitution, or addition) compared with a wild-type single-chain Msp. A multimer of single chains can also form a porin, wherein each single chain includes two, three, four, five, six, seven, or more Msp monomers.

Non-limiting examples of mutant MspA sequences are provided in Table 3. Optionally, the mutant MspA comprises an A-to-P substitution at amino acid 138, an E-to-A substitution at amino acid 139, or a combination thereof. Optionally, the mutant MspA comprises a D-to-K or R substitution at amino acid 90, a D-to-N substitution at amino acid 91, a D-to-N substitution at amino acid 93, or any combination thereof. Optionally, the mutant MspA comprises a D-to-Q substitution at amino acid 90, a D-to-Q substitution at amino acid 91, a D-to-N substitution at amino acid 93, or any combination thereof. Optionally, the mutant MspA comprises a L-to-W substitution at amino acid 88, an I-to-W substitution at amino acid 105, a D-to-Q substitution at amino acid 91, a D-to-N substitution at amino acid 93, or any combination thereof. Optionally, the mutant MspA comprises an I-to-W substitution at amino acid 105, an N-to-W substitution at amino acid 108, or a combination thereof. Optionally, the mutant MspA comprises a D-to-R substitution at amino acid 118, an E-to-K substitution at amino acid 139, a D-to-R substitution at amino acid 134, or any combination thereof. For the mutant MspB monomer sequences listed below, the reference MspB sequence is the mature wild-type MspB monomer sequence, which is known in the art. Optionally, the mutant MspB comprises a D-to-K or R substitution at amino acid 90, a D-to-N substitution at amino acid 91, a D-to-N substitution at amino acid 93, or any combination thereof.

TABLE 3

| MspA mutants | |
|---|---|
| Row 1 | Row 2 |
| MspA D90A | MspA T84C |
| MspA D91A | MspA I87C |
| MspA D90A/D91A | MspA D91C |
| MspA D90E | MspA D93C |
| MspA D91E | MspA A96C |
| MspA D90E/D91E | MspA P97C |
| MspA D90F | MspA G100C |
| MspA D91F | MspA N102C |
| MspA D90F/D91F | MspA P107C |
| MspA D90G | MspA G112C |
| MspA D91G | MspA V113C |
| MspA D90G/D91G | MspA S114C |
| MspA D90H | MspA D118C |
| MspA D91H | MspA N121C |
| MspA D90H/D91H | MspA E127C |

TABLE 3-continued

| MspA mutants | |
|---|---|
| Row 1 | Row 2 |
| MspA D90K | MspA F131C |
| MspA D91K | MspA D134C |
| MspA D90K/D91K | MspA S136C |
| MspA D90L | MspA A138C |
| MspA D91L | MspA E139C |
| MspA D90L/D91L | MspA G141C |
| MspA D90R | MspA V144C |
| MspA D91R | MspA H148C |
| MspA D90R/D91R | MspA T150C |
| MspA D90S | MspA A155C |
| MspA D91S | MspA R161C |
| MspA D90S/D91S | MspA R165C |
| MspA D90W | MspA S173C |
| MspA D91W | MspA T175C |
| MspA D90W/D91W | MspA E179C |
| MspA D90Y | MspA V184C |
| MspA D91Y | MspA N79C/D90K/D91N/P97C |
| MspA D90Y/D91Y | MspA K47S/D90K/D91N/P97C/D134C |
| MspA Q126C | MspA ΔA96-P98 |
| MspA D90N | MspA ΔT95-F99 |
| MspA D91N | MspA ΔI94-G100 |
| MspA D93N | MspA ΔD93-L101 |
| MspA D90N/D91N | MspA ΔG92-N102 |
| MspA D90N/D91N/D93N | MspA N79R/D90N/D91N/D93N |
| MspA D90Q/D91N/D93N | MspA N79W/D90N/D91N/D93N |
| MspA D90Q/D91Q/D93N | MspA D90N/D91N/D93N/Q126R |
| MspA D90T/D91N/D93N | MspA D90N/D91N/D93N/T130R |
| MspA D90T/D91T/D93N | MspA D90N/D91N/D93N/D134R |
| MspA D91E | MspA D90N/D91N/D93N/Q126W |
| MspA D90E | MspA D90N/D91N/D93N/T130W |
| MspA D90E/D91E | MspA D90N/D91N/D93N/D134W |
| MspA D90N/D91N/D93Q | MspA D90N/D91N/D93N/D118W/D134R/E139K |
| MspA D90N/D91N/G92Q/D93N | MspA D90N/D91N/D93N/D118F/D134R/E139K |
| MspA G1C | MspA D90N/D91N/D93N/D118H/D134R/E139K |
| MspA D3C | MspA D90N/D91N/D93N/D118Y/D134R/E139K |
| MspA E5C | MspA N79W/D90N/D91N/D93N/D118R/E139K |
| MspA D10C | MspA N79F/D90N/D91N/D93N/D118R/E139K |
| MspA D13C | MspA N79H/D90N/D91N/D93N/D118R/E139K |
| MspA R14C | MspA N79Y/D90N/D91N/D93N/D118R/E139K |
| MspA T17C | MspA D90N/D91K/D93N |
| MspA W21C | MspA D90N/D91R/D93N |
| MspA D22C | MspA D90N/D91W/D93N |
| MspA G27C | MspA D90N/D91W/D93N |
| MspA R33C | MspA D90N/D91T/D93N |
| MspA R38C | MspA D90N/D91L/D93N |
| MspA G44C | MspA D90N/D91H/D93N |
| MspA K47C | MspA D90N/D91S/D93N |
| MspA I49C | MspA D90N/D91N/D93N/D118R |
| MspA E57C | MspA D90N/D91N/D93N/D118R/E139R |
| MspA G60C | MspA D90N/D91N/D93N/D118R/E139K |
| MspA E63C | MspA D90N/D91N/D93N/D118R/D134R/E139K |
| MspA G69C | MspA D90Q/D91N/D93N/D118R/D134R/E139K |
| MspA S73C | MspA D90Q/D91Q/D93N/D118R/D134R/E139K |
| MspA L74C | MspA D90T/D91N/D93N/D118R/D134R/E139K |
| MspA V76C | MspA D90T/D91T/D93N/D118R/D134R/E139K |

An MspA monomer may comprise one or more mutations at any of the following amino acid positions: 88, 105, 108, 118, 134, or 139. An MspA monomer may comprise one or more of the following mutations: L88W, D90K/N/Q/R, D91N/Q, D93N, 1105W, N108W, D118R, D134R, or E139K. An MspA monomer may comprise the following mutations: D90N/D91N/D93N. An MspA monomer may comprise the following mutations: D90N/D91N/D93N/D118R/D134R/E139K. An MspA monomer may comprise the following mutations: D90Q/D91Q/D93N. An MspA monomer may comprise the following mutations: D90Q/D91Q/D93N/D118R/D134R/E139K. An MspA monomer may comprise the following mutations: D90(K,R)/D91N/D93N. An MspA monomer may comprise the following mutations: (L88, I105)W/D91Q/D93N. An MspA monomer may comprise the following mutations: I105W/N108W. Moreover, an MspA monomer may comprise any other mutation described herein.

In any embodiment herein, a mutant Msp porin, such as a mutant MspA porin or a mutant MspA paralog or homolog, may comprise at least one additional positively charged amino acid compared to the vestibule or the constriction zone of a wild-type Msp porin, respectively; at least one additional negatively charged amino acid compared to the vestibule or the constriction zone of a wild-type MspA porin, respectively; at least one less positively charged amino acid compared to the vestibule or the constriction zone of a wild-type MspA porin, respectively; or at least one less negatively charged amino acid compared to the vestibule or the constriction zone of a wild-type MspA porin, respectively.

Optionally, each positively charged amino acid in the vestibule and the constriction zone of a wild-type Msp porin is replaced with a negatively charged amino acid, and each negatively charged amino acid is the same or different; or each negatively charged amino acid in the vestibule and the constriction zone of a wild-type Msp porin is replaced with a positively charged amino acid, and each positively charged amino acid is the same or different.

Optionally, the vestibule or the constriction zone of a mutant Msp porin comprises a greater number of positively charged residues than that of the vestibule or the constriction zone of a wild-type Msp porin, respectively; or the vestibule or the constriction zone comprises a greater number of negatively charged residues than that of the vestibule or the constriction zone of a wild-type Msp porin, respectively; or at least one positively charged amino acid in the vestibule or the constriction zone of a wild-type Msp porin, such as wild-type MspA porin or a wild-type MspA paralog or homolog porin, is either deleted or replaced by a negatively charged amino acid; or at least one negatively charged amino acid in the vestibule or the constriction zone of a wild-type Msp porin is either deleted or replaced by a positively charged amino acid.

At least one amino acid in the vestibule or the constriction zone of a wild-type Msp porin, such as a wild-type MspA porin or a wild-type MspA paralog or homolog porin, may be substituted by an amino acid having a sterically larger side chain; an amino acid having a sterically smaller side chain; an amino acid having a more polar side chain; an amino acid having a less polar side chain; or an amino acid having a more hydrophobic side chain; an amino acid having a less hydrophobic side chain.

In any embodiment herein, at least one amino acid in the vestibule or the constriction zone of a mutant Msp porin may comprise an unnatural amino acid or a chemically modified amino acid.

A mutant Msp porin, such as a mutant MspA porin or a mutant MspA paralog or homolog porin, may comprise a neutral constriction zone. A mutant Msp porin, such as a mutant MspA porin or a mutant MspA paralog or homolog porin, may comprise a conductance through the tunnel that is higher, such as two-fold higher, than the conductance through the tunnel of its corresponding wild-type Msp porin. A mutant Msp porin, such as a mutant MspA porin or a mutant MspA paralog or homolog porin, may comprise a conductance through the tunnel that is lower than the conductance through the tunnel of its corresponding wild-type Msp porin.

Any Msp porin discussed herein may comprise a vestibule having a length from about 2 to about 6 nm and a diameter from about 2 to about 6 nm, and a constriction zone having a length from about 0.3 to about 3 nm and a diameter from about 0.3 to about 3 nm, wherein the vestibule and constriction zone together define a tunnel. Also provided herein is a mutant MspA porin comprising a vestibule having a length from about 2 to about 6 nm and a diameter from about 2 to about 6 nm, and a constriction zone having a length from about 0.3 to about 3 nm and a diameter from about 0.3 to about 3 nm, wherein the vestibule and constriction zone together define a tunnel, and further comprising at least a first mutant MspA paralog or homolog monomer.

The diameter of the constriction zone of a mutant Msp porin, such as a mutant MspA porin or mutant MspA paralog or homolog, may be less than the diameter of the constriction zone of its corresponding wild-type Msp porin, such as a wild-type MspA porin or wild-type MspA paralog or homolog. A mutant Msp porin, such as a mutant MspA porin or mutant MspA paralog or homolog, may comprise a mutation in the vestibule or the constriction zone that permits an analyte or a modified analyte to have a velocity or an average velocity as it interacts with the tunnel that is less than the velocity or average velocity at which the analyte or a modified analyte interacts with the tunnel of its corresponding wild-type Msp porin, (e.g., wild-type MspA porin, wild-type MspA paralog or homolog).

Sequences of wild-type Msp monomers discussed herein are disclosed in GenBank, located on the world wide web at pubmed.gov, and these sequences and others are herein incorporated by reference in their entireties as are individual subsequences or fragments contained therein. For example, the nucleotide and amino acid sequences of a wild-type MspA monomer can be found at GenBank Accession Nos. AJ001442 and CAB56052, respectively. The nucleotide and amino acid sequences of a wild-type MspB monomer can be found, for example, at GenBank Accession Nos. NC_008596.1 (from nucleotide 600086 to 600730) and YP_884932.1, respectively. The nucleotide and amino acid sequences of a wild-type MspC monomer can be found, for example, at GenBank Accession Nos. AJ299735 and CAC82509, respectively. The nucleotide and amino acid sequences of a wild-type MspD monomer can be found, for example, at GenBank Accession Nos. AJ300774 and CAC83628, respectively. Thus provided are the nucleotide sequences of MspA, MspB, MspC, and MspD monomers comprising a nucleotide sequence at least about 70, 75, 80, 85, 90, 95, 98, 99 percent or more, or any range derivable therein, identical to the nucleotide sequence of the aforementioned nucleotide GenBank Accession numbers. Amino acid sequences of MspA, MspB, MspC, and MspD monomers may be found in FIG. 18 of WO 2010/034018 comprising an amino acid sequence at least about 70, 75, 80, 85, 90, 95, 98, 99 percent or more, or any range derivable therein, identical to the sequences of the aforementioned amino acid GenBank Accession numbers.

Also provided are amino acid sequences of MspA paralogs and homolog monomers comprising an amino acid sequence at least about 70, 75, 80, 85, 90, 95, 98, 99 percent or more, or any range derivable therein to a wild-type MspA paralog or homolog monomer. Wild-type MspA paralog and homolog monomers are well-known in the art. See Table 2.

The α-hemolysin pore is formed of seven identical subunits (heptameric). The polynucleotide sequence that encodes one subunit of α-hemolysin is shown in SEQ ID NO:1 of U.S. Patent Application Publication No. 2010/0196203, incorporated herein by reference in its entirety. The full-length amino acid sequence of one subunit of α-hemolysin is shown in SEQ ID NO:2 of U.S. Patent Application Publication No. 2010/0196203. The first 26 amino acids of SEQ ID NO:2 correspond to the signal peptide. The amino acid sequence of one mature subunit of α-hemolysin without the signal peptide is shown in SEQ ID NO:3 U.S. Patent Application Publication No. 2010/0196203. SEQ ID NO:3 has a methionine residue at position 1 instead of the 26 amino acid signal peptide that is present in SEQ ID NO:2.

A variant is a heptameric pore in which one or more of the seven subunits has an amino acid sequence which varies from that of SEQ ID NO:2 or 3 and which retains pore activity. 1, 2, 3, 4, 5, 6 or 7 of the subunits in a mutant α-hemolysin may have an amino acid sequence that varies from that of SEQ ID NO:2 or 3. The seven subunits within a mutant pore are typically identical but may be different.

The mutant may be a naturally-occurring variant which is expressed by an organism, for instance by a *Staphylococcus* bacterium. Variants also include non-naturally occurring variants produced by recombinant technology. Over the entire length of the amino acid sequence of SEQ ID NO:2 or 3, a variant may be at least 50% homologous to that sequence based on amino acid identity. The subunit polypeptide may be at least 80%, at least 90%, at least 95%, at least 98%, at least 99% homologous based on amino acid identity to the amino acid sequence of SEQ ID NO:2 or 3 over the entire sequence.

Amino acid substitutions may be made to the amino acid sequence of SEQ ID NO:2 or 3, for example, a single amino acid substitution may be made or two or more substitutions may be made. In some embodiments, replacement of the lysine at position 34 in SEQ ID NO:2 and position 9 in SEQ ID NO:3 with cysteine (i.e., K34C or K9C). Another example of a non-conservative substitution that may be made is the replacement of the asparagine residue at position 43 of SEQ ID NO:2 or position 18 of SEQ ID NO:3 with cysteine (i.e., N43C or N17C). The inclusion of these cysteine residues in SEQ ID NO:2 or 3 provides thiol attachment points at the relevant positions. Similar changes could be made at all other positions, and at multiple positions on the same subunit.

In some embodiments, one or more amino acid residues of the amino acid sequence of SEQ ID NO:2 or 3 may alternatively or additionally be deleted. Up to 50% of the residues may be deleted, either as a contiguous region or multiple smaller regions distributed throughout the length of the amino acid chain.

Variants can include subunits made of fragments of SEQ ID NO:2 or 3. Such fragments retain their ability to insert into a bilayer. Fragments can be at least 100, such as 150, 200 or 250, amino acids in length. Such fragments may be used to produce chimeric pores. A fragment may comprise the β-barrel domain of SEQ ID NO:2 or 3.

Variants include chimeric proteins comprising fragments or portions of SEQ ID NO:2 or 3. Chimeric proteins are formed from subunits each comprising fragments or portions of SEQ ID NO:2 or 3. The β-barrel part of chimeric proteins is typically formed by the fragments or portions of SEQ ID NO:2 or 3.

One or more amino acid residues may alternatively or additionally be inserted into, or at one or other or both ends of, the amino acid sequence SEQ ID NO:2 or 3. Insertion of one, two or more additional amino acids to the C terminal end of the peptide sequence is less likely to perturb the structure and/or function of the protein, and these additions could be substantial, but peptide sequences of up to 10, 20, 50, 100 or 500 amino acids or more can be used. Additions at the N terminal end of the monomer could also be substantial, with one, two or more additional residues added, but also 10, 20, 50, 500 or more residues being added. Additional sequences can also be added to the protein in the trans-membrane region, between amino acid residues 119 and 139 of SEQ ID NO:3. More precisely, additional sequences can be added between residues 127 and 130 of SEQ ID NO:3, following removal of residues 128 and 129. Additions can be made at the equivalent positions in SEQ ID NO:2. A carrier protein may be fused to an amino acid sequence according to the invention.

Other optional mutations are described herein.

Descriptions of additional optional substitutions that may be made with respect to Msp porins, Msp monomers, α-hemolysins, and other proteins provided herein are described below.

Descriptions of additional optional substitutions that may be made with respect to Msp porins, Msp monomers, and α-hemolysin and variants thereof, and other proteins provided herein are described below.

Protein modifications described herein include amino acid sequence modifications. Modifications in amino acid sequence may arise naturally as allelic variations (e.g., due to genetic polymorphism), may arise due to environmental influence (e.g., due to exposure to ultraviolet radiation), or may be produced by human intervention (e.g., by mutagenesis of cloned DNA sequences), such as induced point, deletion, insertion, and substitution mutants. These modifications can result in changes in the amino acid sequence, provide silent mutations, modify a restriction site, or provide other specific mutations. Amino acid sequence modifications typically fall into one or more of three classes: substitutional, insertional, or deletional modifications. Insertions include amino and/or terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about from 1 to 10 amino acid residues; and deletions will range about from 1 to 30 residues. Deletions or insertions may be made in adjacent pairs, i.e., a deletion of 2 residues or insertion of 2 residues. Substitutions, deletions, insertions or any combination thereof may be combined to arrive at a final construct. The mutations may or may not place the sequence out of reading frame and may or may not create complementary regions that could produce secondary mRNA structure. Substitutional modifications are those in which at least one residue has been removed and a different residue inserted in its place.

Modifications, including the specific amino acid substitutions, are made by known methods. By way of example, modifications are made by site specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example, M13 primer mutagenesis and PCR mutagenesis.

The peptides, polypeptides, monomers, multimers, proteins, etc. described herein can be further modified and varied so long as the desired function is maintained or enhanced. It is understood that one way to define any known modifications and derivatives or those that might arise, of the disclosed genes and proteins herein is through defining the modifications and derivatives in terms of identity to specific known sequences. Specifically disclosed are polypeptides which have at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to a wild-type MspA and wild-type MspA paralogs or homologs (e.g., wild-type MspB, wild-type MspC, wild-type MspD, MppA, PorM1, Mmcs4296) and mutants provided herein as well as α-hemolysin and variants thereof.

Those of skill in the art readily understand how to determine the identity of two polypeptides. For example, the identity can be calculated after aligning the two sequences so that the identity is at its highest level. For example, to determine the "percent identity" of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., percent identity=number of identical positions/total number of positions (e.g., overlapping positions)×100). In one embodiment, the two sequences are the same length.

Several methods exist for determining percent identity. One may determine percent identity in the following manner. A target nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from the U.S. Government's National Center for Biotechnology Information Web site (World Wide Web at ncbi.nlm.nih.gov). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options may be set as follows: -i is set to a file containing the first nucleic acid sequence to be compared (e.g., C:\seql.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. The following command will generate an output file containing a comparison between two sequences: C:\Bl2seq c:\seql.txt -j c:\seq2.txt -p blastn -o c:\output.txt -q -1-r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length may be determined by counting the number of matched positions over that length and dividing that number by the length followed by multiplying the resulting value by 100. For example, if (1) a 50 nucleotide target sequence is compared to the sequence encoding wild-type MspA (2) the Bl2seq program presents 45 nucleotides from the target sequence aligned with a region of the sequence encoding wild-type MspA where the first and last nucleotides of that 45 nucleotide region are matches, and (3) the number of matches over those 45 aligned nucleotides is 40, then the 50 nucleotide target sequence contains a length of 45 and a percent identity over that length of 89 (i.e., 40/45×100=89).

Another way of calculating identity can be performed by published algorithms. Optimal alignment of sequences for comparison may be conducted by the local identity algorithm of Smith and Waterman, Adv Appl Math 2:482 (1981), by the identity alignment algorithm of Needleman and Wunsch, J Mol Biol 48:443 (1970), by the search for similarity method of Pearson and Lipman, Proc Natl Acad. Sci USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Science 244:48-52 (1989); Proc Natl Acad Sci USA 86:7706-10 (1989); and Methods Enzymol 183:281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity and to be disclosed herein.

Nucleic acids that encode protein sequences disclosed herein, as well as variants and fragments thereof, are also disclosed. These sequences include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequences.

Fragments and partial sequences of proteins may be useful in methods described herein. As with all peptides and proteins, including fragments thereof, it is understood that additional modifications in the amino acid sequences of the proteins disclosed herein can occur that do not alter the nature or function of the peptides and proteins. It will be appreciated that the only limitation on these is practical, they must comprise the necessary functional elements (e.g., tunnel-forming capability) for use in the relevant embodiment. Such modifications include conservative amino acids substitutions and are discussed in greater detail below.

The following table provides non-limiting examples of properties of amino acids that may assist a skilled artisan in determining how to select amino acids for modifications of proteins (e.g., protein pores) as described herein.

TABLE 4

Amino Acid Properties

| Amino Acid | Percent Buried Residues[a] (%) | Average Volume[b] (Å$^3$) | van der Waals volume[c] (Å$^3$) | Accessible surface area[d] (Å$^2$) | Ranking of amino acid polarities[e] |
|---|---|---|---|---|---|
| alanine | 38 (12) | 92 | 67 | 67 | 9 (7) |
| arginine | 0 | 225 | 148 | 196 | 15 (19) |
| asparagine | 10 (2) | 135 | 96 | 113 | 16 (16) |
| aspartic acid | 14.5 (3) | 125 | 91 | 106 | 19 (18) |
| cysteine | 47 (3) | 106 | 86 | 104 | 7 (8) |
| glutamine | 6.3 (2.2) | 161 | 114 | 144 | 17 (14) |
| glutamic acid | 20 (2) | 155 | 109 | 138 | 18 (17) |
| glycine | 37 (10) | 66 | 48 | | 11 (9) |
| histidine | 19 (1.2) | 167 | 118 | 151 | 10 (13) |
| isoleucine | 65 (12) | 169 | 124 | 140 | 1 (2) |
| leucine | 41 (10) | 168 | 124 | 137 | 3 (1) |
| lysine | 4.2 (0.1) | 171 | 135 | 167 | 20 (15) |
| methionine | 50 (2) | 171 | 124 | 160 | 5 (5) |
| phenylalanine | 48 (5) | 203 | 135 | 175 | 2 (4) |
| proline | 24 (3) | 129 | 90 | 105 | 13 (—) |
| serine | 24 (8) | 99 | 73 | 80 | 14 (12) |
| threonine | 25 (5.5) | 122 | 93 | 102 | 12 (11) |
| tryptophan | 23 (1.5) | 240 | 163 | 217 | 6 (6) |
| tyrosine | 13 (2.2) | 203 | 141 | 187 | 8 (10) |
| valine | 56 (15) | 142 | 105 | 117 | 4 (3) |

[a]This column represents the tendency of an amino acid to be buried (defined as <5% of residue available to solvent) in the interior of a protein and is based on the structures of nine proteins (total of ~2000 individual residues studied, with 587 (29%) of these buried). Values indicate how often each amino acid was found buried, relative to the total number of residues of this amino acid found in the proteins. Values in parentheses indicate the number of buried residues of this amino acid found relative to all buried residues in the proteins. Data from BioTechnology 8: 308 (1990); for other calculation methods with similar results, see Nature 277: 491 (1979); and Science 229: 834 (1985).

[b]Average volume ($V_r$) of buried residues, calculated from the surface area of the side chain. Annu Rev Biophys Bioeng 6: 151 (1977); Protein Eng 2: 329 (1989).

[c]Data from Darby N. J. and Creighton T. E. Protein structure. In In focus (ed. D. Rickwood), p. 4. IRL Press, Oxford, United Kingdom (1993).

[d]Total accessible surface area (ASA) of amino acid side chain for residue X in a Gly-X-Gly tripeptide with the main chain in an extended conformation. J Mol Biol 196: 641 (1987).

[e]Values shown represent the mean ranking of amino acids according to the frequency of their occurrence at each sequence rank for 38 published hydrophobicity scales. Protein Eng 11: 153 (1998). Although the majority of these hydrophobicity scales are derived from experimental measurements of chemical behavior or physicochemical properties (e.g., solubility in water, partition between water and organic solvent, chromatographic migration, or effects on surface tension) of isolated amino acids, several "operational" hydrophobicity scales based on the known environment characteristics of amino acids in proteins, such as their solvent accessibility or their inclination to occupy the core of proteins (based on the position of residues in the teritary structures as observed by x-ray crystallography or NMR) are included. The lower rankings represent the most hydrophobic amino acids, and higher values represent the most hydrophilic amino acids. For comparative purposes, the hydrophobicity scale of Radzicka and Wolfenden, Biochem 27: 1664 (1988) is shown in parentheses. That scale was derived from the measured hydration potential of amino acids that is based on their free energies of transfer from the vapor phase to cyclohexane, 1-octanol, and neutral aqueous solution.

Alternatively, one may consider the hydropathic index of amino acids. Each amino acid has been assigned a hydropathic index on the basis of their hydrophobicity and/or charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and/or arginine (−4.5). The importance of the hydropathic amino acid index in conferring interactive biological function on a protein is generally understood in the art. It is known that certain amino acids may be substituted for other amino acids having a similar hydropathic index and/or score and/or still retain a similar biological activity. In making changes based upon the hydropathic index, the substitution of amino acids whose hydropathic indices may be within ±2; within ±1, or within ±0.5.

It also is understood in the art that the substitution of like amino acids can be made effectively on the basis of hydrophilicity. As detailed in U.S. Pat. No. 4,554,101, incorporated herein by reference, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, it is contemplated that the substitution of amino acids whose hydrophilicity values may be within ±2, within ±1, or those within ±0.5.

Any mutant protein may comprise a conservative amino acid substitution as compared to a wild-type Msp porin or monomer. Any substitution mutation is conservative in that it minimally disrupts the biochemical properties of the protein. Non-limiting examples of mutations that are introduced to substitute conservative amino acid residues include: positively-charged residues (e.g., H, K, and R) substituted with positively-charged residues; negatively-charged residues (e.g., D and E) substituted with negatively-charged residues; neutral polar residues (e.g., C, G, N, Q, S, T, and Y) substituted with neutral polar residues; and neutral non-polar residues (e.g., A, F, I, L, M, P, V, and W) substituted with neutral non-polar residues. Conservative substitutions may made in accordance with the following Table 5. Nonconservative substitutions can be made as well (e.g., proline for glycine).

TABLE 5

Exemplary Amino Acid Substitutions

| Amino Acid | Substitutions |
|---|---|
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |

TABLE 5-continued

Exemplary Amino Acid Substitutions

| Amino Acid | Substitutions |
|---|---|
| Tyr | Trp, Phe, His |
| Val | Ile, Leu, Met |

A nanopore will typically be able to be inserted in a lipid bilayer or other thin film, and these techniques are well known in the art, as explained herein. In addition, U.S. Pat. No. 6,746,594, incorporated herein by reference, describes a variety of lipid bilayers and thin films, including inorganic materials that may be employed with respect to the nanopores discussed herein. Methods, apparatuses, and techniques described in U.S. Pat. No. 6,267,872, incorporated herein by reference in its entirety, are also employable with respect to nanopores discussed herein.

An optional lipid membrane that may be employed in some embodiments is an artificial membrane comprising a mycolic acid as described in U.S. application Ser. No. 61/307,441 and its related international application entitled, "Artificial Mycolic Acid Membranes," by Jens H. Gundlach, Ian M. Derrington, and Kyle W. Langford, filed in the U.S. Receiving Office on Feb. 23, 2011, and published as WO 2011/106456, each of which is incorporated by reference in its entirety. Mycolic acids are high molecular weight a-branched, (β-hydroxy fatty acids that are components of the cell envelopes of all Mycobacteria. Mycolic acids contain a carboxylic acid headgroup with two hydrophobic tails of unequal length. Mycolic acids have the basic structure $R^2CH(OH)CHR^1COOH$, where $R_1$ is a $C_{20}$-$C_{24}$ linear alkane and $R^2$ is a more complex structure of 30-60 carbon atoms that may contain various numbers of carbon-carbon double bonds, cyclopropane rings, methyl branches or oxygen functions such as carbonyl, carboxylic acid, and methoxy groups. The structure of mycolic acids varies by families and species.

In the mycobacterial cell envelope, mycolic acids are present as free lipids, such as trehalose dimycolate (TDM) or cord factor and trehalose monomycolate (TMM). They may also be esterified to the terminal penta-arabinofuranosyl units of arabinogalactan, a peptidoglycan-linked polysaccharide. Herein, a mycolic acid may be further defined as any of these variants. In some embodiments, a mycolic acid is further defined as a trehalose-modified mycolic acid that may be naturally-occurring or synthetic, which are known in the art. See, e.g., U.S. Pat. Nos. 4,307,229, 4,720,456, 5,006,514, and 5,049,664, each of which is incorporated herein by reference in its entirety. The presence of such long-chain fatty acids is largely responsible for the high hydrophobicity and very low permeability of the mycobacterial cell envelope. Mycolic acids have been reported in bacterial species other than *Mycobacterium*, e.g., *Corynebacterium* and *Nocardia*. Consequently, three major categories of mycolic acids are distinguished (The Merck Index, 1989), namely:

i) corynomycolic acids ($C_{28}$-$C_{40}$ acyl chain length)
ii) nocardomycolic acids ($C_{40}$-$C_{60}$ acyl chain length) and
iii) mycobacterial mycolic acids ($C_{60}$-$C_{90}$ acyl chain length).

A detailed description of the structures of MA, motifs, and variations is provided in Prog. Lipid Res 37:143 (1998). MA may be purchased, such as from Sigma Aldrich, or prepared as is known in the art. See, e.g., U.S. Pat. No. 6,171,830, incorporated herein by reference in its entirety. In some embodiments, mycolic acids are derived from *M. tuberculosis.*

The definition of mycolic acids also includes modified mycolic acids. Accordingly, artificial membranes may comprise one or more modified mycolic acids. For example, mycolic acids may be modified by crosslinking mycolic acids. Artificial mycolic acid membranes may be made to be more gel-like and stable by end-group polymerization or by crosslinking of internal groups of mycolic acids. Methods of crosslinking similar to methods of crosslinking dipalmitoylphosphatidylcholine (DPhPC) or other lipids, as is known in the art, may be employed to prepare modified mycolic acids. See, e.g., A. Singh and J. M. Schnur, "Polymerizable Phospholipids" in Phospholipids Handbook, C. Cevc, ed., Marcel Dekker Inc., NY, pp 233-287 (1993). A membrane may comprise one or more types of mycolic acids (that is, mixtures of mycolic acids). In some embodiments, a membrane comprises about, at least about, or at most about 1%, 2%, 5%, 10%, 15%, 20%, 25%, 30%, 35%, 40%, 45%, 50%, 55%, 60%, 65%, 70%, 75%, 80%, 85%, 90%, 95%, 98%, 99%, or more mycolic acids, or any range derivable therein. In some embodiments, a membrane comprises 100% mycolic acids. Artificial membranes comprising a mycolic acid may also comprise lipids other than mycolic acid, including synthetic and naturally occurring lipids. U.S. Pat. No. 7,514,267, incorporated herein by reference in its entirety, describes a variety of lipids.

As used herein, an "unsupported membrane" is a membrane spanning the opening of an aperture with no support on either side along the surface of the membrane. The membrane has liquid, gas, or vacuum on either or both sides, but is not in contact with a solid (substrate) on either side. As used herein, a "tethered membrane" is a membrane in which the headgroups of mycolic acids are attached, or tethered, to a substrate (e.g., plastic, glass, chip, bead). Methods of attaching lipids to substrates to form tethered membranes are well known in the art through chemical modification of headgroups, and such methods may be used to similarly modify and attach headgroups of mycolic acids. By "artificial," it is meant that the membranes are not naturally occurring, but are instead man-made.

In any embodiment herein, an artificial membrane comprising a mycolic acid may be unsupported or tethered. A mycolic acid may be further defined as a modified mycolic acid. A modified mycolic acid may be a crosslinked mycolic acid. A mycolic acid may be further defined as not a modified mycolic acid. In some embodiments, a membrane has average thickness ranging from about 5 to about 22 nm. Methods of measuring thickness of membranes are well-known in the art. In some embodiments, a membrane has an average rupture voltage of about 2.0 V when voltage applied across the membrane is ramped at about 100 mV/s in the presence of a 1.0 M KCl solution prepared with deionized water, buffered to pH 8.0±0.05 with 10 mM HEPES. In some embodiments, a membrane has an ability to withstand voltages greater than 1 V for greater than several hours in the presence of a 1.0 M KCl solution prepared with deionized water, buffered to pH 8.0±0.05 with 10 mM HEPES. In some embodiments, a membrane has an ability to withstand voltages greater than 1 V for at least about 2, 3, 4, or 5 or more hours, or any range derivable therein, in the presence of a 1.0 M KCl solution prepared with deionized water, buffered to pH 8.0±0.05 with 10 mM HEPES. In some embodiments, a membrane has a resistance to rupture when buffers on cis or trans sides are removed. A membrane may be formed and reformed when exposed to pH 2 to pH 9 buffer presented to its cis side. In some embodiments, a membrane may be formed and reformed at temperatures exceeding 55° C.

Also provided is a method of making an artificial unsupported membrane comprising a mycolic acid, comprising: (a) pretreating an aperture of about 500 nm to about 500 μm in diameter with one or more coats of a mycolic acids-hexane mixture and removing the hexane to provide dry mycolic acids; (b) applying a hydrocarbon solvent to the dry mycolic acids followed by heating to promote hydrocarbon solvent incorporation to provide a mycolic acids-hydrocarbon solvent composition; (c) placing the aperture between a first liquid conductive medium and a second liquid conductive medium; (d) applying the mycolic acids-hydrocarbon solvent composition to the aperture while monitoring an ion current through the aperture until aperture resistance increases to above 1 TΩ, followed by forcing one of the liquid conductive mediums through the aperture from the trans side to eliminate ion current blockage as needed; and (e) placing an air bubble over the aperture followed by retraction of the air bubble, wherein membrane formation is indicated by the aperture resistance increasing to above 1 TΩ, and wherein bilayer membrane formation is indicated if a nanopore can form within the membrane. The hydrocarbon solvent may be hexadecane or hexadecene or any other hydrocarbon solvent that may be incorporated into the membrane. The type of hydrocarbon solvent employed depends on the temperature at which one wants to prepare the membrane.

In some embodiments, a plurality of nanopores are comprised in an artificial membrane comprising a mycolic acid. For example, 2, 3, 4, 5, 10, 20, 200, 2000, or more may be comprised in a membrane.

Optionally, 2, 3, 4, 5, 10, 20, 200, 2000, or more nanopores are comprised in a membrane, bilayer, or thin film. Indeed, anywhere from 2 to $10^{10}$ nanopores may be employed in embodiments described herein. Such a plurality of nanopores may be in the form of clusters of nanopores. Clusters may be randomly assembled or may adopt a pattern. As used herein, a "cluster" refers molecules that are grouped together and move as a unit, but are not covalently bound to one another.

Optionally, nanopores do not gate spontaneously. "To gate" or "gating" refers to the spontaneous change of electrical conductance through the opening of the protein that is usually temporary (e.g., lasting for as few as 1-10 milliseconds to up to a second). Long lasting gating events can often be reversed by changing the polarity. Under most circumstances, the probability of gating increases with the application of higher voltages. Gating and the degree of conductance through the opening change are highly variable among nanopores, depending on, for example, the make-up of opening (e.g., the vestibule and constriction zone of Msp porins) as well as the properties of the liquid medium in which the protein is submerged. Typically, the protein becomes less conductive during gating, and conductance may permanently stop (i.e., the opening may permanently shut) as a result, such that the process is irreversible. Optionally, gating refers to the conductance through the opening of a nanopore spontaneously changing to less than 75% of its open state current.

Various conditions such as light and the liquid medium that contacts a nanopore, including its pH, buffer composition, detergent composition, and temperature, may affect the behavior of the nanopore, particularly with respect to its conductance through the tunnel as well as the movement of an analyte with respect to the tunnel, either temporarily or permanently.

As an alternative to or in addition to "comprising," any embodiment herein may recite "consisting of." The transitional phrase "consisting of" excludes any element, step, or ingredient not specified in the claim.

Any embodiment herein may optionally exclude any other embodiment herein.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value. In any embodiment discussed in the context of a numerical value used in conjunction with the term "about," it is specifically contemplated that the term about can be omitted.

Following long-standing patent law, the words "a" and "an," when used in conjunction with the word "comprising" in the claims or specification, denotes one or more, unless specifically noted.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed. It is therefore contemplated that any embodiment discussed in this specification can be implemented with respect to any method, system, or composition, etc., described herein, and vice versa. For example, any nanopore described herein can be employed in any method described herein.

Examples

Example 1: Materials and Methods for Example 1-7

Unless otherwise noted, the M1-NNN-MspA nanopore was used in the Examples below. Preparation of this nanopore is described in U.S. Provisional Application No. 61/098,938 and its related PCT application, WO 2010/034018, each of which is incorporated herein by reference in its entirety. See also Proc Natl Acad Sci 105:20647 (2008).

DNA was synthesized by Integrated DNA Technologies, Inc. with no additional purification for hairpin DNA, or with PAGE purification for some of the DNA. DNA concentrations ranged from ~10 μM to 100 μM. To prevent self-dimerization, hairpin DNA was prepared by heating it to 90 C for 1 minute, cooling in a −8 C freezer for an additional minute, and then returning it to room temperature before use.

Hairpin DNA sequences examining MspA's nucleotide sensitivity had the same 14 base duplex region and 6 nt loop. 5' GCTGGCTCTGTTGC TCTCTC GCAACAGAGCCAGC <tail>3' [SEQ ID NO:4]. The underlines indicate duplex formation between complementary bases. The hairpin tail sequences are presented in Tables A and B. If residual currents were sufficiently similar to other DNA strands, experiments were run with similar concentration of either poly-dA or poly-dC to provide a residual current calibration. This calibration reduced minor experimental variation in current levels due to Nernst-potentials and buffer evaporation.

TABLE A

HAIRPIN SEQUENCES

| DUPLEX 5' GCT GGC TCT GTT GCT CTC TCG CAA CAG AGC CAG C TAIL | | Seq ID # | mean of Gauss mean of $I_{res}$ (pA) | mean of Gauss width of $I_{res}$ (pA) | s.e.m. of Gauss means (pA) | # transloc. | # exp |
|---|---|---|---|---|---|---|---|
| $(dA)_{50}$: | AAA AAA AAA AAA AAA AAA AAA AAA AAA AAA AAA AAA AAA AAA AAA AAA AA 3' | 10 | 65.5 | 1.5 | 1.0 | 3257 | 7 |
| $(dC)_{50}$: | CCC CCC CCC CCC CCC CCC CCC CCC CCC CCC CCC CCC CCC CCC CCC CCC CC 3' | 11 | 48.4 | 1.1 | 1.4 | 1830 | 8 |
| $(dT)_{50}$: | TTT TTT TTT TTT TTT TTT TTT TTT TTT TTT TTT TTT TTT TTT TTT TTT TT 3' | 12 | 41.9 | 1.2 | 1.1 | 2407 | 4 |
| $(dG)_3(dA)_{47}$: | GGG AAA AAA AAA AAA AAA AAA AAA AAA AAA AAA AAA AAA AAA AAA AAA AA 3' | 27 | 59.4 | 1.2 | 0.8 | 2938 | 5 |
| $(dC)_4(dA)_{46}$: | CCC CAA AAA AAA AAA AAA AAA AAA AAA AAA AAA AAA AAA AAA AAA AAA AA 3' | 28 | 50.0 | 0.9 | 1.1 | 914 | 4 |
| $(dA)_3(dC)_4(dA)_{43}$: | AAA CCC CAA AAA AAA AAA AAA AAA AAA AAA AAA AAA AAA AAA AAA AAA AA 3' | 29 | 65.4 | 1.3 | 1.7 | 1186 | 2 |

TABLE A-continued

| HAIRPIN SEQUENCES | | | | | | | | |
|---|---|---|---|---|---|---|---|---|
| | DUPLEX 5' GCT GGC TCT GTT GCT CTC TCG CAA CAG AGC CAG C TAIL | Seq ID # | mean of Gauss mean of $I_{res}$ (pA) | mean of Gauss width of $I_{res}$ (pA) | s.e.m. of Gauss means (pA) | # transloc. | # exp |
| $(dA)_6(dC)_4(dA)_{40}$: | AAA AAA CCC CAA AAA AAA AAA AAA AAA AAA AAA AAA AAA AAA AAA AAA AA 3' | 30 | 65.7 | 1.7 | 2.1 | 1094 | 3 |
| $(dA)_3$ rand1: | AAA TAC GCA TAC ATC CTA AGA ACT CAG ACT ACC TCC CAA TAA ATC CAC AC 3' | 31 | 64.1 | 1.5 | 0.5 | 1073 | 3 |
| $(dA)_3$ rand2: | AAA TCA GAC TAC CTC CCA ATA AAT CCG CAG CAA TCC TCA CAC CTA ATA AT 3' | 32 | 65.6 | 1.6 | 0.5 | 822 | 3 |
| $(dC)_3$ rand1: | CCC TAC GCA TAC ATC CTA AGA ACT CAG ACT ACC TCC CAA TAA ATC CAC AC 3' | 33 | 48.6 | 0.8 | 0.2 | 1319 | 4 |
| $(dC)_3$ rand2: | CCC TCA GAC TAC CTC CCA ATA AAT CCG CAG CAA TCC TCA CAC CTA ATA AT 3' | 34 | 48.6 | 0.9 | 0.6 | 1325 | 4 |
| $dC(dA)_{49}$: | CAA AAA AAA AAA AAA AAA AAA AAA AAA AAA AAA AAA AAA AAA AAA AAA AA 3' | 35 | 56.9 | 1.7 | 2.0 | 3198 | 6 |
| $dAdC(dA)_{48}$: | ACA AAA AAA AAA AAA AAA AAA AAA AAA AAA AAA AAA AAA AAA AAA AAA AA 3' | 36 | 52.1 | 1.2 | 0.3 | 2597 | 3 |
| $(dA)_2dC(dA)_{47}$: | AAC AAA AAA AAA AAA AAA AAA AAA AAA AAA AAA AAA AAA AAA AAA AAA AA 3' | 17 | 61.4 | 1.3 | 0.4 | 1550 | 2 |
| $dA(dC)_{49}$: | ACC CCC CCC CCC CCC CCC CCC CCC CCC CCC CCC CCC CCC CCC CCC CCC CC 3' | 37 | 50.0 | 1.4 | 1.5 | 4957 | 4 |
| $dCdA(dC)_{48}$: | CAC CCC CCC CCC CCC CCC CCC CCC CCC CCC CCC CCC CCC CCC CCC CCC CC 3' | 38 | 51.5 | 0.9 | 0.6 | 5090 | 6 |
| $(dC)_2dA(dC)_{47}$: | CCA CCC CCC CCC CCC CCC CCC CCC CCC CCC CCC CCC CCC CCC CCC CCC CC 3' | 20 | 49.8 | 1.1 | 1.1 | 4076 | 4 |
| $dT(dA)_{49}$: | TAA AAA AAA AAA AAA AAA AAA AAA AAA AAA AAA AAA AAA AAA AAA AAA AA 3' | 39 | 46.6 | 1.2 | 0.7 | 2408 | 4 |
| $dAdT(dA)_{48}$: | ATA AAA AAA AAA AAA AAA AAA AAA AAA AAA AAA AAA AAA AAA AAA AAA AA 3' | 40 | 54.4 | 1.4 | 0.9 | 4760 | 5 |
| $(dA)_2dT(dA)_{47}$: | AAT AAA AAA AAA AAA AAA AAA AAA AAA AAA AAA AAA AAA AAA AAA AAA AA 3' | 23 | 60.7 | 1.6 | 1.2 | 2203 | 4 |
| $dA(dT)_{49}$: | ATT TTT TTT TTT TTT TTT TTT TTT TTT TTT TTT TTT TTT TTT TTT TTT TT 3' | 41 | 55.1 | 1.0 | 1.0 | 2010 | 5 |
| $dTdA(dT)_{48}$: | TAT TTT TTT TTT TTT TTT TTT TTT TTT TTT TTT TTT TTT TTT TTT TTT TT 3' | 42 | 43.8 | 0.9 | 1.4 | 2218 | 4 |
| $(dT)_2dA(dT)_{47}$: | TTA TTT TTT TTT TTT TTT TTT TTT TTT TTT TTT TTT TTT TTT TTT TTT TT 3' | 26 | 42.3 | 1.0 | 1.3 | 1430 | 3 |
| $dG(dA)_{49}$: | GAA AAA AAA AAA AAA AAA AAA AAA AAA AAA AAA AAA AAA AAA AAA AAA AA 3' | 43 | 61.9 | 1.9 | 0.7 | 4036 | 5 |
| $dAdG(dA)_{48}$: | AGA AAA AAA AAA AAA AAA AAA AAA AAA AAA AAA AAA AAA AAA AAA AAA AA 3' | 44 | 63.2 | 1.6 | 0.3 | 4213 | 3 |
| $(dA)_2dG(dA)_{47}$: | AAG AAA AAA AAA AAA AAA AAA AAA AAA AAA AAA AAA AAA AAA AAA AAA AA 3' | 45 | 62.5 | 1.9 | 0.8 | 4461 | 3 |

TABLE B

HAIRPIN SEQUENCES

| DUPLEX | TAIL | Seq ID # | # bp | GC % | mean of Gauss mean of Ires (pA) | mean of Gauss width of Ires (pA) | s.e.m. of Gauss width of Ires (pA) | # transloc | # exp |
|---|---|---|---|---|---|---|---|---|---|
| 5' TCT GGC TCT GTT GCT CTC TCG CAA CAG AGC CAG A | $(dA)_{50}$-3' | 46 | 14 | 57 | 70.8 | 8.1 | 4.5 | 2616 | 4 |
| 5' CCT GGC TCT GTT GCT CTC TCG CAA CAG AGC CAG G | $(dA)_{50}$-3' | 47 | 14 | 64 | 76.5 | 8.4 | 1.2 | 3417 | 4 |
| 5' ACT GGC TCT GTT GCT CTC TCG CAA CAG AGC CAG T | $(dA)_{50}$-3' | 48 | 14 | 57 | 63.6 | 1.9 | 0.6 | 3967 | 4 |
| 5' GCC GGC TCT GGT GCT CTC TCG CAC CAG AGC CGG C | $(dA)_{50}$-3' | 49 | 14 | 79 | 67.5 | 0.2 | 0.5 | 1819 | 3 |
| 5' GCT GTC TGT TGC TCT CTC GCA ACA GAC AGC | $(dA)_{50}$-3' | 50 | 12 | 58 | 66.0 | 1.5 | 2.3 | 3583 | 3 |
| 5' GCT CTG TTG CTC TCT CGC AAC AGA GC | $(dA)_{50}$-3' | 51 | 10 | 60 | 67.6 | 1.5 | 2.0 | 5305 | 6 |
| 5' GCT GTT GCT CTC TCG CAA CAG C | $(dA)_{50}$-3' | 52 | 8 | 63 | 68.4 | 1.9 | 1.9 | 4413 | 6 |

The DNA used in DI sequencing were as follows:

3'ATGC5' [SEQ ID NO: 1]:

[SEQ ID NO: 5]
5' GCAACAGAGCCAGC CCC GCAACAGAGCCAGC GGA

GCAACAGAGCCAGC TTT GCAACAGAGCCAGC AAA $A_{32}$ 3'

3'TACG5' [SEQ ID NO: 2]:

[SEQ ID NO: 6]
GCAACAGAGCCAGC GGA GCAACAGAGCCAGC CCC

GCAACAGAGCCAGC AAA GCAACAGAGCCAGC TTT $A_{32}$ 3'

BLIND:

[SEQ ID NO: 7]
5' GCAACAGAGCCAGC CCC GCAACAGAGCCAGC AAA

GCAACAGAGCCAGC CCC GCAACAGAGCCAGC TTT

GCAACAGAGCCAGC GGA $A_{15}$ 3'.

The underlined regions formed duplexes with oligonucleotides of sequence 5' GCTGGCTCTGTTGC 3' [SEQ ID NO:8]. The oligonucleotides and synthesized DI DNA were combined in a molar ratio >32:1, annealed by heating to 95° C. for 5 minutes and then gradually cooled to 23±1° C.

Pores were established with previously described methods (U.S. Provisional Application Ser. No. 61/098,938 and its related PCT application, WO 2010/034018, each incorporated herein in its entirety). Briefly, lipid bilayers were formed from either 1,2-diphytanoyl-sn-glycerol-3-phosphocholine, 1,2-diphytanoyl-sn-glycero-3-phosphate (Avanti Polar Lipids, Inc.) or from equal mixtures thereof. The bilayer spanned a horizontal ~20 micron diameter aperture in Teflon®. M1-NNN-MspA was added to the grounded side of the bilayer at a concentration of ~2.5 ng/ml. An Axopatch™-1B or 200B patch clamp amplifier (Axon Instruments, now of Molecular Devices, Inc.) applied a voltage across the bilayer and measured the ionic currents. The analog signal was low-pass filtered at 10, 50 or 100 kHz with a 4-pole Bessel filter and was then digitized at five times the low-pass filter frequency. Data acquisition was controlled with custom software written in LabWindows®/CVI (National Instruments). For display purposes, the residual current traces were digitally filtered at 2 kHz. All experiments were performed at 23±1° C. in 1 M KCl, 10 mM HEPES/KOH buffered at pH 8. Data was analyzed with custom software written in Matlab® (The Mathworks®) (see Example 7 below).

Example 2: Nucleotide Identification by MspA

Translocation experiments were conducted with DNA that forms a 14-base pair hairpin duplex and has a 50-nucleotide ssDNA 'tail' (see Table A). When a voltage is applied across the pore, the long single-stranded tail facilitates capture and insertion of the DNA into the pore's constriction (FIGS. 2A-2D). At a driving voltage of 180 mV, the hairpin duplex dissociates after ~10 ms. During the time that the hairpin tail is held, the measured residual ionic current ($I_{res}$) depends strongly on the composition of the ssDNA section residing in the confining constriction of the pore. Once the duplex dissociates, the DNA completes translocation to the lower potential chamber at speeds faster than 1 nt/μs.

Figure 3A:
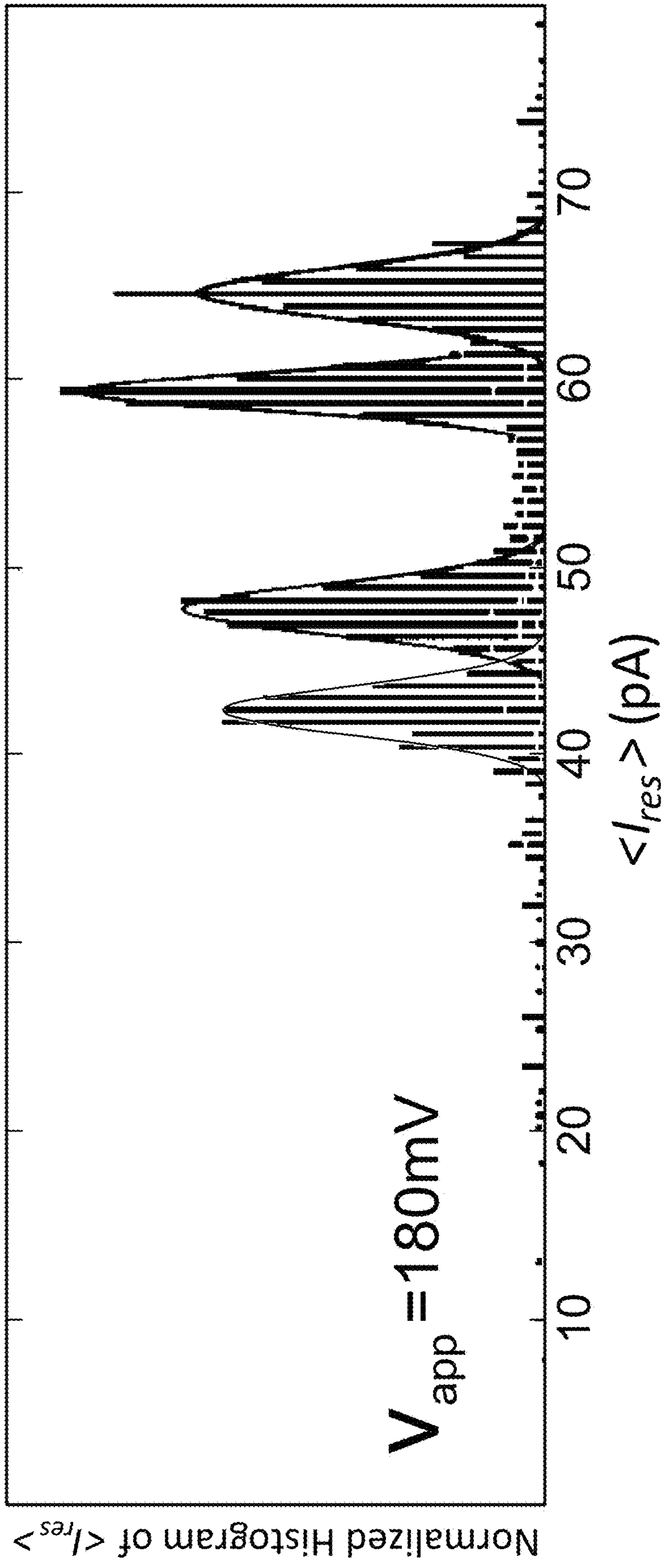
FIGS. 3A and 3B provide example histograms of the averaged residual ion currents, $<I_{res}>$ that are shown for different "hompolymer" single stranded tails of a 14 base pair hairpin (hp). Data were taken at (a) 180 mV and (b) 140 mV. The translocations included in FIG. 3A have durations longer than 1 millisecond and reveal distinguishable and well-resolved current levels. The average of the fitted Gaussian mean of a number of experiments are given in the examples below. There were at least 4 experimental repetitions with each of the hairpin DNA. The reduction in widths at 140 mV is due to increased time averaging as the dissociation times are nearly 30× longer than the dissociation times at 180 mV. Additional information may be found in Table A.
Figure 3B:
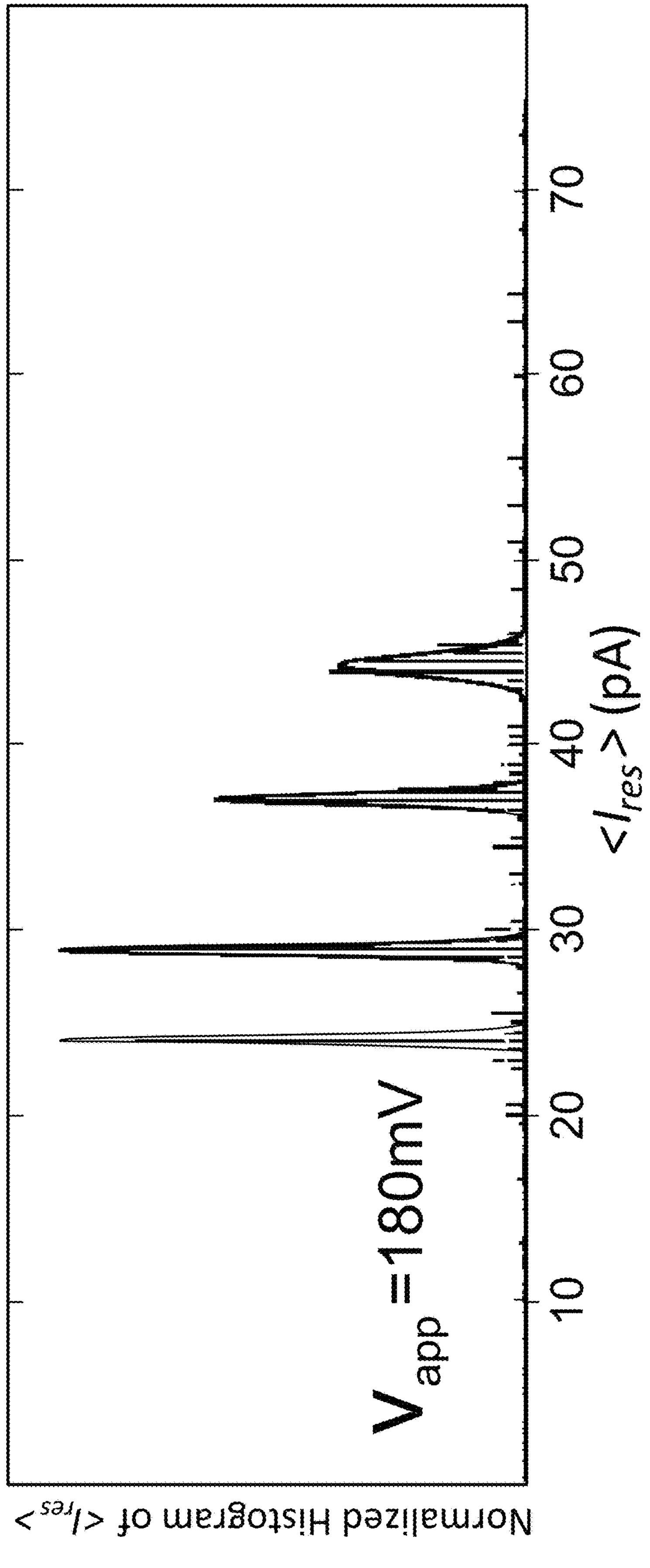
Figure 4A:
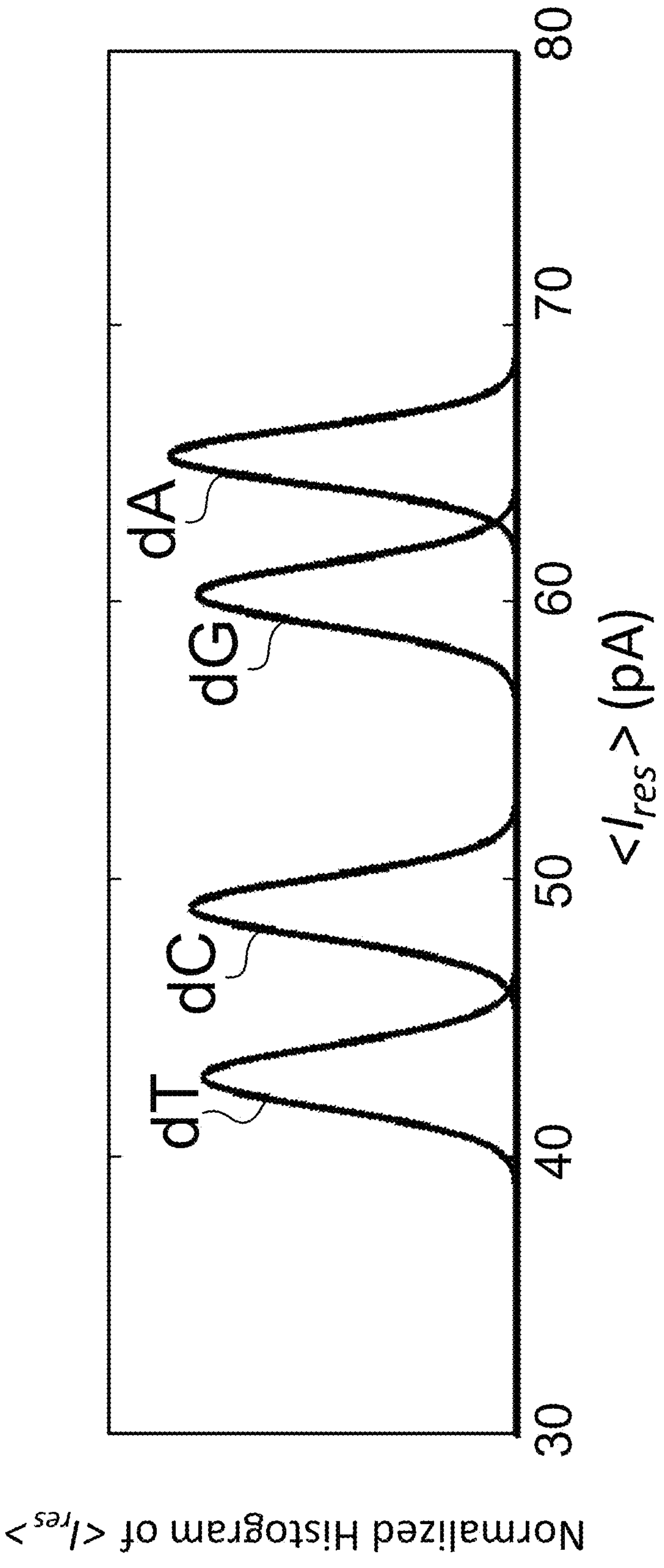
FIGS. 4A, 4B, 4C, and 4D provide residual current histograms due to single nucleotide substitutions in an otherwise poly-dA hairpin tail.
Figure 4B:
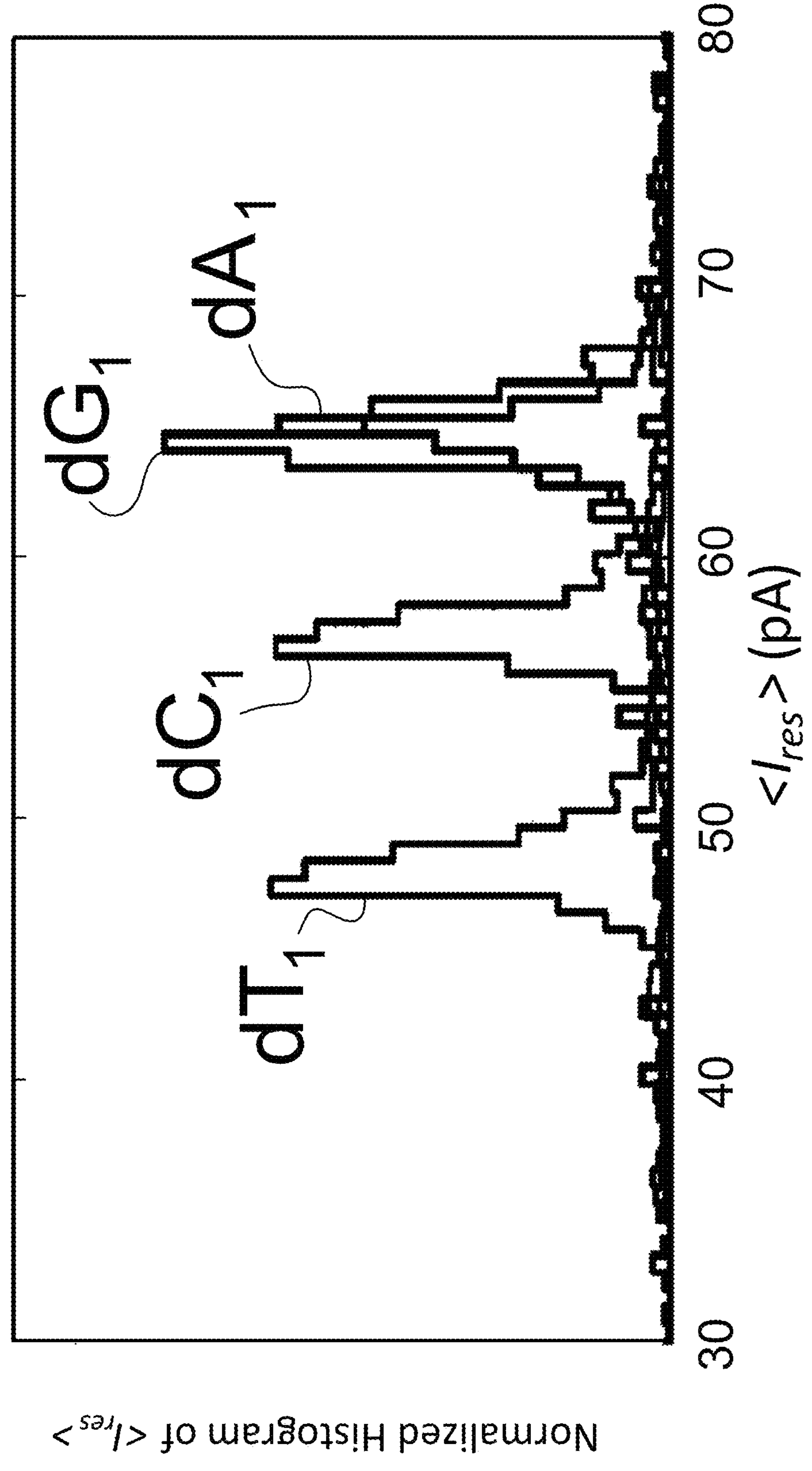
Figure 4C:
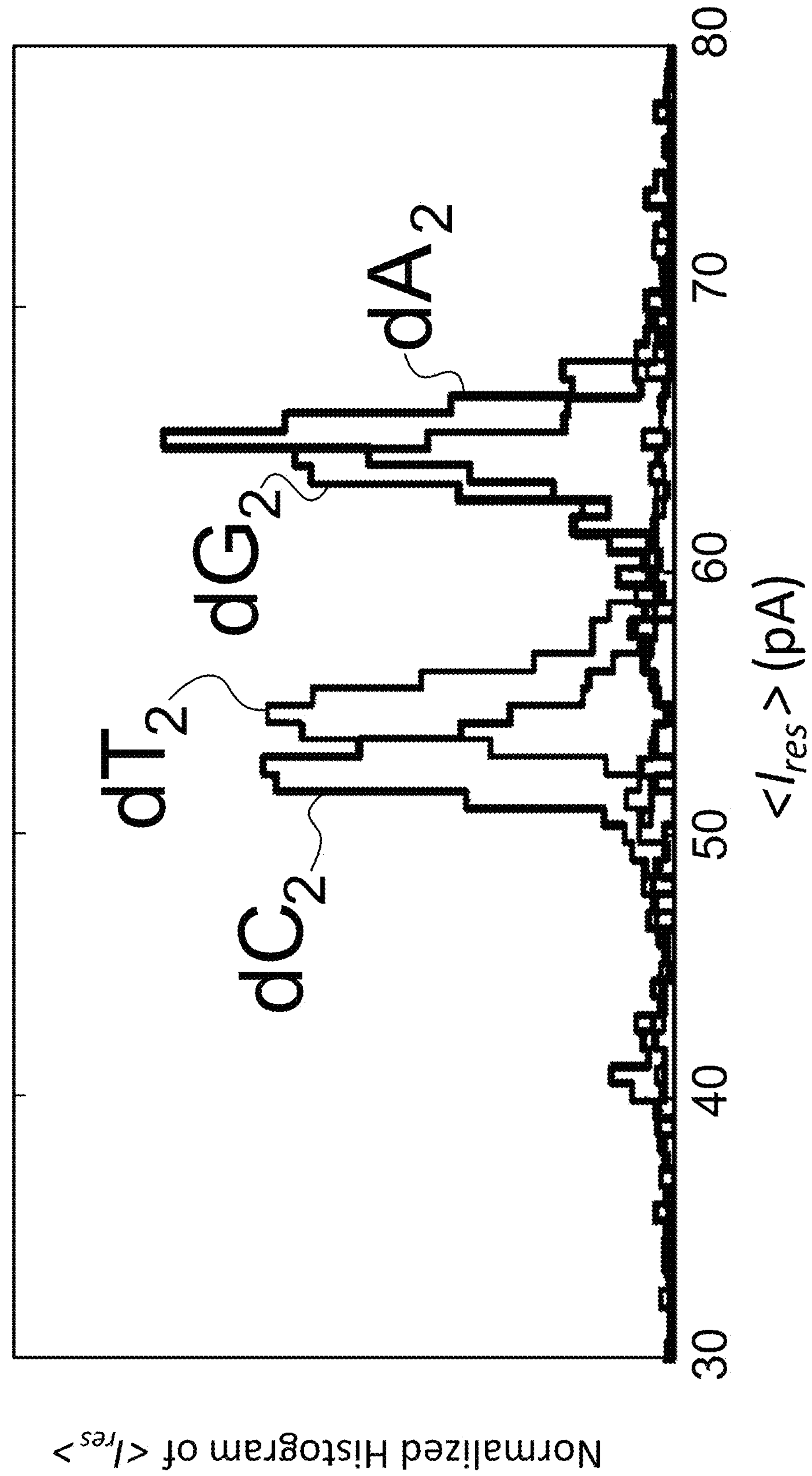
Figure 4D:
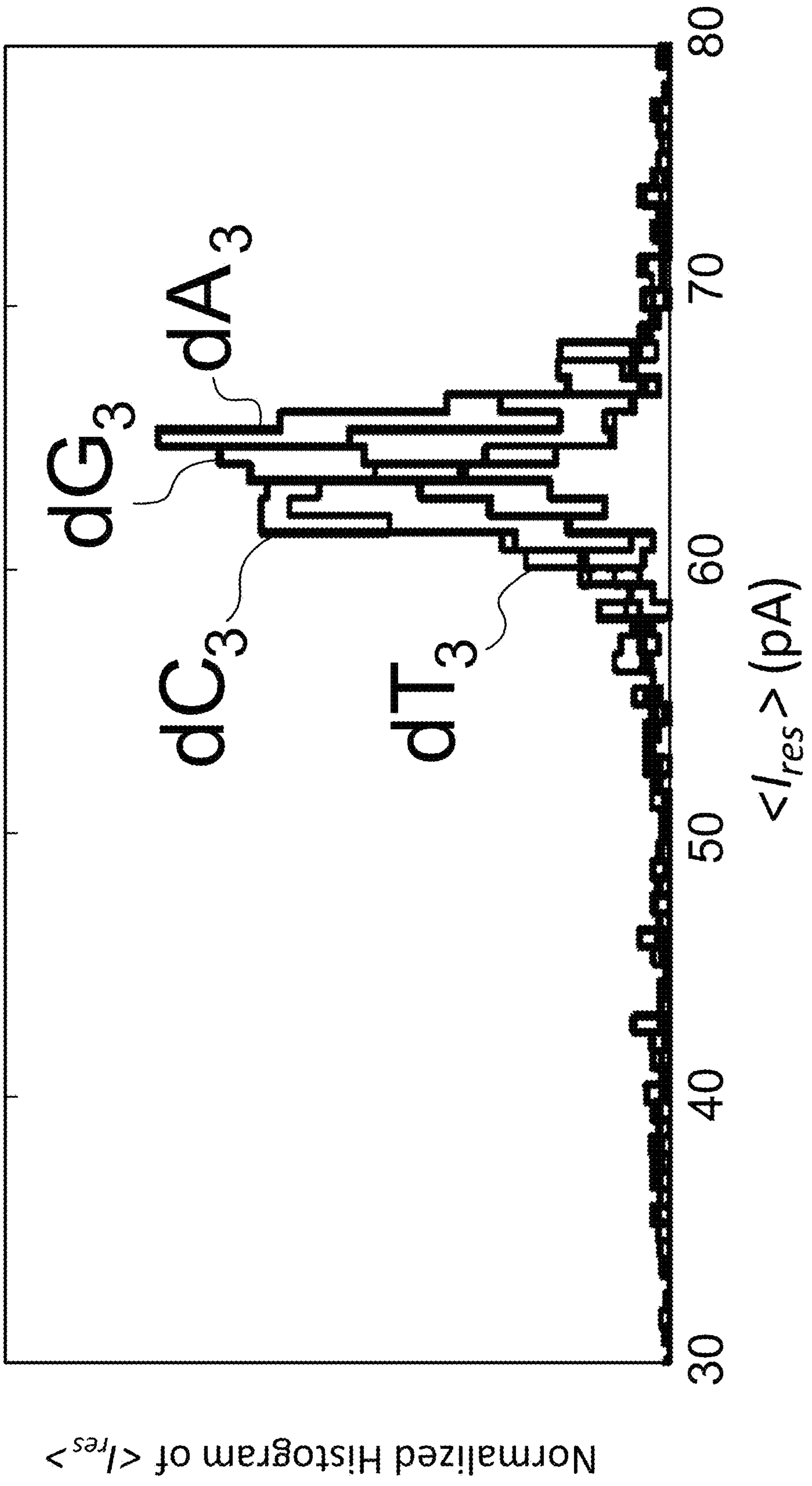

First, characteristic residual currents associated with the four bases were determined by using the 'homopolymer' DNA hairpin tails $(dA)_{50}$ [SEQ ID NO:10], $(dC)_{50}$ [SEQ ID NO:11], $(dT)_{50}$ [SEQ ID NO:12], and $(dG)_3$, $(dA)_{47}$ [SEQ ID NO:13] held in M1-NNN-MspA. Note that $(dG)_3$ $(dA)_{47}$ [SEQ ID NO:54], instead of $(dG)_{50}$ [SEQ ID NO:14], was used because of G-tetrad formation. For each polynucleotide tail, the histograms of the average residual current reveal unique values at an applied voltage of 180 mV (FIGS. 3A, 3B). The Gaussian mean (μ) and half-width (G) of the residual ion currents caused by $(dA)_{50}$ [SEQ ID NO:10] tails was $I_{dA}$=65.5±1.5 pA (μ±σ, averaged over N=7 experiments with different pores, n=3257 total translocations). The tails $(dG)_3$ $(dA)_{47}$ [SEQ ID NO:54], $(dC)_{50}$ [SEQ ID NO:11], and $(dT)_{50}$ [SEQ ID NO:12] yield residual ion currents of $I_{dG}$=59.4±1.2 pA (N=5, n=2938), $I_{dC}$=48.4±1.1 pA (N=7, n=1830), and $I_{dT}$=41.9±1.2 pA (N=4, n=2407), respectively. At a lower voltage of 140 mV, both narrower Gaussian widths and reduced separations were observed within the distributions, with $I_{dA}$=43.6±0.4 pA (n=117), $I_{dG}$=37.5±0.6 pA (n=93), $I_{dC}$=29.2±0.3 pA (n=87), and $I_{dT}$=24.4±0.5 pA (n=169). The bulkier purines, dA and dG, have greater residual currents than the pyrimidines, dT and dC, indicating that steric restriction is not the primary determinant of residual current values, as has been noticed in α-hemolysin.

The residual currents due to the different homopolymer hairpin tails are well separated and well resolved. For example, the residual ion current difference between poly-dA and poly-dC is $I_{dA}$-$I_{dC}$=14.4±0.5 pA in 1 M KCl using a 140 mV driving voltage. MspA provides a minimum 3.5-times enhanced separation of nucleotide specific currents in comparison to α-hemolysin.

Example 3: Exploring the Region of Sensitivity in M1-NNN-MspA

The nucleotide location within the hairpin tail that influences the residual current was explored. For this a series of hairpin DNA with $(dC)_4$ [SEQ ID NO:55] sections at various positions in an otherwise poly-dA tail were used. When the $(dC)_4$ [SEQ ID NO:55] was adjacent to the hairpin duplex, the currents were identical to $I_{dC}$. When the $(dC)_4$ [SEQ ID NO:55] section was located more than three bases away from the hairpin duplex, the residual current was undifferentiated from $I_{dA}$ (Table A). To test the apparent importance of the first three nucleotides adjacent to the hairpin, tails with either $(dA)_3$ or $(dC)_3$ followed by two different random heteropolymers were used. The residual currents were found to be independent of the heteromeric section and to be indistinguishable from $I_{dA}$ or $I_{dC}$, respectively (see Table A). Given MspA's geometry, the hairpin duplex is expected to reside near the constriction. As fewer than 4 nucleotides influence the residual current, it is the nucleotides within and near the constriction of MspA that govern the residual currents.

Example 4: Single Nucleotide Recognition—a Precursor to Sequencing

Recognition and identification of individual nucleotide sites is required for nanopore sequencing. MspA's sensitivity to individual nucleotides was examined by making single nucleotide substitutions in the ssDNA hairpin tail. The substitution of a single nucleotide, dN in an otherwise poly-dA hairpin tail, in the first three positions as counted from the duplex, x=1,2,3, and is denoted $dN_x$. For example, a dC at the first position after the duplex (x=1) is called $dC_1$. FIGS. 4A-4D display the histograms of the averaged $I_{res}$. With a $dC_2$ substitution, $I_{res}$ is close to the current associated with poly-dC, $I_{dC}$. For a $dC_1$ substitution, the measured ion currents were between the ion currents found using homopolymers, $I_{dA}$ and $I_{dC}$. It was found that substitutions of $dT_1$, $dT_2$ and $dT_3$ cause an ion current between $I_{dA}$ and $I_{dT}$, with the current for the $dT_1$ substitution nearest to $I_{dT}$. A single dG within poly-dA does not appear to modulate the current appreciably from the current of a pure poly-dA, as might be expected from the relative closeness of $I_{dA}$ and $I_{dG}$. The residual current tends towards $I_{dA}$ as the heteronucleotide substitution is placed further from the duplex, giving additional evidence that the residual current signature is primarily due to the first two nucleotides after the duplex, and partly due the third nucleotide. See Table A for additional information on these hairpin tails and their associated residual current values.

The homopolymer background may influence the effect a heteronucleotide substitution has on $I_{res}$. This effect was examined by using a dA substitution in a poly-dC background (FIGS. 6A-6D). The residual current was affected by these substitutions at x=1,2,3, but the current differences from $I_{dC}$ were not as large as the influence of $dC_x$ substitutions in poly-dA. Similarly, a single dA was substituted in the background of poly-dT and did not produce as consistent of an influence on $I_{res}$ when compared to a $dT_x$ substitution in a background of poly-dA. These observations are not well described by a resistor model associated with each nucleotide substitution. However, the observed asymmetry may be qualitatively understood with rate limits to ion transport caused by energetic barriers (Example 7 below).

These results indicate that the short constriction zone of MspA is indeed responsible for nucleotide identification. Compared to α-hemolysin, MspA produces a larger and more focussed ion current density in its constriction zone. The length along of the constriction where the current is most sensitive to nucleotide identity is about the length of two nucleotides. It is possible that nucleotide specificity and spatial separation may be enhanced with additional mutations to MspA, especially since the data presented were taken using M1-NNN-MspA, the first MspA mutant to allow DNA translocation. Because of its importance to the residual current, the constriction will likely be a promising location for site-mutations. As such, other MspA mutants described herein, as well as other Msp porins, may be employed for embodiments described herein.

Example 5: Effect of the Hairpin Terminus on Ion Current

Since the hairpin duplex rests near MspA's constriction, it is possible that it also affects the ion current. To explore this, hairpin DNA was investigated with various duplex lengths but with the same terminal bases. The measured currents were found to be weakly dependent on the hairpin duplex length, with the longer duplex lengths inducing lower $I_{res}$ than shorter duplex lengths (see Table B). In further experiments, the original 14 bp duplex was preserved and only the terminal bp was varied. It was found that the residual current is strongly dependent on this terminal bp (Table B), altering $I_{res}$ by up to ~20%. In order to compare the influence of the hairpin's tail, the experiments presented above were acquired with the same 14 bp duplex.

Example 6: Duplex Interrupted (DI) Nanopore Sequencing

The ion current is uniquely sensitive to single stranded DNA nucleotides in MspA's constriction. While the speed of unimpeded ssDNA translocation is still too fast to utilize this sensitivity, the translocation speed of DNA can be controlled using duplex regions. The following section describes a DNA sequencing method using double stranded DNA sections to slow the translocation of DNA. With an existing biochemical conversion processes, short sections of double stranded DNA can be effectively placed between the nucleotides of an analyte DNA. When this converted DNA is driven through MspA, each duplex section sequentially halts the translocation. As the nucleotide of the analyte DNA is held in the confining aperture by the duplex section, the residual ion current can identify the analyte nucleotide. After one DNA duplex dissociates, the DNA quickly advances until the next DNA duplex pauses the translocation, allowing the next analyte nucleotide to be determined. The inventors term this method Duplex Interrupted (DI) nanopore sequencing.

DI sequencing depends on modifying the analyte DNA to have double stranded sections between each nucleotide to produce "converted" DNA. To explore the feasibility of DI sequencing, a synthesized DNA was used where each nucleotide of a hypothesized analyte DNA was followed by a 14 bp duplex region. The duplex sections had sequences identical to those of hairpins examined above and were formed by annealing complementary oligo nucleotides. Instead of using single nucleotides between each duplex section, tri-nucleotides were chosen to easily compare the ion currents to the well-characterized homopolymer hairpin experiments. A poly-dA tail was added to the 3' end of the synthesized sequence to initiate DNA threading into MspA. For example, the analyte sequence 3'-ATGC-5' [SEQ ID NO:1] would be converted to the analyzable DI-sequence: 5'duplex-CCC-duplex-GGA-duplex-TTT-duplex-AAA-$dA_{32}$ 3' [SEQ ID NO:9]. These synthesized sequences containing the tri-nucleotide regions could also be the product of DNA conversion (see, e.g., WO 2000/39333).

Figure 5A:
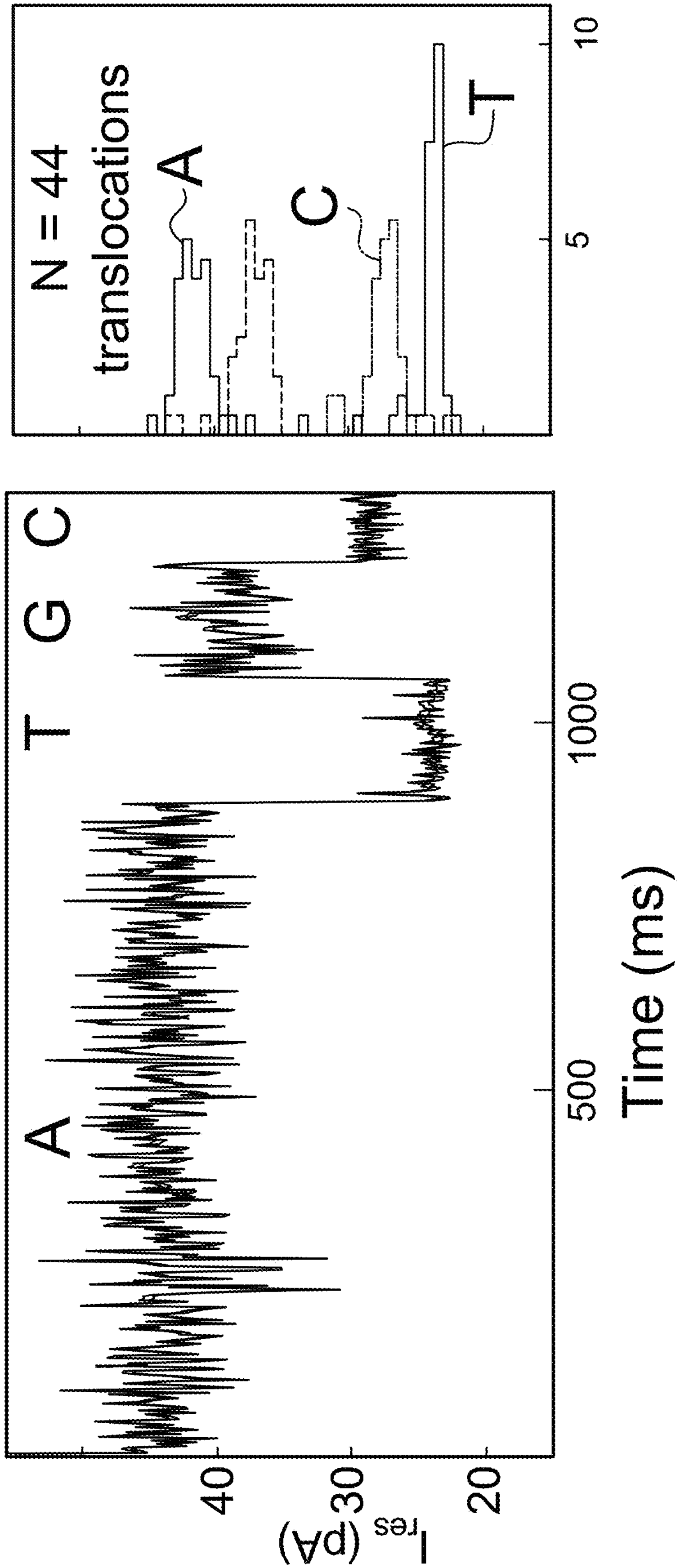
FIGS. 5A, 5B, and 5C depict demonstrations of duplex interrupted (DI) nanopore sequencing using MspA. Synthesized DNA simulating analyte DNA was converted to have duplexes between information carrying nucleotides. Each of these duplexes must be sequentially melted, or dissociated, as the DNA is pulled through the pore, enabling the residual current to determine the sequence. DNA chosen to represent different analyte sequences were employed: 3'-ATGC-5' [SEQ ID NO:1] (FIG. 5A); 3'-TACG-5' [SEQ ID NO:2] (FIG. 5B) and the "blind" sequence determined to be 3'-GTCAC-5' [SEQ ID NO:3] (FIG. 5C). Example traces of residual currents are shown to the left of each of FIGS. 5A, 5B, and 5C. Each step in the residual current is representative of three nucleotides within MspA's constriction held by a 14 bp DNA duplex. For each of these steps, a histogram of each level is shown on the right of each of FIGS. 5A, 5B, and 5C, for N translocations. These results are generated from 3 or more experiments at 140 mV. At higher voltages, the number of translocations increases (see the tables in FIGS. 10-12), but the level specificity decreases (see Tables A and B and the tables in FIGS. 10-12) due to reduced time averaging.
Figure 5B:
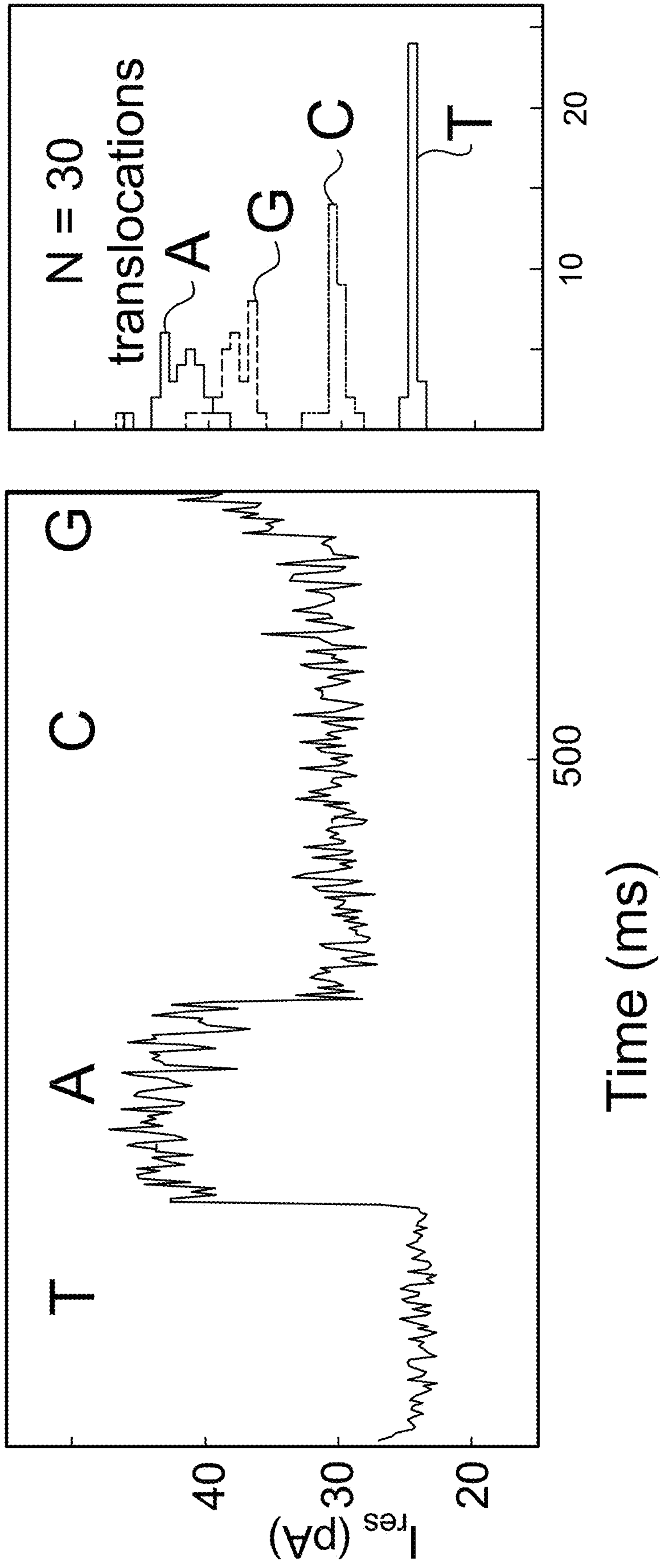

Using M1-NNN-MspA, the DNA constructs were examined for the analyte sequences 3'-ATGC-5'[SEQ ID NO:1] and 3'-TACG-5' [SEQ ID NO:2], both containing all four nucleotides. Successive discrete steps were observed in the ion current for synthesized sequences with residual currents shown in FIGS. 5A and 5B. Each level was consistent with one of the levels observed in the homopolymer hairpin experiments. Using an edge detection algorithm (see Example 7) on the translocations that had an average current of <25% of the open pore current, ~4% of the translocations were found to exhibit all four current levels, $I_{dA}$, $I_{dC}$, $I_{dT}$ and $I_{dG}$ in the anticipated order. In FIGS. 5A and 5B, four-level sample traces are shown recorded at 140 mV together with histograms of the average current of the levels found for many translocations. Additional data for DI sequencing at other voltages is presented in the FIGS. 7A-7C, 8A-8C, and 9A-9C. A large fraction of the translocations exhibited three or fewer distinct levels (see the tables of FIGS. 10-12. The levels found in these translocations also contained the homopolymer current levels with ordering consistent with the analyte sequence but with one or more levels missing. Without being bound by theory, the inventors believe that the translocations with fewer than four levels are due to incompletely annealed duplex regions or level durations that were too short (<1 ms) to be properly identified.

Figure 5C:
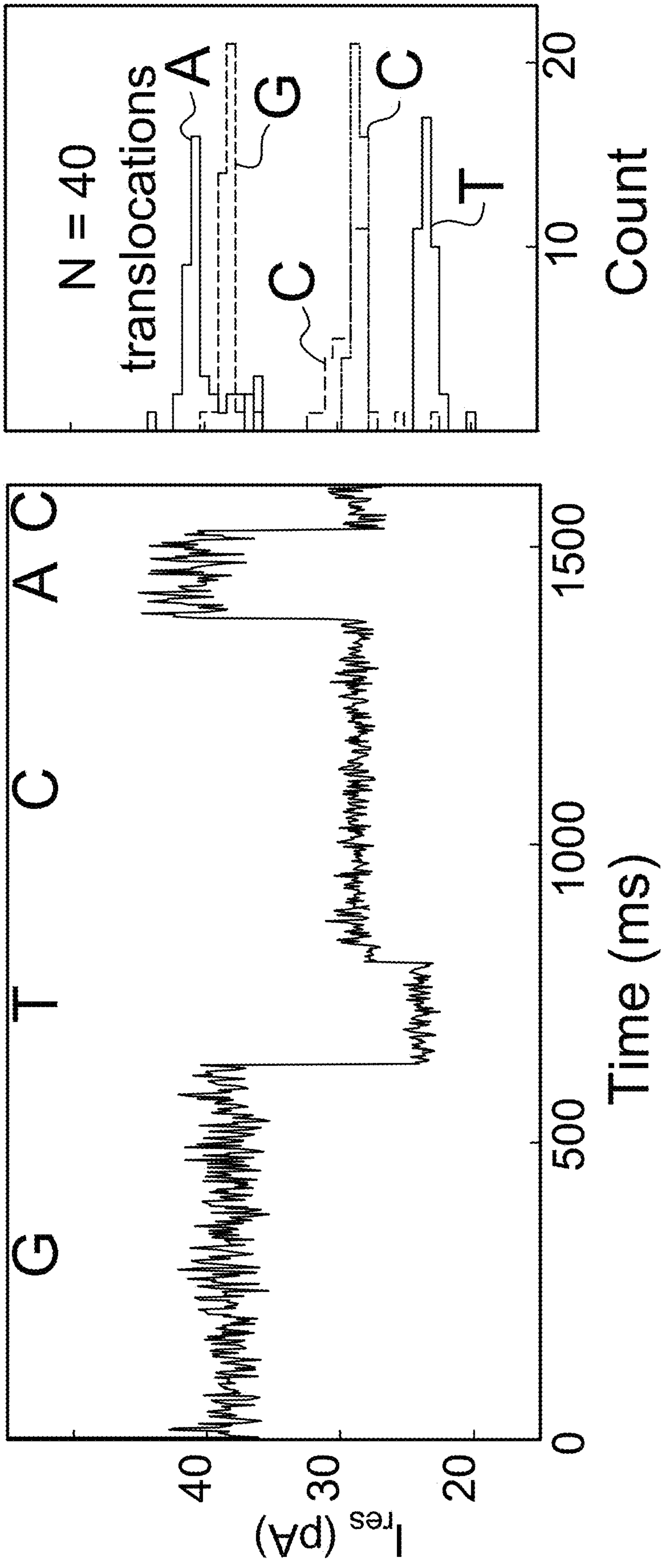
Figure 6A:
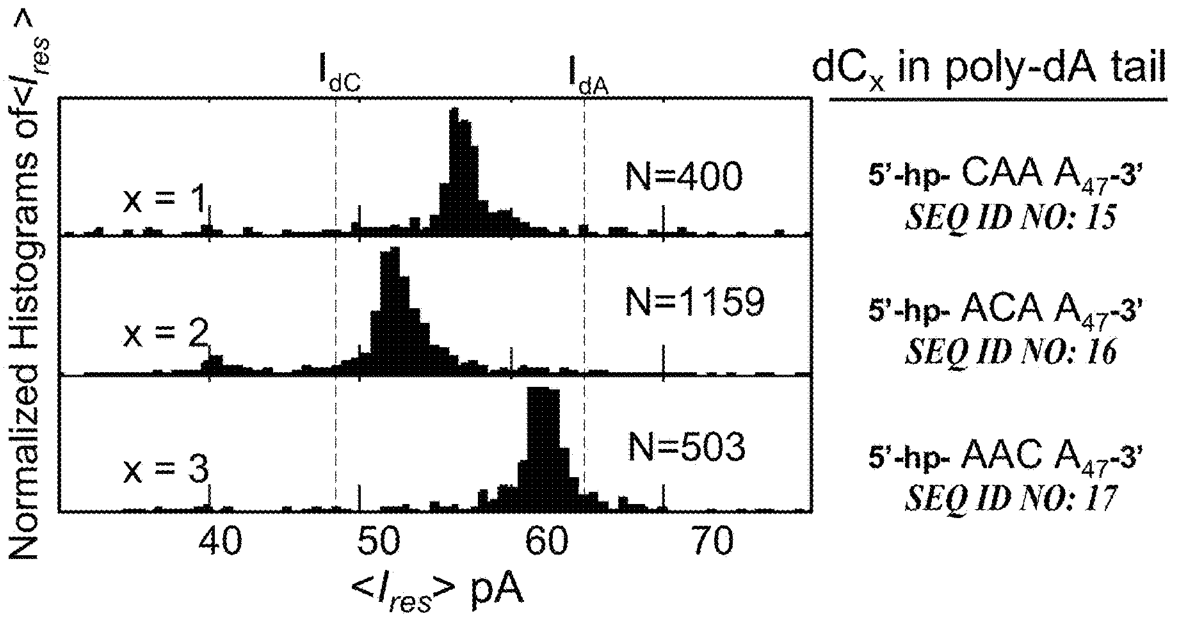
FIGS. 6A, 6B, 6C, and 6D are representative histograms of the average residual current, $<I_{res}>$ for a nucleotide dN insertions in homopolymer hairpin tails at position x away from the hairpin duplex, denoted $dN_X$. Vertical dashed lines indicate the Gaussian mean of the indicated homopolymer residual currents. Counts for each histogram are given by N. Note the effect of the homopolymer background on the effect of the nucleotide substitution.
Figure 6B:
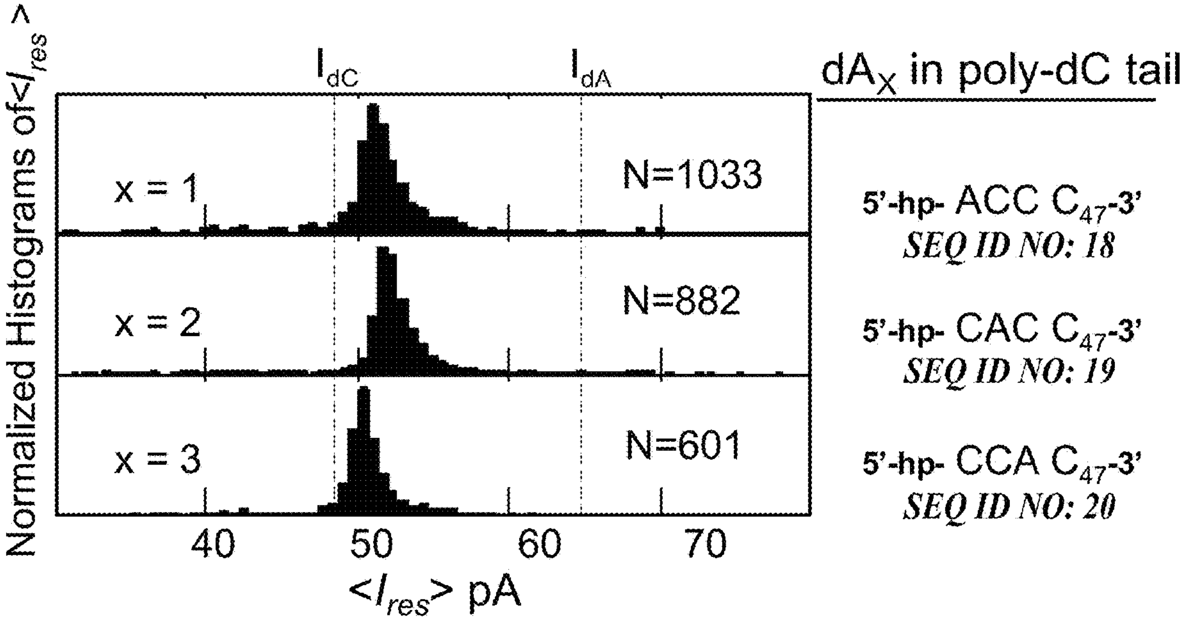
Figure 6C:
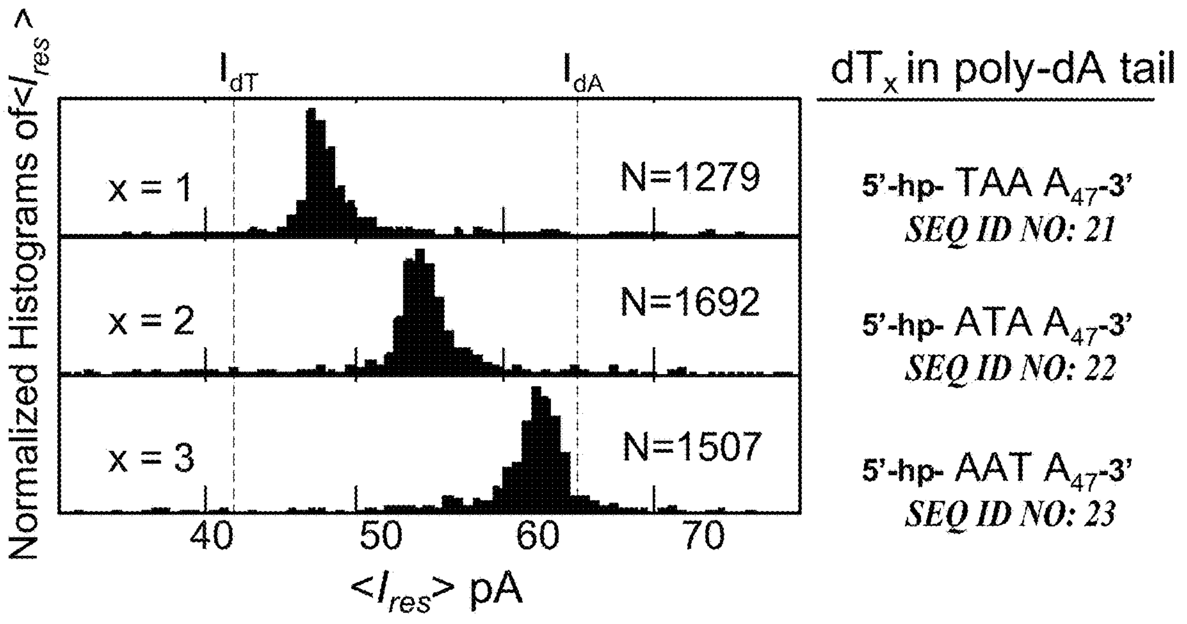
Figure 6D:
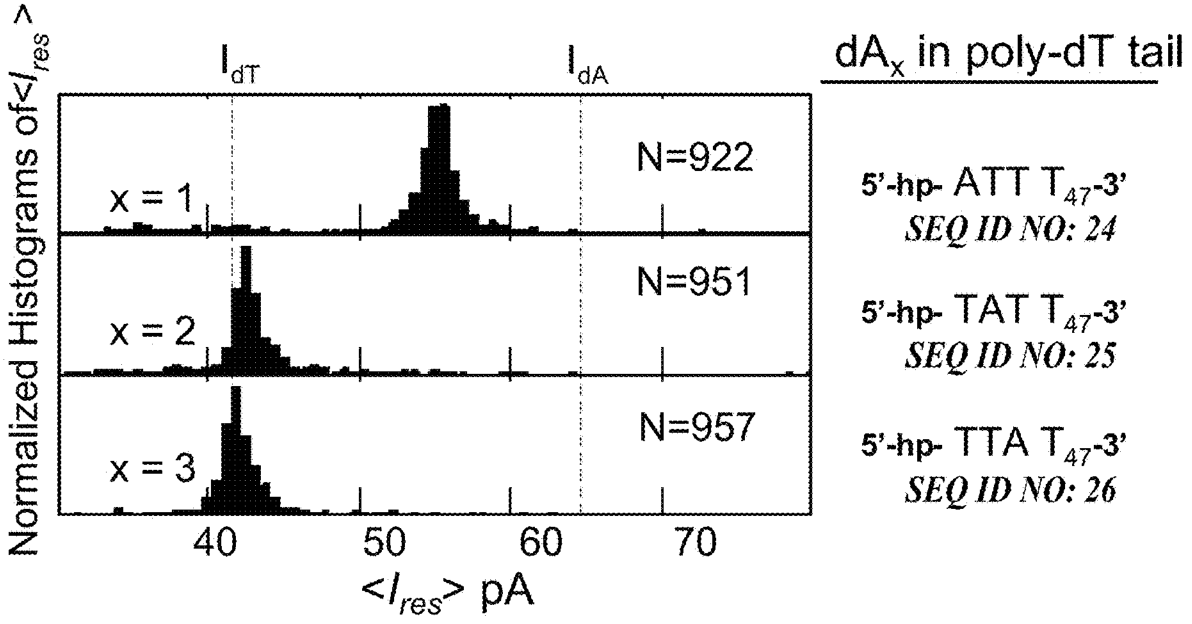
Figures 7A, 7B, 7C:
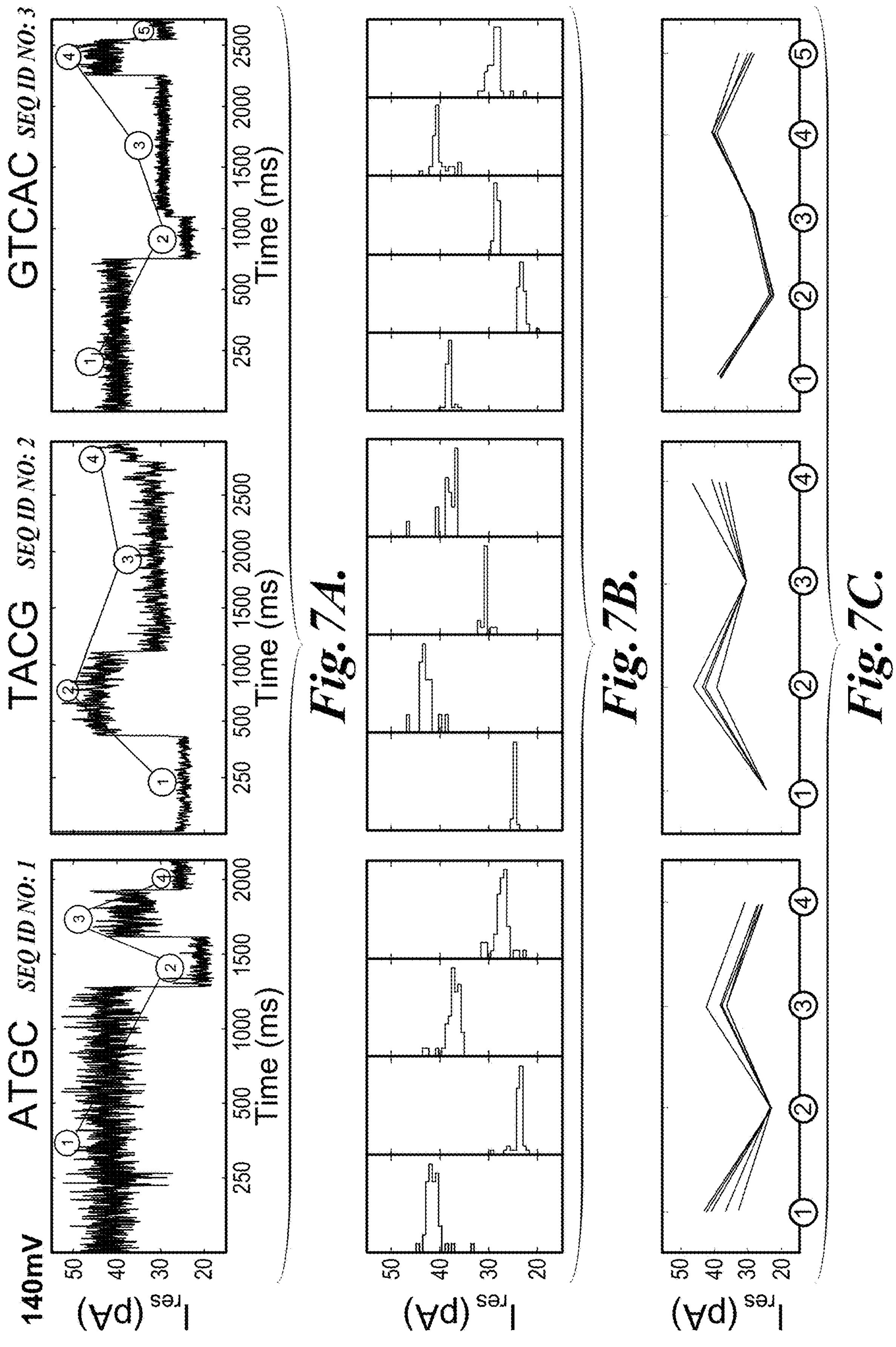
FIGS. 7A, 7B, and 7C present data from DI-sequencing examples for analyte DNA, 3'ATGC5' [SEQ ID NO:1] (left column) 3' TACG 5' [SEQ ID NO:2] (middle column) and blind DNA determined to be 3' GTCAC 5' [SEQ ID NO:3] (right column) at applied voltage of 140 mV. Each group of figures contains: (a) an example current trace containing 4 (or 5) levels, (b) histograms for each of the average current for each level from multiple events with 4 (or 5) levels and (c) a density plot indicating the transition between the current levels for the multiple events in the histograms. Unblocked pore current was 237.0±1.0 pA (mean±s.e.m.). Three or greater individual experiments with each DI-DNA were performed.
Figures 8A, 8B, 8C:
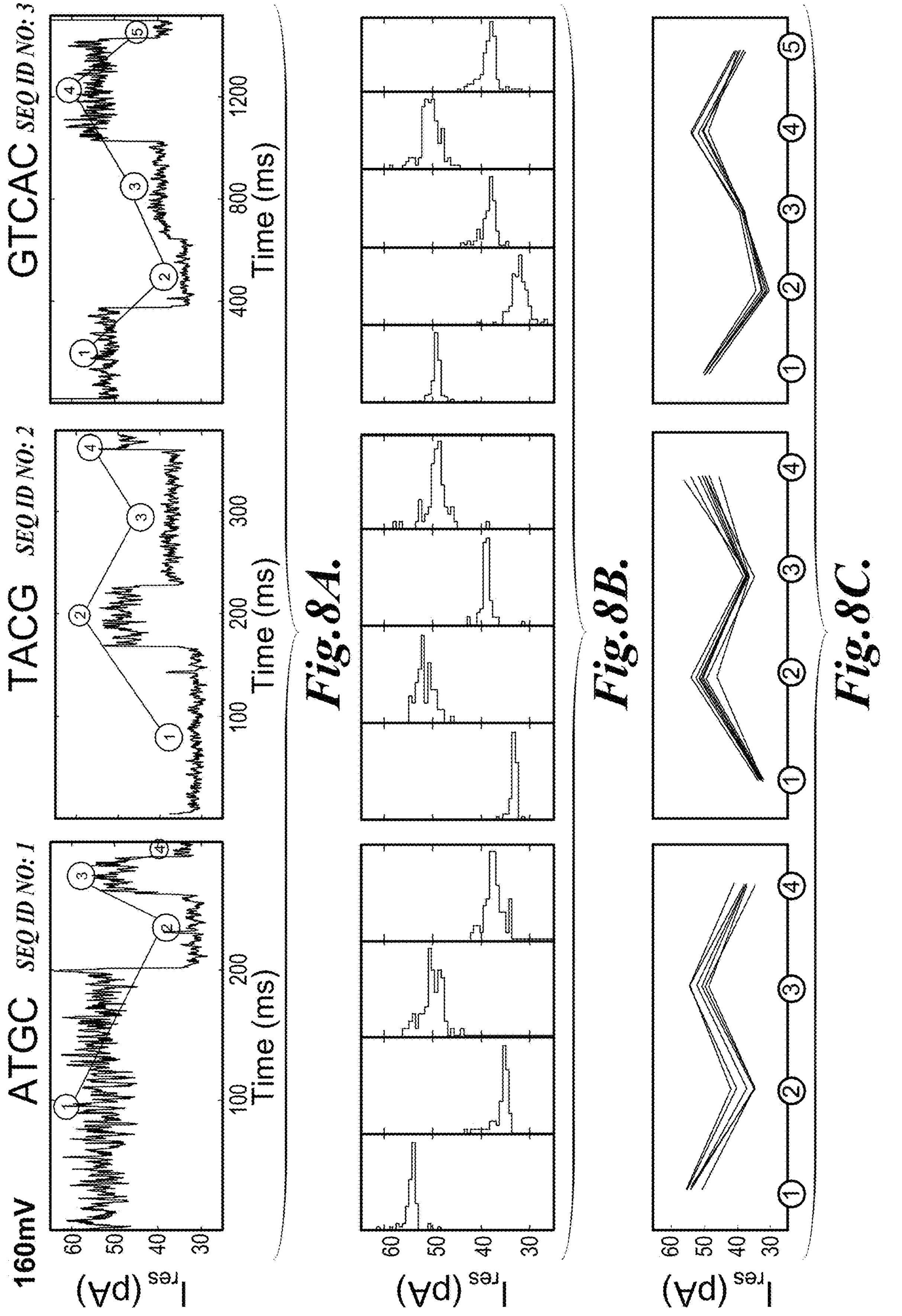
FIGS. 8A, 8B, and 8C represent data in a format similar to FIGS. 7A, 7B, and 7C but for an applied voltage of 160 mV. The unblocked pore current was 294.7±0.8 pA (mean±s.e.m.).
Figures 9A, 9B, 9C:
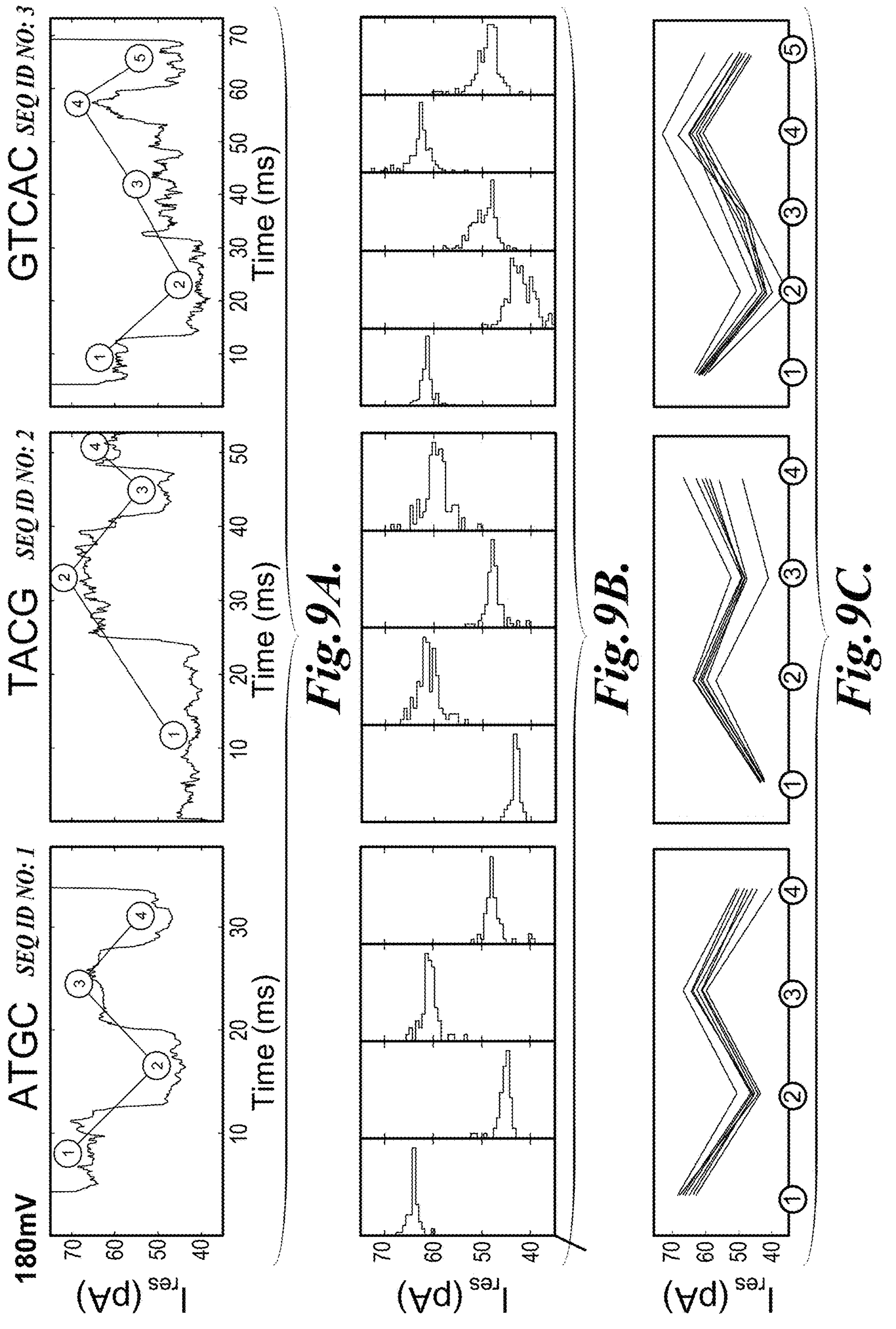
FIGS. 9A, 9B, and 9C represent data in a format similar to FIGS. 8A, 8B, and 8C but for an applied voltage of 180 mV. The unblocked pore current was 325.1±1.8 pA (mean±s.e.m.). At higher voltage, it becomes more difficult to distinguish unique levels in current traces because of the reduced time-averaging of current levels.

With the edge detection algorithm tuned by analyzing the DI sequences 3'-ATGC-5' [SEQ ID NO:1] and 3'-TACG-5' [SEQ ID NO:2], a blind test was conducted with synthesized DNA derived from a short sequence of unknown composition and length. It was determined that ~3% of the translocations exhibited five levels in the current traces corresponding to 3'-GTCAC-5' [SEQ ID NO:3], which was later confirmed to be the unknown sequence. FIG. 5C displays an example current trace from the blind test. These DI experiments provide the first demonstration of sequence information extracted from DNA molecules serially passing through a nanopore.

Nanopore sequencing must be able to distinguish repeat nucleotides using the residual current. With DI sequencing in MspA, this requirement may be accomplished by using a ‘fifth level’ (also called a separator level) that marks the progression to the next analyte nucleotide. The fifth level may be made by partitioning the interrupting-duplex with two separate complimentary oligos. The resulting first duplex produces the levels specific to analyte nucleotides and the second duplex produces a distinct level. The distinct fifth level can be made by choosing the second duplex to have terminal 5' (dC) (see Table B) that yields a residual current higher than the residual current of a 5' that is (dG) (see Table A). With this choice, the residual current would toggle between ~77 pA and the analyte nucleotide-specific currents between 42 pA and 66 pA using 180 mV voltage. The fifth level would separate the current level of every analyte nucleotide and would allow nucleotide repeats of any length to be read.

While an individual translocation may indicate the sequence, missed bases may require the statistics of multiple translocations to enhance the sequencing fidelity. Statistical analysis of current-level durations can provide additional information about sequence and missed nucleotides.

There is potential to optimize both the speed and sensitivity of DI sequencing by altering operating parameters such as pH and ionic strength of the buffer, using duplex-binding reagents, improving oligo annealing, and using more sophisticated data analysis techniques (see, e.g., BMC Bioinformatics B(Suppl 7):S14 (2007).

Example 7: Translocation Analysis Method and Qualitative Barrier Model

All software was custom designed in Matlab® (The Mathworks®). Translocation of DNA were first identified using current-thresholds and normalized by the surrounding open-pore current as described in U.S. Provisional Application Ser. No. 61/098,938 and its related PCT application, WO 2010/034018, each of which is incorporated herein by reference in its entirety. Minor variations in open-pore current levels were seen across a number of experiments and were likely due to minor changes in buffer conditions influencing conductivity. The fluctuations between experiments were minimized by dividing the residual current for each translocation by the surrounding unblocked current level. To report values in current, these normalized-currents were multiplied by the average open-pore current 325.1±1.8 pA (mean±s.e.m.) for an applied voltage of 180 mV and 252.2+/−3.0 for 140 mV applied voltage. Histograms of averaged residual currents were constructed using translocation with an average $I_{res}<0.5*I_{OS}$ and with a duration longer than 1 ms. Histograms are chosen from individual experiments that closely match the most frequent residual current when averaged over multiple experiments, as recorded in Tables A and B.

The residual currents were then Gaussian filtered at 4 kHz and down sampled at 20 kHz and further processed with a 20-point median filter. Transitions between current levels were identified with custom edge detection software utilizing a gradient threshold to detect transitions between unique levels. The local maxima of the current gradient were used to locate possible transitions. To be considered unique, levels within residual current traces were required to satisfy several conditions: level durations must be longer than 1.5 ms, each level's average current must be separated by both more than 3.8 pA from surrounding levels and by more than 1.5 times the quadrature sum of surrounding levels current fluctuation. If these requirements were not met, the levels were combined until possible levels were determined as unique. Residual current traces with four (or five in the case of the blind 3'-GTCAC-5' sequence [SEQ ID NO:3]) levels were found to follow patterns as seen in FIGS. 7A-7C, 8A-8C, and 9A-9C. Averages of these levels can be found in the tables of FIGS. 10-12. Information for events with fewer than 4 (or 5) events is summarized in the tables of FIGS. 10-12.

The data, shown in FIGS. 6A-6G, show the effect of substituting a nucleotide $dN_x$ at a position x=1,2,3 following the duplex terminus of a hairpin DNA. The nucleotides are substituted in poly-dA, poly-dC or poly-dT homopolymer tails. It was observed that the presence of $dC_x$ a $dT_x$ substitution in poly-dA causes the residual current to change towards the homopolymer value $I_{dC}$ and $I_{dT}$, respectively. The substitutions of a dA nucleotide in either poly-dC or poly-dT homopolymers do not consistently alter the current. It is possible that a qualitative model could describe this data.

It may be natural to expect each of these nucleotides to act like a resistor impeding the ionic flow. The data are not self-consistent with this description, as has been observed in α-hemolysin. Instead of a resistor model, and without being bound by theory, the inventors postulate that each of the amino acid residues within the constriction combined with the nucleotides in the constriction of MspA form a unique barrier to ion current. The presence of particular nucleotides, such as dC, dT, may induce a rate-limit to the ion transport. Below is a discussion of how the data are consistent with this model.

The observation that $I_{dC}<I_{dA}$ suggests that any dC nucleotide will present a higher barrier than dA nucleotides to ion transport. When a single $dC_x$ is put in poly-dA, the residual current is reduced by a rate-limit induced by the $dC_x$ barrier. The reduction in current due the $dC_x$ insertion is strongest at x=2, and somewhat less strong at x=1, likely because these locations would place the substitution in the narrowest part of MspA's constriction. When examining the influence of a $dA_x$ substitution in poly-dC tails, it is observed that the current is not appreciably increased. This is because the high-barrier dC nucleotides surrounding the $dA_x$ substitution induce a rate limit to the ion transport while the smaller barrier presented by the single dA cannot undo this rate limit.

A similar effect is observed when the high barrier caused by dT is put in a poly-dA tail: the current is considerably reduced as the substitution $dT_x$ is located inside the constriction, particularly at x=1. As $I_{dT}<I_{dA}$, these observations support the possibility that specific nucleotides induce rate limits to ion flow. Further implications of this model indicate when the substitution $dA_1$ is made in poly-dT, the dT at the second position will be the next nucleotide available to induce a rate-limit to ionic transport. As would be expected, it is observed that the $dT_2$ substitution in poly-dA induces a rate-limited current with distribution similar to current due to the $dA_1$ substitution in poly-dT. The difference in which location the substitution $dC_x$ and $dT_x$ is most influential in poly-dA (x=2, and x=1, respectively), may be attributed to the specific interactions between the nucleotides with the pore and the hairpin terminus.

Also provided is a system comprising an Msp porin having a vestibule and a constriction zone that define a tunnel, wherein the tunnel is positioned between a first liquid medium and a second liquid medium, wherein at least one liquid medium comprises an analyte, and wherein the system is operative to detect a property of the analyte. A system may be operative to detect a property of any analyte comprising subjecting an Msp porin to an electric field such that the analyte interacts with the Msp porin. A system may be operative to detect a property of the analyte comprising subjecting the Msp porin to an electric field such that the analyte electrophoretically translocates through the tunnel of the Msp porin. Also provided is a system comprising an Msp porin having a vestibule and a constriction zone that define a tunnel, wherein the tunnel is positioned in a lipid bilayer between a first liquid medium and a second liquid medium, and wherein the only point of liquid communication between the first and second liquid media occurs in the tunnel. Moreover, any Msp porin described herein may be comprised in any system described herein.

Any system described herein may further comprise a patch-clamp amplifier or a data acquisition device. A system may further comprise one or more temperature regulating devices in communication with the first liquid medium, the second liquid medium, or both.

Any system described herein may be operative to translocate an analyte through an Msp porin tunnel either electrophoretically or otherwise.

While illustrative embodiments have been illustrated and described, it will be appreciated that various changes can be made therein without departing from the spirit and scope of the invention.

---

The invention claimed is:

1. A system comprising:

a protein nanopore positioned between a cis side comprising a first conductive liquid medium and a trans side comprising a second conductive liquid medium, wherein the protein nanopore is disposed in an artificial membrane spanning the opening of an aperture, wherein the membrane comprises a mycolic acid and has a rupture voltage greater than 1.0 V when voltage applied across the membrane is ramped at about 100 mV/s in the presence of a 1.0 M KCl solution prepared with deionized water, and buffered to pH 8.0±0.05 with 10 mM HEPES, and wherein the protein nanopore provides liquid communication between the cis side and the trans side, and a data acquisition device operable to detect an ion current through the protein nanopore;

a nucleic acid analyte in the first liquid medium, wherein the nucleic acid analyte comprises a first arresting construct and a second arresting construct, and wherein the first arresting construct is configured to pause the advance of the nucleic acid analyte toward the trans side after entry of the nucleic acid analyte into the protein nanopore for a time sufficient to detect a first ion current level and then allow the nucleic acid analyte to advance toward the trans side.

2. The system of claim 1, wherein the protein nanopore is a *Mycobacterium smegmatis* porin (Msp) or mutant thereof, or a-hemolysin or a variant thereof.

3. The system of claim 1, wherein the first ion current level detectable by the data acquisition device represents a first nucleotide or set of nucleotides adjacent to the first arresting construct, wherein the first residual ion current level is different than a measurable ion current of the same nucleotide or set of nucleotides in an analyte that is not arrested.

4. The system of claim 1, wherein the nucleic acid analyte comprises a first nucleic acid sequence and the first arresting construct comprises a second nucleic acid that forms a duplex with the first nucleic acid sequence.

5. The system of claim 1, wherein the nucleic acid analyte comprises a first nucleic acid and the second arresting construct comprises a second nucleic acid that forms a duplex with the first nucleic acid.

6. The system of claim 1, wherein at least one arresting construct is an insert arresting construct.

7. The system of claim 1, wherein at least one arresting construct is a pendant arresting construct.

8. The system of claim 1, wherein the first arresting construct is identical to the second arresting construct.

9. The system of claim 1, wherein the each of the first and second arresting constructs is a duplex DNA.

10. The system of claim 1, further comprising a patch clamp amplifier in communication with the first liquid medium, the second liquid medium, or both.

11. The system of claim 1, further comprising optical patch clamps in communication with the first liquid medium, the second liquid medium, or both.

12. The system of claim 1, wherein the data acquisition device is in communication with the first liquid medium, the second liquid medium, or both.

13. The system of claim 1, further comprising one or more temperature regulating devices in communication with the first liquid medium, the second liquid medium, or both.

14. The system of claim 1, further comprising a source of an electric field capable of causing the nucleic acid analyte to enter into the protein nanopore.

15. The system of claim 1, further comprising a magnetic bead on the trans side capable of attaching to the nucleic acid analyte and a source of a magnetic field capable of causing the nucleic acid analyte to proceed further to the trans side through the protein nanopore.

16. The system of claim 1, wherein the system is operative to translocate the nucleic acid analyte through the protein nanopore from the cis side to the trans side.

17. The system of claim 1, wherein the system is operative to detect a property of the nucleic acid analyte.

18. The system of claim 1, wherein the second arresting construct is configured to pause the advance of the nucleic acid analyte toward the trans side after the first arresting construct has allowed the nucleic acid analyte to advance, wherein the pause for a time sufficient to detect a second ion current level.

19. A system comprising:

a protein nanopore positioned between a cis side comprising a first conductive liquid medium and a trans side comprising a second conductive liquid medium, wherein the protein nanopore is disposed in an artificial membrane spanning the opening of an aperture, wherein the membrane comprises a mycolic acid and has a rupture voltage greater than 1.0 V when voltage applied across the membrane is ramped at about 100 mV/s in the presence of a 1.0 M KCl solution prepared with deionized water, buffered to pH 8.0±0.05 with 10 mM HEPES and a voltage greater than 1.0 V is sustained for greater than 1 hour, and wherein the protein nanopore provides liquid communication between the cis side and the trans side, and a data acquisition device operable to detect an ion current through the protein nanopore;

a nucleic acid analyte in the first liquid medium, wherein the nucleic acid analyte comprises a first arresting construct and a second arresting construct, wherein the first arresting construct is configured to pause the advance of the nucleic acid analyte toward the trans side after entry of the nucleic acid analyte into the protein nanopore for a time sufficient to detect a first ion current level and then allow the nucleic acid analyte to advance toward the trans side, wherein the second arresting construct is configured to pause the advance of the nucleic acid analyte toward the trans side after the first arresting construct has allowed the nucleic acid analyte to advance for a time sufficient to detect a second ion current level, and wherein one of the first arresting construct and the second arresting construct is positioned on the nucleic acid analyte such that the first ion current level or the second ion current level is a separator level that differs from any nucleic acid unit-specific ion current level.

20. The system of claim 1, wherein the membrane has a rupture voltage greater than 2.0 V.

21. The system of claim 1, wherein the membrane can withstand a voltage greater than 1.0 V that is sustained for greater than 1 hour.

* * * * *